(12) United States Patent
Kolonin et al.

(10) Patent No.: US 9,539,341 B2
(45) Date of Patent: *Jan. 10, 2017

(54) METHODS AND COMPOSITIONS FOR TARGETING ADIPOSE CELLS IN MAMMALS

(71) Applicant: Board of Regents, the University of Texas System, Austin, TX (US)

(72) Inventors: Mikhail G. Kolonin, Houston, TX (US); Alexes Daquinag, Houston, TX (US); Yan Zhang, Houston, TX (US)

(73) Assignee: BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/682,335

(22) Filed: Apr. 9, 2015

(65) Prior Publication Data

US 2016/0000930 A1 Jan. 7, 2016

Related U.S. Application Data

(63) Continuation of application No. 14/007,836, filed as application No. PCT/US2012/031623 on Mar. 30, 2012, now Pat. No. 9,029,321.

(60) Provisional application No. 61/469,345, filed on Mar. 30, 2011.

(51) Int. Cl.
| | | |
|---|---|---|
| *A61K 47/48* | (2006.01) | |
| *C07K 7/06* | (2006.01) | |
| *A61K 38/10* | (2006.01) | |
| *C07K 7/64* | (2006.01) | |
| *A61K 38/00* | (2006.01) | |

(52) U.S. Cl.
CPC ......... *A61K 47/48246* (2013.01); *A61K 38/10* (2013.01); *A61K 47/48346* (2013.01); *C07K 7/06* (2013.01); *C07K 7/64* (2013.01); *A61K 38/00* (2013.01); *C07K 2319/00* (2013.01); *C07K 2319/33* (2013.01)

(58) Field of Classification Search
CPC .. A61K 38/00; A61K 38/10; A61K 47/48246; A61K 47/48346; C07K 2319/00; C07K 2319/33; C07K 7/06; C07K 7/64
See application file for complete search history.

(56) References Cited

U.S. PATENT DOCUMENTS

| | | |
|---|---|---|
| 7,214,786 B2 | 5/2007 | Kovalic et al. |
| 2006/0094672 A1 | 5/2006 | Pasqualini et al. |
| 2006/0239968 A1 | 10/2006 | Arap et al. |
| 2007/0044171 A1 | 2/2007 | Kovalic et al. |
| 2008/0124277 A1 | 5/2008 | Arap et al. |
| 2008/0176792 A1 | 7/2008 | Arap et al. |
| 2008/0229451 A1 | 9/2008 | Cao et al. |
| 2009/0104117 A1 | 4/2009 | Arap et al. |
| 2009/0221505 A1 | 9/2009 | Kolonin et al. |
| 2010/0172864 A1 | 7/2010 | Arap et al. |
| 2011/0020882 A1 | 1/2011 | de Souza et al. |
| 2011/0033391 A1 | 2/2011 | Weiner et al. |
| 2011/0209246 A1 | 8/2011 | Kovalic et al. |
| 2011/0296543 A1 | 12/2011 | Chang et al. |
| 2011/0321197 A1 | 12/2011 | Schön et al. |

FOREIGN PATENT DOCUMENTS

| | | |
|---|---|---|
| JP | 2004-529621 | 9/2004 |
| WO | WO 02/064748 | 8/2002 |
| WO | WO 2009/088482 | 7/2009 |
| WO | WO 2009/088949 | 7/2009 |
| WO | WO 2010/046221 | 4/2010 |
| WO | WO 2012/169911 | 12/2012 |

OTHER PUBLICATIONS

Olulanu H. Aina, Therapeutic Cancer Targeting Peptides, Biopolymers (Peptide Science), vol. 66, 184-199 (2002).*
Mechanisms of Carcinogenesis, 2010, International Agency for Research on Cancer, Section 3.*
Barnhart et al., "A peptidomimetic targeting white fat causes weight loss and improved insulin resistance in obese monkeys", *Sci Transl Med.*, 3(108):108ra112, 2011.
Caplan and Correa, "The MSC: an injury drugstore", *Cell Stem Cell*, 9(1):11-15, 2011.
Daquinag et al., "An isoform of decorin is a resistin receptor on the surface of adipose progenitor cells", *Cell Stem Cell*, 9:74-86, 2011.
Database UniProt (Online), "Subname: Full=Putative uncharacterized protein", EBI Accession No. H7CK07_LISMN, 2012.
Database UniProt (Online), "Subname: Full=Chloride intracellular channel exc-4", EBI Accession No. C1BSN1_9MAXI, 2009.
Database UniProt (Online), "Subname: Full=Related to anaphase promoting complex subunit 10", EBI Accession No. G4TC53_PIRID, 2011.
GenBank Accession No. ABM77181, "conserved hypothetical protein [*Prochlorococcus marinus* str. MIT 9303]", 2007.
GenBank Accession No. ACO12034, "Chloride intracellular channel exc-4 [*Lepeophtheirus salmonis*]", 2009.
GenBank Accession No. CAE21688, "conserved hypothetical protein [*Prochlorococcus marinus* str. MIT 9313]", 2003.
Gimble et al., "Prospecting for adipose progenitor cell biomarkers: biopanning for gold with in vivo phage display", *Cell Stem Cell*, 9(1):1-2, 2011.
Office Communication issued in Chinese Patent Application No. 201280023148.6, dated Dec. 31, 2014. (English Translation).
Office Communication issued in Chinese Patent Application No. 201280023148.6, dated Oct. 23, 2015. (English Translation).
Extended European Search Report issued in European Patent Application No. 12764703.0, dated Jun. 16, 2016.

(Continued)

*Primary Examiner* — James H Alstrum Acevedo
*Assistant Examiner* — Erinne Dabkowski
(74) *Attorney, Agent, or Firm* — Parker Highlander PLLC

(57) ABSTRACT

Methods and compositions are presented for use in diagnostic, imaging or targeting of therapeutic agents to treat obesity/adiposity-associated disorders, compositions and methods identify and use peptides to selectively target adipose tissue stromal cells in mammals.

15 Claims, 25 Drawing Sheets

(56) References Cited

OTHER PUBLICATIONS

Office Communication issued in Chinese Patent Application No. 201280023148.6, dated Jul. 4, 2016. (English Translation).

Office Communication issued in Japanese Patent Application No. 2014-502865, dated Mar. 1, 2016. (English Translation).

Daquinag et al., "Targeted proapoptotic peptides depleting adipose stromal cells inhibit tumor growth", *Mol. Ther.*, 24(1): 34-40, 2016.

* cited by examiner

Unpassaged Human WAT SVF

|  | control | WAT7-KLAKLAK$_2$ |
|---|---|---|
|  | FIG. 14A | FIG. 14B |

Tumor

| FIG. 14C | FIG. 14D |
|---|---|

Tumor

FIG. 14E    FIG. 14F scWAT

FIG. 14G    FIG. 14H ipWAT

SEQUENCE LISTING

```
<160> NUMBER OF SEQ ID NOS: 44

<210> SEQ ID NO 1
<211> LENGTH: 10
<212> TYPE: PRT
<213> ORGANISM: Artificial
<220> FEATURE:
<223> OTHER INFORMATION: Synthetic Peptide

<400> SEQUENCE: 1

Cys Lys His Tyr Gly Gly Gly Val Ala Cys
1               5                   10

<210> SEQ ID NO 2
<211> LENGTH: 8
<212> TYPE: PRT
<213> ORGANISM: Artificial
<220> FEATURE:
<223> OTHER INFORMATION: Synthetic Peptide

<400> SEQUENCE: 2

Lys His Tyr Gly Gly Gly Val Ala
1               5

<210> SEQ ID NO 3
<211> LENGTH: 10
<212> TYPE: PRT
<213> ORGANISM: Artificial
<220> FEATURE:
<223> OTHER INFORMATION: Synthetic Peptide

<400> SEQUENCE: 3

Cys Tyr Lys Asn Val Asp Ser Gly Gly Cys
1               5                   10

<210> SEQ ID NO 4
<211> LENGTH: 8
<212> TYPE: PRT
<213> ORGANISM: Artificial
<220> FEATURE:
<223> OTHER INFORMATION: Synthetic Peptide

<400> SEQUENCE: 4

Tyr Lys Asn Val Asp Ser Gly Gly
```

```
1               5

<210> SEQ ID NO 5
<211> LENGTH: 9
<212> TYPE: PRT
<213> ORGANISM: Artificial
<220> FEATURE:
<223> OTHER INFORMATION: Synthetic Peptide

<400> SEQUENCE: 5

Cys Arg Phe Leu Leu Pro Gln Gly Cys
1               5

<210> SEQ ID NO 6
<211> LENGTH: 7
<212> TYPE: PRT
<213> ORGANISM: Artificial
<220> FEATURE:
<223> OTHER INFORMATION: Synthetic Peptide

<400> SEQUENCE: 6

Arg Phe Leu Leu Pro Gln Gly
1               5

<210> SEQ ID NO 7
<211> LENGTH: 9
<212> TYPE: PRT
<213> ORGANISM: Artificial
<220> FEATURE:
<223> OTHER INFORMATION: Synthetic Peptide

<400> SEQUENCE: 7

Cys Tyr Glu Gly Ser Glu Val Ser Cys
1               5

<210> SEQ ID NO 8
<211> LENGTH: 7
<212> TYPE: PRT
<213> ORGANISM: Artificial
<220> FEATURE:
<223> OTHER INFORMATION: Synthetic Peptide

<400> SEQUENCE: 8

Tyr Glu Gly Ser Glu Val Ser
1               5

<210> SEQ ID NO 9
<211> LENGTH: 9
<212> TYPE: PRT
<213> ORGANISM: Artificial
<220> FEATURE:
<223> OTHER INFORMATION: Synthetic Peptide

<400> SEQUENCE: 9

Cys Leu Arg Gln Gly Asn Pro Thr Cys
1               5

<210> SEQ ID NO 10
<211> LENGTH: 7
<212> TYPE: PRT
<213> ORGANISM: Artificial
<220> FEATURE:
<223> OTHER INFORMATION: Synthetic Peptide

<400> SEQUENCE: 10

Leu Arg Gln Gly Asn Pro Thr
1               5
```

```
<210> SEQ ID NO 11
<211> LENGTH: 10
<212> TYPE: PRT
<213> ORGANISM: Artificial
<220> FEATURE:
<223> OTHER INFORMATION: Synthetic Peptide

<400> SEQUENCE: 11

Cys Gly Ser Gly Gly Met Ser Pro Ser Cys
1               5                   10

<210> SEQ ID NO 12
<211> LENGTH: 8
<212> TYPE: PRT
<213> ORGANISM: Artificial
<220> FEATURE:
<223> OTHER INFORMATION: Synthetic Peptide

<400> SEQUENCE: 12

Gly Ser Gly Gly Met Ser Pro Ser
1               5

<210> SEQ ID NO 13
<211> LENGTH: 10
<212> TYPE: PRT
<213> ORGANISM: Artificial
<220> FEATURE:
<223> OTHER INFORMATION: Synthetic Peptide

<400> SEQUENCE: 13

Cys Ser Trp Lys Tyr Trp Phe Gly Glu Cys
1               5                   10

<210> SEQ ID NO 14
<211> LENGTH: 8
<212> TYPE: PRT
<213> ORGANISM: Artificial
<220> FEATURE:
<223> OTHER INFORMATION: Synthetic Peptide

<400> SEQUENCE: 14

Ser Trp Lys Tyr Trp Phe Gly Glu
1               5

<210> SEQ ID NO 15
<211> LENGTH: 10
<212> TYPE: PRT
<213> ORGANISM: Artificial
<220> FEATURE:
<223> OTHER INFORMATION: Synthetic Peptide

<400> SEQUENCE: 15

Cys Gly Gln Trp Leu Gly Asn Trp Leu Cys
1               5                   10

<210> SEQ ID NO 16
<211> LENGTH: 8
<212> TYPE: PRT
<213> ORGANISM: Artificial
<220> FEATURE:
<223> OTHER INFORMATION: Synthetic Peptide

<400> SEQUENCE: 16

Gly Gln Trp Leu Gly Asn Trp Leu
1               5
```

<210> SEQ ID NO 17
<211> LENGTH: 9
<212> TYPE: PRT
<213> ORGANISM: Artificial
<220> FEATURE:
<223> OTHER INFORMATION: Synthetic Peptide

<400> SEQUENCE: 17

Cys Ala Val Tyr Arg Ser Thr Gly Cys
1               5

<210> SEQ ID NO 18
<211> LENGTH: 7
<212> TYPE: PRT
<213> ORGANISM: Artificial
<220> FEATURE:
<223> OTHER INFORMATION: Synthetic Peptide

<400> SEQUENCE: 18

Ala Val Tyr Arg Ser Thr Gly
1               5

<210> SEQ ID NO 19
<211> LENGTH: 10
<212> TYPE: PRT
<213> ORGANISM: Artificial
<220> FEATURE:
<223> OTHER INFORMATION: Synthetic Peptide

<400> SEQUENCE: 19

Cys Glu Ser Gly Phe Pro Thr Val Gly Cys
1               5                   10

<210> SEQ ID NO 20
<211> LENGTH: 8
<212> TYPE: PRT
<213> ORGANISM: Artificial
<220> FEATURE:
<223> OTHER INFORMATION: Synthetic Peptide

<400> SEQUENCE: 20

Glu Ser Gly Phe Pro Thr Val Gly
1               5

<210> SEQ ID NO 21
<211> LENGTH: 9
<212> TYPE: PRT
<213> ORGANISM: Artificial
<220> FEATURE:
<223> OTHER INFORMATION: Synthetic Peptide

<400> SEQUENCE: 21

Cys Leu Gly Val Gly Pro Gly Phe Cys
1               5

<210> SEQ ID NO 22
<211> LENGTH: 7
<212> TYPE: PRT
<213> ORGANISM: Artificial
<220> FEATURE:
<223> OTHER INFORMATION: Synthetic Peptide

<400> SEQUENCE: 22

Leu Gly Val Gly Pro Gly Phe
1               5

```
<210> SEQ ID NO 23
<211> LENGTH: 9
<212> TYPE: PRT
<213> ORGANISM: Artificial
<220> FEATURE:
<223> OTHER INFORMATION: Synthetic Peptide

<400> SEQUENCE: 23

Cys Ile Arg Gly Lys Ala Gly Arg Cys
1               5

<210> SEQ ID NO 24
<211> LENGTH: 7
<212> TYPE: PRT
<213> ORGANISM: Artificial
<220> FEATURE:
<223> OTHER INFORMATION: Synthetic Peptide

<400> SEQUENCE: 24

Ile Arg Gly Lys Ala Gly Arg
1               5

<210> SEQ ID NO 25
<211> LENGTH: 9
<212> TYPE: PRT
<213> ORGANISM: Artificial
<220> FEATURE:
<223> OTHER INFORMATION: Synthetic Peptide

<400> SEQUENCE: 25

Cys Lys Gly Gly Arg Ala Lys Asp Cys
1               5

<210> SEQ ID NO 26
<211> LENGTH: 7
<212> TYPE: PRT
<213> ORGANISM: Artificial
<220> FEATURE:
<223> OTHER INFORMATION: Synthetic Peptide

<400> SEQUENCE: 26

Lys Gly Gly Arg Ala Lys Asp
1               5

<210> SEQ ID NO 27
<211> LENGTH: 5
<212> TYPE: PRT
<213> ORGANISM: Artificial
<220> FEATURE:
<223> OTHER INFORMATION: Synthetic Peptide

<400> SEQUENCE: 27

Cys Ala Arg Ala Cys
1               5

<210> SEQ ID NO 28
<211> LENGTH: 3
<212> TYPE: PRT
<213> ORGANISM: Artificial
<220> FEATURE:
<223> OTHER INFORMATION: Synthetic Peptide

<400> SEQUENCE: 28

Ala Arg Ala
1

<210> SEQ ID NO 29
```

```
<211> LENGTH: 9
<212> TYPE: PRT
<213> ORGANISM: Artificial
<220> FEATURE:
<223> OTHER INFORMATION: Synthetic Peptide

<400> SEQUENCE: 29

Cys Gly Asp Lys Ala Lys Gly Arg Cys
1               5

<210> SEQ ID NO 30
<211> LENGTH: 8
<212> TYPE: PRT
<213> ORGANISM: Artificial
<220> FEATURE:
<223> OTHER INFORMATION: Synthetic Peptide

<400> SEQUENCE: 30

Gly Asp Lys Ala Lys Gly Arg Cys
1               5

<210> SEQ ID NO 31
<211> LENGTH: 14
<212> TYPE: PRT
<213> ORGANISM: Artificial
<220> FEATURE:
<223> OTHER INFORMATION: Synthetic Peptide

<400> SEQUENCE: 31

Lys Leu Ala Lys Leu Ala Lys Lys Leu Ala Lys Leu Ala Lys
1               5                   10

<210> SEQ ID NO 32
<211> LENGTH: 14
<212> TYPE: PRT
<213> ORGANISM: Artificial
<220> FEATURE:
<223> OTHER INFORMATION: Synthetic Peptide

<400> SEQUENCE: 32

Lys Leu Ala Lys Lys Leu Ala Lys Leu Ala Lys Lys Leu Ala
1               5                   10

<210> SEQ ID NO 33
<211> LENGTH: 14
<212> TYPE: PRT
<213> ORGANISM: Artificial
<220> FEATURE:
<223> OTHER INFORMATION: Synthetic Peptide

<400> SEQUENCE: 33

Lys Ala Ala Lys Lys Ala Ala Lys Ala Ala Lys Lys Ala Ala
1               5                   10

<210> SEQ ID NO 34
<211> LENGTH: 21
<212> TYPE: PRT
<213> ORGANISM: Artificial
<220> FEATURE:
<223> OTHER INFORMATION: Synthetic Peptide

<400> SEQUENCE: 34

Lys Leu Gly Lys Lys Leu Gly Lys Leu Gly Lys Lys Leu Gly Lys Leu
1               5                   10                  15

Gly Lys Lys Leu Gly
            20
```

```
<210> SEQ ID NO 35
<211> LENGTH: 9
<212> TYPE: PRT
<213> ORGANISM: Artificial
<220> FEATURE:
<223> OTHER INFORMATION: Synthetic Peptide

<400> SEQUENCE: 35

Cys Trp Leu Gly Glu Trp Leu Gly Cys
1               5

<210> SEQ ID NO 36
<211> LENGTH: 7
<212> TYPE: PRT
<213> ORGANISM: Artificial
<220> FEATURE:
<223> OTHER INFORMATION: Synthetic Peptide

<400> SEQUENCE: 36

Trp Leu Gly Glu Trp Leu Gly
1               5

<210> SEQ ID NO 37
<211> LENGTH: 14
<212> TYPE: PRT
<213> ORGANISM: Artificial
<220> FEATURE:
<223> OTHER INFORMATION: Synthetic peptide

<400> SEQUENCE: 37

Lys Phe Ala Lys Phe Ala Lys Lys Phe Ala Lys Phe Ala Lys
1               5                   10

<210> SEQ ID NO 38
<211> LENGTH: 14
<212> TYPE: PRT
<213> ORGANISM: Artificial
<220> FEATURE:
<223> OTHER INFORMATION: Synthetic peptide
<220> FEATURE:
<221> NAME/KEY: Misc_feature
<222> LOCATION: (2)..(2)
<223> OTHER INFORMATION: X is cyclohexyl-alanine
<220> FEATURE:
<221> NAME/KEY: Misc_feature
<222> LOCATION: (5)..(5)
<223> OTHER INFORMATION: X is cyclohexyl-alanine
<220> FEATURE:
<221> NAME/KEY: Misc_feature
<222> LOCATION: (9)..(9)
<223> OTHER INFORMATION: X is cyclohexyl-alanine
<220> FEATURE:
<221> NAME/KEY: Misc_feature
<222> LOCATION: (12)..(12)
<223> OTHER INFORMATION: X is cyclohexyl-alanine

<400> SEQUENCE: 38

Lys Xaa Ala Lys Xaa Ala Lys Lys Xaa Ala Lys Xaa Ala Lys
1               5                   10

<210> SEQ ID NO 39
<211> LENGTH: 10
<212> TYPE: PRT
<213> ORGANISM: Artificial
<220> FEATURE:
<223> OTHER INFORMATION: Synthetic peptide
<220> FEATURE:
<221> NAME/KEY: Misc_feature
<222> LOCATION: (1)..(2)
<223> OTHER INFORMATION: residues 1 and 2 are joined by a 6-carbon alkyl
``` chain residue in the peptide backbone
<220> FEATURE:
<221> NAME/KEY: Misc_feature
<222> LOCATION: (3)..(4)
<223> OTHER INFORMATION: residues 3 and 4 are joined by a 6-carbon alkyl
        chain residue in the peptide backbone
<220> FEATURE:
<221> NAME/KEY: Misc_feature
<222> LOCATION: (6)..(7)
<223> OTHER INFORMATION: residues 6 and 7 are joined by a 6-carbon alkyl
        chain residue in the peptide backbone
<220> FEATURE:
<221> NAME/KEY: Misc_feature
<222> LOCATION: (8)..(9)
<223> OTHER INFORMATION: residues 8 and 9 are joined by a 6-carbon alkyl
        chain residue in the peptide backbone

<400> SEQUENCE: 39

Lys Ala Lys Ala Lys Lys Ala Lys Ala Lys
1               5                   10

<210> SEQ ID NO 40
<211> LENGTH: 11
<212> TYPE: PRT
<213> ORGANISM: Mus musculus

<400> SEQUENCE: 40

Leu Ile Ser Met Cys Pro Tyr Arg Cys Gln Cys
1               5                   10

<210> SEQ ID NO 41
<211> LENGTH: 55
<212> TYPE: PRT
<213> ORGANISM: Mus musculus

<400> SEQUENCE: 41

Met Lys Ala Thr Leu Ile Phe Phe Leu Leu Ala Gln Val Ser Trp Ala
1               5                   10                  15

Gly Pro Phe Glu Gln Arg Gly Leu Phe Asp Phe Met Leu Glu Asp Glu
            20                  25                  30

Ala Ser Gly Ile Ile Pro Tyr Asp Pro Asp Asn Pro Leu Ile Ser Met
        35                  40                  45

Cys Pro Tyr Arg Cys Gln Cys
    50                  55

<210> SEQ ID NO 42
<211> LENGTH: 60
<212> TYPE: PRT
<213> ORGANISM: Homo sapiens

<400> SEQUENCE: 42

Met Lys Ala Thr Ile Ile Leu Leu Leu Ala Gln Val Ser Trp Ala
1               5                   10                  15

Gly Pro Phe Glu Gln Arg Gly Leu Phe Asp Phe Met Leu Glu Asp Glu
            20                  25                  30

Ala Ser Gly Ile Gly Pro Glu Val Pro Asp Asp Arg Asp Phe Glu Pro
        35                  40                  45

Ser Ser Gly Pro Val Cys Pro Phe Arg Cys Gln Cys
    50                  55                  60

<210> SEQ ID NO 43
<211> LENGTH: 24
<212> TYPE: PRT
<213> ORGANISM: Artificial Sequence
<220> FEATURE:

```
<223> OTHER INFORMATION: Synthetic Peptide
<220> FEATURE:
<221> NAME/KEY: MISC_FEATURE
<222> LOCATION: (1)..(2)
<223> OTHER INFORMATION: residues 1 and 2 are joined by a 6-carbon alkyl
      chain residue in the peptide backbone
<220> FEATURE:
<221> NAME/KEY: MISC_FEATURE
<222> LOCATION: (3)..(4)
<223> OTHER INFORMATION: residues 3 and 4 are joined by a 6-carbon alkyl
      chain residue in the peptide backbone
<220> FEATURE:
<221> NAME/KEY: MISC_FEATURE
<222> LOCATION: (6)..(7)
<223> OTHER INFORMATION: residues 6 and 7 are joined by a 6-carbon alkyl
      chain residue in the peptide backbone
<220> FEATURE:
<221> NAME/KEY: MISC_FEATURE
<222> LOCATION: (8)..(9)
<223> OTHER INFORMATION: residues 8 and 9 are joined by a 6-carbon alkyl
      chain residue in the peptide backbone

<400> SEQUENCE: 43

Lys Ala Lys Ala Lys Lys Ala Lys Ala Lys Lys Leu Ala Lys Leu Ala
1               5                   10                  15

Lys Lys Leu Ala Lys Leu Ala Lys
            20

<210> SEQ ID NO 44
<211> LENGTH: 24
<212> TYPE: PRT
<213> ORGANISM: Artificial Sequence
<220> FEATURE:
<223> OTHER INFORMATION: Synthetic peptide

<400> SEQUENCE: 44

Cys Ser Trp Lys Tyr Trp Phe Gly Glu Cys Lys Leu Ala Lys Leu Ala
1               5                   10                  15

Lys Lys Leu Ala Lys Leu Ala Lys
            20
```

METHODS AND COMPOSITIONS FOR TARGETING ADIPOSE CELLS IN MAMMALS

CROSS-REFERENCE TO RELATED APPLICATIONS

The present application is a continuation of U.S. application Ser. No. 14/007,836, filed Sep. 26, 2013, as a national phase application under 35 U.S.C. §371 of International Application No. PCT/US2012/031623, filed Mar. 30, 2012, which claims the benefit of U.S. Provisional Application Ser. No. 61/469,345 filed Mar. 30, 2011, both of which are herein incorporated by reference in their entireties for all purposes.

SEQUENCE LISTING REFERENCE

The sequence listing that is contained in the file named "UTSHP0300USC1_ST25.txt", which is ~11 KB (as measured in Microsoft Windows®) and was created on Apr. 6, 2015, is filed herewith by electronic submission and is incorporated by reference herein.

TECHNICAL FIELD

This disclosure relates to methods and compositions which can be used to target delivery of therapeutic agents. More specifically, the present disclosure relates to compositions and methods for identification and use of peptides that selectively target adipose tissue in mammals both in vitro and in vivo.

BACKGROUND

Transplantation of stem cells is accepted as a way to boost tissue regeneration in preclinical trials, and this strategy is being translated to the bedside (Kolonin and Simmons, *Nat. Biotechnol.* 27, 252-253, 2009). Stem cell therapy would greatly benefit from a capacity to target mesenchymal stromal cells (MSC) in specific organs for imaging or therapeutic applications. MSC are a mixed cell population that comprises multipotent adult progenitor cells (Bianco, et al., *Cell Stem Cell* 2, 313-319, 2008). Due to the ability of these cells to differentiate into mesenchymal lineages, such as osteoblasts, chondrocytes, and adipocytes, they are commonly referred to as mesenchymal stem cells (Pittenger, et al., *Science* 284, 143-147, 1999; Prockop, *Science* 276, 71-74, 1997). Recent studies reveal that MSC function as perivascular cells (pericytes) maintaining vascular integrity (Crisan, et al., *Cell Stem Cell* 3, 301-313, 2008; Tang, et al., *Science* 322, 583-586, 2008; Traktuev et al., *Circ. Res.* 102, 77-85, 2008).

Preclinical studies and clinical trials with transplanted MSC support the therapeutic potential of these cells and suggest that these cells are also activated during disease to participate in tissue repair and regeneration. However, the clinical application of MSC for cell therapy require the ability to track and control this plastic cell population, due to safety concerns related to their capacity to promote cancer (Zhang et al., *Cancer Res.* 69, 5259-5266, 2009).

MSC were originally isolated from the bone marrow stroma and termed fibroblast colony-forming units (CFU-F) based on their fibroblastic morphology (Friedenstein, Haematol. Blood. Transfus. 25, 19-29, 1980). Since then, MSC have been identified in the majority of adult organs, with white adipose tissue (WAT) being the largest reservoir of MSC, these cells being termed adipose stromal cells (ASC: Gimble et al., *Circ. Res.* 100, 1249-1260, 2007; Daquinag et al., *Trends in Pharmacol. Sci.* 22, 1-8, 2011). While WAT is primarily composed of adipocytes, ASC constitute the majority of cells in the stromal/vascular fraction (SFV), which also contains endothelial cells (EC) and infiltrating hematopoietic cells (Hausman et al., *Obes. Rev.* 2, 239-254, 2001). ASC have been revealed to be a rich source of multipotent progenitors that display multipotency and proliferation capacity comparable to those of bone marrow MSC, while also having clear unique features (Rodeheffer et al., *Cell* 135, 240-249, 2008; Tang et al., 2008, ibid; Zuk et al., 2001, *Tissue Eng.* 7, 211-228).

Current understanding of the mechanisms through which intercellular interactions of MSC with other tissue components mediate tissue remodeling is limited by the lack of specific MSC markers. While a number of cell surface molecules, including platelet-derived growth factor receptor-β (PDGFRβ), CD146, CD44, CD90, CD105, CD73, CD29, and Stro-1, have been used for positive selection of MSC, each one of them is also expressed on other cell types (Bianco et al., 2008, ibid; Gimble et al., 2007, ibid; Nie et al., *Stem Cells* 26, 2735-2745, 2008). MSC (including those from WAT) can be distinguished from hematopoietic cells based on the lack of the pan-leukocyte marker CD45 and from endothelial cells (EC) based on the lack of the pan-endothelial marker CD31/PECAM-1 (Bianco et al., 2008, ibid; Rodeheffer et al., 2008, ibid). Because CD34 is expressed on perivascular MSC of several organs in vivo, the CD34+CD45−CD31− immunophenotype has been used to separate MSC from other cells (Gimble et al., 2007 ibid; Tang et al., 2008, ibid; Traktuev et al., 2008, ibid; Zhang et al., 2009, ibid). However, because this signature does not differentiate MSC in different tissues, new markers for prospective isolation and tracking of ASC and MSC in other tissues are urgently needed and are constraining the field of stem cell transplantation as a whole.

Furthermore, adipose associated disorders include, but are not limited to, obesity, body weight and body composition disorders, including eating and other disorders effecting regulation of body fat and body weight, represent major health problems in all industrialized countries. The prevalence of obesity in developed countries is high. For example, by the year 2002 approximately 30% of Americans were obese (National Health and Nutrition Examination Survey). Obesity is a condition in which there is an excess of body fat relative to lean body mass, and is defined as a body mass index (weight/height$^2$) greater than 30 kg/m$^2$ (Kopelman, *Nature* 404:635-643, 2000). Obesity is associated with an increased risk of developing many serious diseases, including, but not limited to, type 2 diabetes, stroke, hypertension, coronary artery disease, certain cancers, chronic fibrosis in certain tissues, fatty liver disease, chronic venous insufficiency, deep vein thrombosis, arthritis, breathing problems such as obstructive sleep apnea, and gallbladder diseases such as cholelithiasis, among other complications (Willett et al., *N. Engl. J. Med.* 341:427-434, 1999).

Of further note, stromal cells are connective tissue cells that support the function of the parenchymal cells of an organ. Fibrosis is a pathologic process, which includes scar formation and over production of extracellular matrix, by the connective tissue, as a response to tissue damage. Confluent fibrosis can obliterate the normal architecture and function of the underlying organ or tissue. Fibrotic disorders, include but are not limited to, pathologic scarring in the skin, such as, colloid and hypertrophic scar; cirrhosis of liver and gallbladder, fibrosis in the heart, eye and the kidneys, pulmonary and bone-marrow, fibrosis in the gastro intestinal tract, that associated with cancers, such as sarcomas and hemangiopericytoma as well as scleroderma. Additional fibrotic disorder include scurvy and autoimmune disorders such as rheumatoid arthritis and systemic lupus erythematosus and genetic disorders examples of which include Marfan syndrome, Ehlers-Danlos syndrome, Loeys-Dietz syndrome, pseudoxanthoma elasticum, osteogenesis imperfect, fibrodysplasia ossificans progressive and spontaneous pneumothorax, among others.

The above mentioned disease associations explain why the economic costs of obesity are estimated to be more than 100 billion dollars (Daniels, *Am. J. Nurs.* 106:40-49, 2006), which is estimated to be as much as 7% of total health care costs (Seidell, *Int. J. Obes. Relat. Metab. Disord.* 19(Suppl 6):S13-S16, 1995).

The regulation of body composition in mammals is a complex process that involves the regulation of both appetite and energy expenditure. Human body composition and body weight homeostasis is poorly understood. The epidemiology of obesity strongly shows that the disorder exhibits inherited characteristics, and human twin studies strongly suggest a substantial genetic basis in the control of body composition and body weight, with estimates of heritability on the order of 80-90 percent. Studies of the genetics of human obesity and of animal models demonstrate that obesity results from the complex interactions of defective regulation of food intake, food induced energy expenditure, and the balance between lipid and lean body anabolism. Thus, obesity is not merely the result of negative behavior, i.e., the result of voluntary hyperphagia, but results from differences in eating patterns, metabolism, and neurologic/metabolic interactions. These differences seem to be due, in some degree, to differences in gene expression, either the level or activity of gene products (Friedman et al., *Mamm. Genome* 1:130-144, 1991).

Current methods for control of body weight include dieting and surgical procedures. However, diet is often unsuccessful and the few obesity therapeutics approved by the U.S. Food and Drug Administration, such as Phentermen, fenfluramine, Meridia, Xernical, Orlistat, Adipex-P, Bontril and Ionomin have unacceptable or dangerous adverse effects and those few that have been approved have been removed from the marketplace. Surgical methods for weight reduction, such as liposuction, gastric bypass or banding surgeries, have many risks. None of the presently available methods for weight control is satisfactory and a need exists for improved methods of weight loss and control.

In addition to the obesity problem in the human population, there is a growing problem of obesity in companion animals, such as dogs and cats (German, *J. Nutr.* 136:1940S-1946S, 2006). In the United States, it is estimated that 25-40% of all dogs and cats are overweight or obese. As in humans, obesity can have detrimental effects on the health and longevity of companion animals. Additionally, the ability to reduce or eliminate the use of body composition and body weight manipulators in commercial livestock feed has significant utility not only in savings to the grower, but to the consumer and to society as a whole. Therefore, the ability to manipulate body composition and body weight and to treat body composition disorders in humans and companion animals such as, but not limited to, obesity, and the ability to increase the size of livestock, have broad utility and represent significant opportunities.

Diabetes is a long-term, currently incurable disorder, associated with body composition disorders, specifically obesity and the metabolic syndrome, with greatly increased risks for developing additional pathologic conditions resulting from poor glycemic control. Chronic, short-term risks include, but are not limited to, hypoglycemia, infections, and disorders associated with hyperglycemia, such as ketoacidosis. Long-term complications resulting from diabetes include, but are not limited to, heart disease, stroke, high blood pressure, vascular disease, visual impairment, nephropathy, and neuropathy. According to a 2005 survey by the National Institute of Diabetes and Digestive and Kidney Diseases, over 20 million people in the United States have diabetes, and the percentage of the population with diabetes is rapidly increasing. In 2005 in the United States, 1.5 million people were diagnosed with diabetes. Some studies project that about 250 million people worldwide will be afflicted by diabetes by the year 2020 (O'Rahilly, *BMJ,* 314: 955-959, 1997). The most prevalent forms of this disorder are insulin-dependent diabetes mellitus (IDDM or type I) and non-insulin-dependent diabetes mellitus (NIDDM or type II). Due to the high incidence of diabetes, and the irreversible damage that is incurred with many of the associated complications, the cost of treatment surpasses any other single disease in the United States. In 2002, more than $132 billion was spent on direct and indirect costs for treatment, with about $92 billion of that going to direct medical costs (Hogan et al., *Diabetes Care* 26:917-932, 2003).

Recently, obesity has emerged as one of the factors predisposing cancer patients to mortality as a result of advanced cancer progression (see for example, Daquinag et al., Vascular targeting of adipose tissue as an anti-obesity approach. *Trends in Pharmacol. Sci.* 22, 1-8, 2011; Zhang, et al. Adipose-tissue derived progenitor cells and cancer, *World Journal of Stem Cells* (Topic Highlight), 2 (5): 103-113, 2010; Bellows, et al., Influence of BMI on Level of Circulating Progenitor Cells, Obesity, online; Flegal, et al. Cause-specific excess deaths associated with underweight, overweight, and obesity. *JAMA.* 298, 2028-2037, 2007; Roberts, et al. Biological mechanisms linking obesity and cancer risk: new perspectives. *Annu Rev Med.* 61:301-316, 2010). Survival of patients with prostate and breast carcinomasis decreased by obesity more than for other cancers. WAT has a direct effect on cancer progression (Vona-Davis, et al., Adiposity, type 2 diabetes and the metabolic syndrome in breast cancer. Obes Rev; 8: 395-408, 2007) as a potent endocrine organ secreting numerous soluble adipokines implicated in inflammation and the metabolic syndrome (Rosen et al., Adipocytes as regulators of energy balance and glucose homeostasis. *Nature;* 444: 847-853, 2006). Insulin-like growth factors (IGFs) are among those that could directly stimulate tumor cell proliferation. Leptin, interleukin-6, as well as various other hormones and inflammatory cytokines, may also play a role (Baillargeon. Obesity adipokines and prostate cancer (review). Int J Oncol; 28: 737-745 2006). However, clinical and experimental data addressing the role of these factors in cancer has remained controversial. For example, in animal models ablation of circulating IGF-1 has shown no effect on prostate tumor growth (Anzo et al., Targeted deletion of hepatic Igf1 in TRAMP mice leads to dramatic alterations in the circulating insulin-like growth factor axis but does not reduce tumor progression. *Cancer Res;* 68(9):3342-9, 2008). Therefore, alternative mechanisms must be considered.

As opposed to WAT, whose physiological function is to store excess energy, brown adipose tissue (BAT) is responsible for energy dissipation in the form of heat. The fine balance between WAT and BAT is an important issue to take into consideration in designing targeting therapies. A number of results from the rodent models indicate that BAT has a protective effect against the pathological consequences of obesity. The significance of discovering BAT in adults lies in possible new approaches to treatment of obesity and of the associated disorders. ASCs are one of the progenitor cell types giving rise to BAT (Elabd et al. Human multipotent adipose-derived stem cells differentiate into functional brown adipocytes. Stem Cells 27, 2753-2760, 2009). More importantly, white adipocytes can be directly converted to a BAT-like phenotype both in culture and in vivo (Cinti. Transdifferentiation properties of adipocytes in the adipose organ. Am. J. Physiol. Endocrinol. Metab. 297, 977-986, 2009). In mice, expansion of residual BAT "patches" within WAT can lead to virtually all adipose depots becoming BAT-like at the expense of WAT. The apparent dependence of adipocyte physiology on the status of the vasculature suggests that vascular-targeting agents could be designed to convert WAT into BAT, rather than destroying tissue altogether, as a more physiological and safer anti-obesity treatment. Development of pharmacological approaches to activate proliferation, vascularization and/or metabolism of the existing residual BAT could, in theory, tilt the WAT/BAT balance and be used to treat obesity.

In summary, adipose associated body composition and body weight disorders such as obesity and diabetes represent major health problems. Given the severity, prevalence, and complexity of adipose associated body weight disorders, there exists a great need to identify genes and proteins that participate in body composition and body weight control, and to develop new drugs and therapies to treat adipose associated body composition disorders, obesity, metabolic syndrome, and diabetes. Targeting treatment and imaging modalities to different type of cells in adipose tissue (WAT and BAT), such as ASC, can be beneficial for biomedical applications in obesity, cancer and fibrosis.

SUMMARY

The presently disclosed methods and compositions are based, in part, on the discovery and identification of certain peptides that can be used to aid in diagnosis, prevention, and/or treatment of adipose associated disorders such as, but not limited to, body composition disorders, body weight disorders, diabetes, obesity, or metabolic syndrome, as well as cancer and fibrosis, in mammals.

In some embodiments of the present invention, a targeting peptide comprises an amino acid sequence selected from the group consisting of SEQ ID NOS: 1-16, wherein said peptide binds to stromal cells. In another embodiment of the present invention, the targeting peptide comprises the WAT7 amino acid sequence SWKYWFGE of SEQ ID NO 13 and SEQ ID NO 14. In other embodiments described herein, a protein composition comprises a targeting peptide, and in a further embodiment a protein composition comprises the WAT7 amino acid sequence.

In some embodiments, the targeting peptide is composed entirely of D-amino acids, in other embodiments, the targeting peptide is composed entirely of L-amino acids, and in further embodiments the targeting peptide may comprise L amino acids, D amino acids or combinations thereof.

In some embodiments of the invention, a protein composition comprises WAT7, wherein WAT7 is comprised of D-amino acids, and wherein said composition binds to stromal cells in adipose tissue, fibrotic tissue or tumor tissue. In some further embodiments of the protein composition, WAT7 selectively binds to ΔDCN on the surface of ASC cells.

In some embodiments of the protein composition of the current invention, a targeting peptide is coupled to an effector agent selected from the group comprising: an imaging agent; a cytotoxic agent; a pro-apoptotic agent; a fusion protein; a cytostatic agent; a cytocidal agent; radioisotope; an ACS cell differentiating agent; mitotic inhibitors, antitumor agents; antibiotic agent, enzymes; chemotherapeutic agent; anti-angiogenic agents or a combination thereof. In some embodiments, of the protein composition, the targeting peptide and effector agent are comprised of D-amino acids; in other embodiments of the protein composition, the targeting peptide is comprised of L-amino acids, and the effector comprises D-amino acids; in further still embodiments of the protein composition, targeting peptide is comprised of L-amino acids, and the effector comprises L-amino acids.

In some embodiments of the protein composition disclosed herein, the target peptide is coupled to an effector agent and induces a white adipose tissue to convert to a brown adipose tissue. In further embodiments, the effector agent activates b3-adrenergic receptors in white adipose tissue. In some embodiments of the protein composition, the effector agent is a peptide composed of D-amino acids.

In one embodiment a method of making a protein composition to target adipose tissue, comprises: coupling an effector agent to a targeting peptide, wherein the targeting peptide is comprised of an amino acid sequence selected from the group consisting of SEQ ID NOS: 1-16; and wherein said targeting peptide selectively targets cellular adipose tissue. In further embodiments, the effector agent and targeting peptide are comprised of D-amino acids. In other embodiments the effector is comprised of L-amino acids; and the targeting peptide are comprised of D-amino acids.

In some embodiments of the method of making a protein composition disclosed herein, coupling comprises linking said effector agent to said targeting peptide with a linking moiety; in further embodiments, the linking moiety comprises aminohexanoic acid; $(CH_2)_4$; $(CH_2)_5$; $(CH_2)_6$; $(CH_2)_7$; $(CH_2)_8$ or a combination thereof. In some embodiments of the method of method of making a protein composition disclosed herein, the effector agent is selected from the group comprising a cytotoxic agent; a pro-apoptotic agent; an imaging agent or combinations thereof.

In some embodiments a method of delivering an effector agent to an adipose tissue comprises: exposing a protein composition comprising: an effector agent coupled to a peptide, wherein the peptide is comprised of an amino acid sequence less than 100 amino acids in length, and wherein the amino acid sequence comprises an adipose tissue targeting peptide moiety having an amino acid sequence selected from the group consisting of SEQ ID NOS: 1-16; to a population of cells comprising adipose tissue. In further embodiments, the protein composition comprises a linker, and in said linker may be comprised of comprises aminohexanoic acid; $(CH_2)_4$; $(CH_2)_5$; $(CH_2)_6$; $(CH_2)_7$; $(CH_2)_8$ or a combination thereof. In some embodiments the targeting peptide motif is comprised of D-amino acids. In other embodiments, the effector agent and said targeting peptide are comprised of D-amino acids. In some embodiments of the method of delivering an effector agent to an adipose tissue described herein, the agent comprises: a cytotoxic agent; a pro-apoptotic agent; an imaging agent or combinations thereof, and in further embodiments the agent is comprised of D-amino acids.

In some embodiments of the method of delivering an effector agent to an adipose tissue, said exposing comprises:

exposing a subject to said protein composition to treat an adiposity-associated disorder, wherein said disorder comprises obesity; fibrosis; cancer or a combination thereof; and in further embodiments, said population of cells is in a mammalian subject; in still further embodiments, the population of cells is in a human subject; in some other embodiments, the population of cells is a thin section of a tissue.

Some embodiments of the method of delivering an effector agent to an adipose tissue further comprising detecting adipose stromal cells in said population based on said selective binding of protein composition to said adipose tissue. In other embodiments the method of the delivering an effector agent to an adipose tissue, the adiposity-associated disorder is a body composition disorder; a body weight disorder; obesity; lypodystrophy; diabetes; metabolic syndrome, fibrosis; cancer or a combination thereof.

In one embodiment a peptide is disclosed comprising an amino acid sequence selected from the group consisting of SEQ ID NOS: 17-24, wherein said peptide binds to lung tissue. In further embodiments a protein composition is disclosed comprising a peptide comprising a sequence selected from SEQ ID NOS: 17-24 or combinations thereof. In further embodiments, the protein composition is comprised of D-amino acids. In some embodiments of the protein composition, the peptide is coupled to an imaging agent; a cytotoxic agent; a pro-apoptotic agent or combinations thereof.

In some embodiments of the protein composition disclosed herein, the composition comprises a targeting peptide and an effector agent, wherein said effector agent comprises: gramicidin; magainin; mellitin; defensing; cecropin; (KFAKFAK)$_2$ (SEQ ID NO: 37), (KFXAKFXAK)$_2$ (SEQ ID NO: 38); (KHexAKHexAK)$_2$(KLAKLAK)$_2$ (SEQ ID NO: 43); (KLAKKLA)$_2$ (SEQ ID NO: 32); (KAAKKAA)$_2$ (SEQ ID NO: 33); (KLGKKLG)$_3$ (SEQ ID NO: 34); angiotensin; laminin peptides; fibronectin peptides; plasminogen activator inhibitors; tissue metalloproteinase inhibitors; interferons; interleukin 12; platelet factor 4; IP-10; Gro-β; thrombospondin; 2-methoxyoestradiol; proliferin-related protein; carboxiamidotriazole; CM101; Marimastat; pentosan polysulphate; angiopoietin 2 (Regeneron); interferon-alpha; herbimycin A; PNU145156E; 16K prolactin fragment; Linomide; thalidomide; pentoxifylline; genistein; TNP470; endostatin; paclitaxel; accutin; angiostatin; cidofovir; vincristine; bleomycin; AGM-1470; platelet factor 4 or minocycline; 5-fluorouracil; bleomycin; busulfan; camptothecin; carboplatin; chlorambucil; cisplatin (CDDP); cyclophosphamide; dactinomycin; daunorubicin; doxorubicin; estrogen receptor binding agents; etoposide (VP16); farnesyl-protein transferase inhibitors; gemcitabine; ifosfamide; mechlorethamine; melphalan; mitomycin; navelbine; nitrosurea; plicomycin; procarbazine; raloxifene; tamoxifen; taxol; temazolomide (an aqueous form of DTIC); transplatinum; vinblastine and methotrexate; vincristine; alkylating agents; antimetabolites; antitumor antibiotics; corticosteroid hormones; mitotic inhibitors; nitrosoureas; hormone agents; mitotic inhibitors; antitumor antibiotics; enzymes; biological response modifiers; plant alkaloids; docetaxel; etoposide (VP16); teniposide; paclitaxel; taxol; vinblastine; vincristine; vinorelbine; PPAR-gamma agonists thiazolidinediones; rosiglitazone; fluorophores; metal chelate complexes; radioisotopes; fluorescent markers; urease; alkaline phosphatase; liposomes; microcapsules; microparticles; nanoparticles; magnetic beads; microdevices; bleomycin; dactinomycin; daunorubicin; doxorubicin (Adriamycin); plicamycin (mithramycin) and idarubicin; platinum coordination complexes; anthracenediones; substituted ureas; methyl hydrazine derivatives; amsacrine; L-asparaginase; and tretinoin. Carboplatin; cisplatin (cis-DDP); mitoxantrone; hydroxyurea; procarbazine; IgFc fusions proteins; enzyme fusion proteins; fluorescent protein; luminescent proteins or combinations and analogs thereof.

Thus, embodiments described herein comprise a combination of features and advantages intended to address various shortcomings associated with prior art methods of diagnosis, prevention, and/or treatment of adipose associated disorders. The various characteristics described above, as well as other features, will be readily apparent to those skilled in the art upon reading the following detailed description, and by referring to the accompanying drawings.

BRIEF DESCRIPTION OF THE DRAWINGS

FIGS. 14A-H show that treatment with the targeted cytotoxic peptide, WAT7-KLAKLAK2 (SEQ ID NO:13-SEQ ID NO:31) all-D-peptide has depleted the ASC present in subcutaneous WAT (panel F versus E) but the effect on intraperitoneal WAT is significantly greater (panel H versus G) and also results in tumor necrosis (as shown in panels B versus A and panel D versus C).

BRIEF DESCRIPTION OF THE SEQUENCE LISTING

Figure 1A:
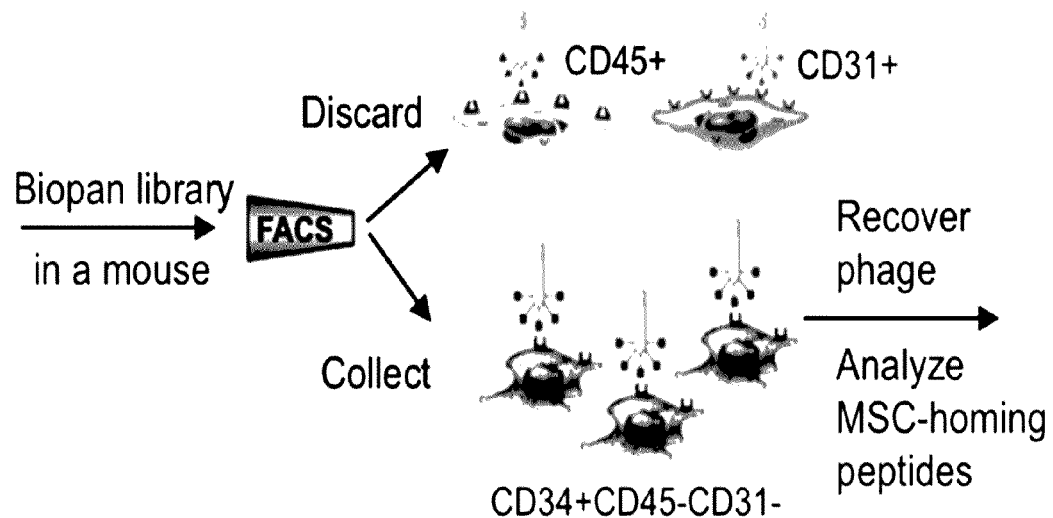
FIGS. 1A-C depict the screen for MSC-homing peptides. (A) depicts the schematic for a screen for peptides homing to organ-specific MSC populations. A mixture of three phage-displayed cyclic peptide libraries was used for 4 rounds of synchronous multi-organ biopanning. In every selection round, erythroid (TER119+), endothelial (CD31+) and hematopoietic (CD45+) cells were immunodepleted and then FACS was used to collect CD34+CD31−CD45− cells (MSC) from WAT, lung, bone marrow, and skeletal muscle. (B) Phage-peptides bound to WAT MSC (ASC), in parallel with phage-peptides bound to MSC of control organs, were quantified, amplified, pooled, and used for the next round of biopanning. Increased recovery of phage transforming units (TU) in successive rounds reflects the enrichment of phage-peptides homing to MSC of individual target organs. (C) Relative specificity of ASC homing assessed for individual phage-peptide clones separately injected into mice as a ratio of TU recovered on WAT to CD34+CD31−CD45− to TU recovered on lung CD34+CD31−CD45− cells. Fd-Tet: control insertless phage. Values shown are mean±SD for triplicate measurements.

The Sequence Listing provides amino acid sequences of peptides that bind mammalian adipose tissue and lung tissue. The amino acid sequences of cysteine-cyclized peptides that bind to white adipose tissue (WAT1-8) are presented in SEQ ID NOS: 1, 3, 5, 7, 9, 11, 13 and 15. Corresponding non-cysteine-cyclized peptides are presented in SEQ ID NOS: 2, 4, 6, 8, 10, 12 and 14.

The amino acid sequences of cysteine-cyclized peptides that bind lung tissue (LU1-4) are presented in SEQ ID NOS: 17, 19, 21 and 23 with corresponding non-cysteine-cyclized peptides are presented in SEQ ID NOS: 18, 20, 22 and 24.

The amino acid sequences of a previously disclosed adipose binding peptide (cysteine-cyclized) is presented as SEQ ID NO: 25 with the corresponding non-cysteine-cyclized peptide sequence presented as SEQ ID NO: 26.

The amino acid sequences of various control peptides are presented as cysteine-cyclized peptides in SEQ ID NOS: 27 and 29 with corresponding non-cysteine-cyclized control peptides are presented as SEQ ID NOS: 28 and 30. The amino acid sequences of various known cytotoxic and/or pro-apoptosis peptides are presented as cysteine-cyclized peptides in SEQ ID NOS: 31 and 33 with corresponding non-cysteine-cyclized peptides are presented in SEQ ID NOS: 32, and 34.

The amino acid sequences of a peptide known as mPep is presented as cysteine-cyclized peptides in SEQ ID NO: 35 with corresponding non-cysteine-cyclized peptide presented in SEQ ID NO: 36.

DETAILED DESCRIPTION

Definitions

In this disclosure, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements and components comprising one unit and elements or components that comprise more than one unit unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

As used herein, and unless otherwise indicated, the term adipose associated disorders include but are not limited to disorders of white or brown adipose tissue, adipose associated body composition or body weight disorders including, but not limited to, disorders related to body weight, such as obesity, lypodystrophy, metabolic syndrome, and conditions associated with weight gain, maintenance of weight loss, risk of weight regain following weight loss, and related blood sugar disorders, diabetes, hypertension, fibrotic conditions, and cancer.

As used herein, and unless otherwise indicated, the terms "treat," "treating," "treatment" and "therapy" contemplate an action that occurs while a patient is suffering from a white adipose related disorder that reduces the severity of one or more symptoms or effects of an adipose associated body composition or body weight disorder, such as obesity, lypodystrophy, diabetes or metabolic syndrome, fibrosis, and cancer. Where the context allows, the terms "treat," "treating," and "treatment" also refers to actions taken toward ensuring that individuals at increased risk of a adipose associated body composition or body weight disorder, such as obesity, lypodystrophy, diabetes or metabolic syndrome, fibrosis and cancer are able to receive appropriate surgical and/or other medical intervention prior to onset of a adipose associated body composition or body weight disorder, such as obesity, lypodystrophy, diabetes or metabolic syndrome, fibrosis and cancer. As used herein, and unless otherwise indicated, the terms "prevent," "preventing," and "prevention" contemplate an action that occurs before a patient begins to suffer from an adipose associated body composition or body weight disorder, such as obesity, lypodystrophy, diabetes or metabolic syndrome, fibrosis and cancer, that delays the onset of, and/or inhibits or reduces the severity of, a adipose associated body composition or body weight disorder, such as obesity, lypodystrophy, diabetes or metabolic syndrome, fibrosis and cancer.

As used herein, and unless otherwise indicated, the terms "manage," "managing," and "management" encompass preventing, delaying, or reducing the severity of a recurrence of an adipose associated body composition or body weight disorder, such as obesity, lypodystrophy, diabetes or metabolic syndrome, fibrosis and cancer in a patient who has already suffered from such a disease, disorder or condition. The terms encompass modulating the threshold, development, and/or duration of the adipose associated body composition or body weight disorder, such as obesity, lypodystrophy, diabetes or metabolic syndrome, fibrosis and cancer or changing how a patient responds to the adipose associated body composition or body weight disorder.

As used herein, and unless otherwise specified, a "therapeutically effective amount" of a compound is an amount sufficient to provide any therapeutic benefit in the treatment or management adipose associated body composition or body weight disorder, such as obesity, lypodystrophy, diabetes or metabolic syndrome, fibrosis and cancer or to delay or minimize one or more symptoms associated with adipose associated body composition or body weight disorder, such as obesity, lypodystrophy, diabetes or metabolic syndrome, fibrosis and cancer. A therapeutically effective amount of a compound means an amount of the compound, alone or in combination with one or more other therapies and/or therapeutic agents that provide any therapeutic benefit in the treatment or management of adipose associated body composition or body weight disorder, such as obesity, lypodystrophy, diabetes or metabolic syndrome, fibrosis and cancer. The term "therapeutically effective amount" can encompass an amount that alleviates adipose associated body composition or body weight disorder, such as obesity, lypodystrophy, diabetes or metabolic syndrome, fibrosis and cancer, improves or reduces adipose associated body composition or body weight disorder, such as obesity, lypodystrophy, diabetes or metabolic syndrome, fibrosis and cancer, improves overall therapy, or enhances the therapeutic efficacy of another therapeutic agent.

As used herein, and unless otherwise specified, a "prophylactically effective amount" of a compound is an amount sufficient to prevent or delay the onset of adipose associated body composition or body weight disorder, such as obesity, lypodystrophy, diabetes or metabolic syndrome, fibrosis and cancer, or one or more symptoms associated adipose associated body composition or body weight disorder, such as obesity, lypodystrophy, diabetes or metabolic syndrome, fibrosis and cancer or prevent or delay its recurrence. A prophylactically effective amount of a compound means an amount of the compound, alone or in combination with one or more other treatment and/or prophylactic agent that provides a prophylactic benefit in the prevention of a adipose associated body composition or body weight disorder, such as obesity, lypodystrophy, diabetes or metabolic syndrome, fibrosis and cancer. The term "prophylactically effective amount" can encompass an amount that prevents adipose associated body composition or body weight disorder, such as obesity, lypodystrophy, diabetes or metabolic syndrome, fibrosis and cancer, improves overall prophylaxis, or enhances the prophylactic efficacy of another prophylactic agent. The "prophylactically effective amount" can be prescribed prior to, for example, the development of an adipose tissue associated disorder.

As used herein, "patient" or "subject" includes organisms which are capable of suffering from an adipose tissue associated body composition or body weight disorder, such as obesity, lypodystrophy, diabetes or metabolic syndrome, fibrosis and cancer as described herein, such as human and non-human mammals. Preferred human animals include human subjects. The term "non-human mammals" as used herein includes all mammals, e.g., rodents, mice, rats, etc. and non-human primates, companion animals and livestock, e.g., sheep, dog, cow, horse, etc.

As used herein, a "targeting peptide" is a peptide comprising a contiguous sequence of amino acids, which is characterized by selective localization to an organ, tissue or cell type. Selective localization may be determined, for example, by methods disclosed below, wherein the putative targeting peptide sequence is incorporated into a protein that is displayed on the outer surface of a phage. Administration to a subject of a library of such phage that have been genetically engineered to express a multitude of such targeting peptides of different amino acid sequence is followed by collection of one or more organs, tissues or cell types from the subject and identification of phage found in that organ, tissue or cell type. A phage expressing a targeting peptide sequence is considered to be selectively localized to a tissue or organ if it exhibits greater binding in that tissue or organ compared to a control tissue or organ. Preferably, selective localization of a targeting peptide should result in a two-fold or higher enrichment of the phage in the target organ, tissue or cell type, compared to a control organ, tissue or cell type. Selective localization resulting in at least a three-fold, four-fold, five-fold, six-fold, seven-fold, eight-fold, nine-fold, ten-fold or higher enrichment in the target organ compared to a control organ, tissue or cell type is more preferred. Alternatively, a phage expressing a targeting peptide sequence that exhibits selective localization preferably shows an increased enrichment in the target organ compared to a control organ when phage recovered from the target organ are re-injected into a second host for another round of screening. Further enrichment may be exhibited following a third round of screening. Another alternative means to determine selective localization is that phage expressing the putative target peptide preferably exhibit a two-fold, more preferably a three-fold or higher enrichment in the target organ compared to control phage that express a non-specific peptide or that have not been genetically engineered to express any putative target peptides. "Targeting peptide" and "homing peptide" are used synonymously herein.

As used herein "phage display library" means a collection of phage that have been genetically engineered to express a set of putative targeting peptides on their outer surface. In preferred embodiments, DNA sequences encoding the putative targeting peptides are inserted in frame into a gene encoding a phage capsule protein. In other preferred embodiments, the putative targeting peptide sequences are in part random mixtures of all twenty amino acids and in part non-random. In certain preferred embodiments the putative targeting peptides of the phage display library exhibit one or more cysteine residues at fixed locations within the targeting peptide sequence. Cysteines may be used, for example, to create a cyclic peptide.

A "macromolecular complex" refers to a collection of molecules that may be random, ordered or partially ordered in their arrangement. The term encompasses biological organisms such as bacteriophage, viruses, bacteria, unicellular pathogenic organisms, multicellular pathogenic organisms and prokaryotic or eukaryotic cells. The term also encompasses non-living assemblages of molecules, such as liposomes, microcapsules, microparticles, nanoparticles, magnetic beads and microdevices. The only requirement is that the complex contains more than one molecule. The molecules may be identical, or may differ from each other.

A "receptor" for a targeting peptide includes but is not limited to any molecule or macromolecular complex that binds to a targeting peptide. Non-limiting examples of receptors include peptides, proteins, glycoproteins, lipoproteins, epitopes, lipids, carbohydrates, multi-molecular structures, a specific conformation of one or more molecules and a morphoanatomic entity. In preferred embodiments, a "receptor" is a naturally occurring molecule or complex of molecules that is present on the lumenal surface of cells forming blood vessels within a target organ, tissue or cell type.

Compositions and methods are provided for use in generating selective targeting peptides. In some embodiments, particular targeting peptides selective or specific for adipose tissue, are provided, including, but not limited to, SEQ ID NOS: 13 AND 14, SEQ ID NO: 12, SEQ ID NO: 14, SEQ ID NO: 15, SEQ ID NO: 16, SEQ ID NO: 17, SEQ ID NO: 18 or SEQ ID NO: 19, and in still other embodiments, targeting peptides selective for adipose tissue may be used to selectively or specifically deliver therapeutic agents to target tissues, such as adipose tissue. In certain embodiments, the methods concern the preparation and identification of targeting peptides selective or specific for a given target cell, tissue, or organ, such as adipose. Adipose targeting peptides include, but are not limited to CKGGRAKDC (SEQ ID NO: 25, SEQ ID NO: 26, and SEQ ID NO: 1-16). Control peptides include, but are not limited to CARAC (SEQ ID NOS: 27 and 28), or CGDKAKGRC (SEQ ID NOS: 29 and 30).

White fat represents a unique tissue that, like tumors, can quickly proliferate and expand (Wasserman, In: Handbook of Physiology, eds. Renold and Cahill, pp. 87-100, American Physiological Society, Washington, D.C., 1965; Cinti, *Eat. Weight. Disord.* 5:132-142, 2000). Studies of adipose tissue reveal that it is highly vascularized. Multiple capillaries make contacts with every adipocyte, suggesting the importance of the vasculature for maintenance of the fat mass (Crandall et al., *Microcirculation* 4:211-232, 1997). Adipose tissue proliferation might rely on angiogenesis similarly to tumors. If so, destruction of fat neovasculature could prevent the development of obesity, whereas targeting existing adipose blood vessels could potentially result in fat regression. Methods of use of adipose targeting peptides may include induction of weight loss, treatment of obesity or other adipose associated disorders such as but not limited to, imaging or treatment of cancer and fibrosis.

Disclosed is the combination of phage display in vivo technology (such as that described in, among other places, US Patent Applications US20090104117, US20060094672, US20060239968, US20090221505, US20080176792, US20080124277, US20100172864, US20040170955, US20010046498 and Kolonin et al., *Nature Medicine;* 10, 625-32, 2004) with fluorescence-activated cell sorting (FACS) for isolation of peptides homing to selective populations of cells in an organ of interest. This in vivo selection system was used in combination with phage display libraries to identify organ, tissue or cell type-targeting peptides. Phage display libraries expressing transgenic peptides on the surface of bacteriophage can be generated by inserting random oligonucleotides into cDNAs encoding a phage surface protein, generating collections of phage particles displaying unique peptides in many permutations. Phage display is a technique in which a phage library expresses, for example, a set of random peptide sequences of defined length, incorporated into a phage coat protein and peptide sequences that bind to a target molecule, cell, tissue, for example adipose tissue or organ were identified by incubating a phage display library with the target and selecting for bound peptides Unbound phage is washed away and bound phage eluted and collected. The collected phage may be amplified and taken through further binding/amplification cycles to enrich the pool of peptides for those that selectively and/or specifically bind to the target. With each cycle, the proportion of phage in the pool that contains targeting peptides for the target of interest is enriched. After several cycles, individual phage clones may be characterized by DNA sequencing to identify the targeting peptide sequences (biopanning, see for example, US20050187161 as well as Pasqualini and Ruoslahti, *Nature* 380:364-66, 1996; Arap et al., Science 279:377-80, 1998).

Intravenous (I.V.) administration of phage display libraries to mice was followed by the recovery of phage from individual organs. Phage were recovered that were capable of selective homing to adipose tissue, based on the specific targeting peptide sequences expressed on the outer surface of the phage. A variety of organ and tumor-homing peptides have been identified by this method (see for example U.S. patent documents: US20060094672, US20080124277, US20090104117, US20090221505 and US20100172864).

The specific examples below provide a demonstration of the validity of such an approach when applied to white adipose (fat) tissue (WAT), however, those of skill in the art will realize that this technique could be applied to brown adipose tissue (BAT) and even to other cell types from various tissues and organs. WAT contains an abundant supply of pericytic adipose stromal cells (ASC), which belong to the class of mesenchymal stem cells (MSC). MSC have the CD34+CD31−CD45− cell surface signature. The multipotent nature of MSC and ASC, as well as their high rate of proliferation and migration ability mean that they can be both beneficial and pathogenic. ASC have been shown to be responsible for expansion of fat tissue in obesity but also to promote cancer progression and possibly other diseases accompanied by fibrosis (Zhang et al., Cancer Res. 69: 5259-5266, 2009).

To demonstrate the success of this combination of phage display in vivo technology and a FACS screening approach, peptide libraries for markers of ASC were screened in live mice. A mixture of random peptide libraries comprising cyclic $CX_7C$, $CX_8C$, and $CX_9C$ (wherein C represents cysteine and X represents any residue) were screened. The phage-peptide library was injected into an animal and 4 rounds of synchronous multi-organ in vivo biopanning are performed to enrich for WAT-homing peptides. In every selection round phage are I.V.-administered and recovered from the stromal/vascular fraction (SVF) of WAT and control organs, amplified, pooled, and used for the next round. FACS was used to deplete phage-peptides bound to endothelial ($CD31^+$) and hematopoietic ($CD45^+$) cells and to collect phage-peptides bound to $CD34^+CD31^-CD45^-$ ASC. Phage enrichment was demonstrated by the increased recovery of phage transforming units (TU) in every subsequent round reflects the selection of phage-peptides homing to $CD34^+$ $CD31^-CD45^-$ cells of WAT and of other target organs.

The result was that peptides that home to ASC when injected in vivo, but not to MSC, were identified using control organs included for counter-selection. Organs screened included lung, bone, bone marrow, and skeletal muscle. One particular peptide designated as WAT7 (sequence CSWKYWFGEC and SWKYWFGE: SEQ ID NOS: 13 and 14 respectively) showed the most definitive ASC-targeting pattern, whereas Peptide LU-2 (sequence C ESGFPTVGC: SEQ ID NOS: 19 and 20) was chosen as a control peptide that targets MSC in the lung.

Specificity of homing to $CD34^+CD31^-CD45^-$ cells of WAT for individual phage-peptide clones was demonstrated by injection into mice. The binding of phage bearing WAT-7 peptide was highly enriched on ASC as compared to the binding of lung MSC (see FIG. 1C). In contrast, α5β1-homing peptide mPep (Nie et al., 2008, ibid) and other control peptides tested did not display any WAT specificity.

WAT7, is a cyclic octapeptide (amino acid sequence C SWKYWFGEC and SWKYWFGE (SEQ ID NOS: 13 and 14) that homed to ASC, but not to MSC in other organs, when administered systemically. WAT7 may be cyclized via the terminal CYS moieties. WAT-7 was used as bait to biochemically purify the corresponding ASC surface receptor which was identified as a previously overlooked isoform of decorin (DCN) protein, a proteolytic cleavage fragment lacking glycosylation site. It was determined that this truncated DCN (termed delta-DCN (ΔDCN)), is overexpressed by ASC and is exposed on the cell surface, thus providing a new ASC marker. In addition by reversing the idea and screening for proteins that mimic WAT-7, resistin was identified as the endogenous ligand of ΔDCN in WAT. Ectopic expression of ΔDCN in preadipocytes induces a phenotype that is consistent with that was previously reported with resistin, supporting the conclusion that resistin-ΔDCN interaction controls signaling cascades that control the fate of ASC. The disclosed peptides can be injected systemically in order to deplete selective cell populations. In the examples below, peptides targeting adipose stem cells (ASC) in white adipose (fat) tissue (WAT) are detailed. ASC targeting can be beneficial as a therapy of obesity, cancer and fibrosis.

The use of peptides as targeting peptides and to generate for example in vivo cell targeting hybrid peptides coupled to pro-apoptotic hybrid peptides that exhibit selective and/or specific binding of target tissue including, but not limited to, adipose tissues have been previously reported (see for example US Patent Application Publications US20090104117, US20060094672, US20060239968, US20090221505, US20080176792, US20080124277 and US20100172864). Such hybrid peptides are synthesized peptides composed of two functional domains: a homing (cell targeting) domain that binds to a receptor differentially expressed on cells of interest and a cytotoxic domain that causes apoptotic death of cells that internalize the peptide. The homing peptide is typically 7 to 8 amino acids long and is cyclic (constrained by two disulfide-bonded cysteines). The cytotoxic domain is an amphipatic peptide sequence KLAKLAKKLAKLAK (SEQ ID NO: 31) designated $(KLAKLAK)_2$, which disrupts mitochondrial membranes upon receptor-mediated cell internalization and causes programmed cell death (apoptosis). Such cytotoxic peptides also include, those comprising those having the formula of (FXR)n, where n=4, 6, 8 and 10, and where F is phenylalanine, $F_X$ is cyclohexyl-alanine and Hex is 6-carbon alkyl chain residue, examples being $(KFAKFAK)_2$ (SEQ ID NO: 37), $(KF_XAKFXAK)_2$ (SEQ ID NO: 38) and $(KHexAKHexAK)_2$ (SEQ ID NO: 39) as well as those described, for example in, Horton, K L and Kelley, S O. Engineered Apoptosis-Inducing Peptides with Enhanced Mitochondrial Localization and Potency. J. Med. Chem. 52, 3293-3299, 2009; Yousif, L. F., Stewart, K. M., Horton, K. L. and Kelley, S. O. Mitochondria-Penetrating Peptides: Sequence Effects and Model Cargo Transport. ChemBioChem, 10: 2081-2088, 2009; Kelley S O, Stewart K M, Mourtada R. Development of novel peptides for mitochondrial drug delivery: amino acids featuring delocalized lipophilic cations. Pharm Res. November; 28(11):2808-19, 2011. Epub 2011 Aug. 11; Horton, K L, Pereiral, M P, Stewart, K M, Fonseca S B and Kelley, S O. Tuning the Activity of Mitochondria-Penetrating Peptides for Delivery or Disruption, ChemBioChem, 13(3), 476-485, 2012. Published online: 11 Jan. 2012.

However, the success of these hybrid peptides has been previously limited, and may be associated with toxicity, because the homing domain and the published Gly-Gly linker have traditionally been composed of L-amino acids which can be subject to proteolysis in vivo. Proteolysis reduces the active hybrid peptide and can eventually result in the release of various sub-peptides, some of which may represent the targeting or effector portions of the hybrid peptide. The possible release of the effector peptides, such as but not limited to pro-apoptotic peptides, such as $_DKLAK-LAK_2$, (SEQ ID NO: 31) without the targeting peptides, may lead to adverse reactions such as kidney toxicity. In addition, instability due to proteolysis, increases the amount of peptide necessary for injection to obtain therapeutic levels. Therefore, the clinical efficacy and safety of effector peptides of the prior art is limited.

Further, because the glycines composing the earlier described linker region do not exist as a D-form, synthesis of an all-D pro-apoptotic peptide was not been previously possible until the replacement of the linker with aminohexanoic acid, as described herein. In addition, construction of a homing/targeting peptide domain from D-form amino acids has not been previously attempted due to a concern that conversion from L-form (in which the peptides are originally isolated) to D-form may result in conformational change that results in incompatibility with the target receptor and loss of recognition, and a corresponding loss of homing. However, as described herein such all-D peptides can home to target cells as well as the L peptides of the prior art.

In some embodiments, a composition includes an isolated peptide comprising a amino acid sequence selected from the group consisting of SEQ ID NOS: 1-16, wherein the peptide binds to adipose tissue. In some embodiments, a protein composition comprises an amino acid sequence selected from the group consisting of SEQ ID NOS: 1-16, and in some embodiments, the protein composition is composed entirely of D-amino acids. In some other embodiments, a protein composition comprises a peptide coupled to an imaging agent. In some embodiments, the targeting peptide is coupled to cytotoxic or pro-apoptotic agent. In some embodiments, a protein composition comprises a peptide coupled to an agent that induces white adipose tissue to convert to brown adipose tissue. In some embodiments, the peptides are composed of D-amino acids. In some embodiments, the peptides are coupled to the agents or other peptides through a linker. In some embodiments the linker comprises aminohexanoic acid. In some embodiments the linker comprises $(CH_2)_4$; $(CH_2)_5$; $(CH_2)_6$; $(CH_2)_2$; $(CH_2)_8$ or a combination thereof. In some embodiments, the agent activates b3-adrenergic receptors on a white adipose tissue. In some embodiments, the agent is a peptide and in some embodiments, the peptide is composed of D-amino acids. In some embodiments, the peptides are composed of D-amino acids. In some embodiments, the peptides are coupled to the agents or other peptides through a linker. In some embodiments the linker comprises aminohexanoic acid.

In some other embodiments, an isolated nucleic acid composition comprises a nucleotide sequence that encodes an amino acid sequence selected from the group consisting of SEQ ID NOS: 1-16. In some embodiments, a recombinant host cell comprises the isolated nucleic acid molecule, and in some additional embodiments, an expression vector comprises the isolated nucleic acid molecule. In some embodiments, a host cell comprises the expression vector.

In some embodiments, a method of delivering a cytotoxic, apoptotic, transdevelopmental or imaging peptide to adipose tissue comprises (a) coupling to a targeting peptide having an amino acid sequence selected from the group consisting of SEQ ID NOS: 1-16, wherein the targeting peptide selectively binds an adipose cell. In some embodiments the peptides are composed of D-amino acids. In some embodiments, the peptides are coupled through a linker peptide and in some embodiments the linker comprises aminohexanoic acid.

In some other embodiments, a method of delivering a compound or agent to a adipose tissue comprises: a) obtaining a peptide that selectively binds to adipose tissue, wherein the peptide is less than 100 amino acids in length and includes an adipose tissue targeting motif having an amino acid sequence selected from the group consisting of SEQ ID NOS: 1-16, wherein the peptide is coupled to the compound or agent that one desires to target to adipose tissue; and b) exposing the peptide to a population of cells suspected of containing adipose tissue. In some embodiments, the peptide comprises a linker. In some embodiments the peptide is composed of D-amino acids. In some embodiments, both the peptide and the agent are composed of D-amino acids. In some embodiments, the coupling occurs through a linker peptide and in some embodiments the linker comprises aminohexanoic acid. In some embodiments, the agent comprises a cytotoxic or pro-apoptotic peptide. In some embodiments, the agent comprises is an imaging agent. In some embodiments, (b) comprises, exposing a subject to the peptide to treat an adipose associated disorder. In some embodiments the population of cells is in a human subject. In some embodiments, the population of cells is a thin section of a tissue. In other embodiments, the method further comprises detecting adipose stem cells in said population. In some embodiments, the adipose associated disorder is a body composition disorder, a body weight disorders, obesity, lypodystrophy, diabetes, metabolic syndrome, fibrosis or cancer.

In other embodiments, is an isolated peptide comprising a amino acid sequence selected from the group consisting of SEQ ID NOS: 17-24, and wherein said peptide binds to lung tissue. In some embodiments, a protein composition comprising an amino acid sequence selected from the group consisting of SEQ ID NOS: 17-24 and in some embodiments, the protein composition is composed entirely of D-amino acids. In other embodiments, is the protein composition wherein the peptide is coupled to an imaging agent. In some embodiments, the protein composition wherein the peptide is coupled to cytotoxic or pro-apoptotic agent. In some embodiments, the peptide is composed of D-amino acids. In some embodiments, the coupling occurs through a linker peptide and in some embodiments the linker comprises aminohexanoic acid.

In an exemplary composition of the chimeric cytotoxic peptide composition, all amino acids in both domains has been constructed of D-enantiomers, and thus resistant to proteolysis in vivo, allowing long-term effects of the peptide upon systemic administration. The linker connecting the two domains is aminohexanoic acid (Ahx): NH—$(CH_2)$5-CO, which is also not subject to cleavage by proteases in vivo. For use in the examples below, chimeric peptide was produced commercially (e.g. by Anaspec, Bachem, or Celtek) and synthesized by conventional peptide chemistry ("Merrifield synthesis").

The cytoxic activity of a WAT7-KLAKLAK$_2$ (SEQ ID NOS: 13-SEQ ID NO: 31) all-D-peptide synthesized by Celtek (Celtek Bioscience, Nashville, Tenn. 37210) was first demonstrated in vitro using trypan blue staining of both treated and untreated primary murine ASC cultures as described in the examples below. Using Apo-Trace (Sigma, St. Louis, USA) and flow cytometric analysis it was demonstrated that the WAT7 targeted pro-apoptotic peptide had indeed induced apoptosis and cell death in the treated ASC cells (see example 8 below). To demonstrate in vivo activity and efficacy of the WAT7-KLAKLAK$_2$ (SEQ ID NOS: 13-SEQ ID NO: 31) all-D-peptide, 2 mg of peptide was injected into mice and cell death was detected in WAT at 48 hrs after treatment with WAT7-KLAKLAK$_2$ (SEQ ID NOS: 13-SEQ ID NO: 31) all-D-peptide. No cell death was identified in kidney or in peripheral blood and no MTD was achieved even with increasing peptide doses (up to 100 mg/kg body weight). These findings clearly demonstrate the efficacy of targeting cytotoxic domains to adipose tissue using the targeting peptide identified using the disclosed methods and which have increased stability due to an all D amino acid composition. In some embodiments targeting peptides selective for angiogenic vasculature in adipose tissue could be used to treat obesity associated disorders, for example for weight reduction or for preventing weight gain. By attaching anti-angiogenic or toxic moieties to an adipose targeting peptide, the blood vessels supplying new fat tissue could be selectively inhibited, preventing the growth of new deposits of fat and potentially killing existing fat deposits. Because brown adipose tissue more vascularized, a vasculature based targeting approach would be very effective for delivery of therapeutic reagents to BAT for activation of this tissue.

In certain embodiments, alternative therapeutic agents may be attached to a targeting peptide or fusion protein for selective delivery to, for example, white adipose tissue. Agents or factors suitable for use may include any chemical compound that induces apoptosis, cell death, cell stasis and/or anti-angiogenesis. Apoptosis, or programmed cell death, is an essential process for normal embryonic development, maintaining homeostasis in adult tissues, and suppressing carcinogenesis. Examples of the coupling and use of such peptides include but are not limited to US Patent Applications US20090104117, US20060094672, US20060239968, US20090221505, US20080176792 and US20080124277. Non-limiting examples of pro-apoptosis agents contemplated within the scope of the disclosure include gramicidin, magainin, mellitin, defensin, cecropin, (KLAKLAK)$_2$ (SEQ ID NO: 31), (KLAKKLA)$_2$ (SEQ ID NO: 32), (KAAKKAA)$_2$ (SEQ ID NO: 33) or (KLGKKLG)$_3$ (SEQ ID NO: 34).

In certain embodiments included is the administration of targeting peptides attached to anti-angiogenic agents, such as angiotensin, laminin peptides, fibronectin peptides, plasminogen activator inhibitors, tissue metalloproteinase inhibitors, interferons, interleukin 12, platelet factor 4, IP-10, Gro-β, thrombospondin, 2-methoxyoestradiol, proliferin-related protein, carboxiamidotriazole, CM101, Marimastat, pentosan polysulphate, angiopoietin 2 (Regeneron), interferon-alpha, herbimycin A, PNU145156E, 16K prolactin fragment, Linomide, thalidomide, pentoxifylline, genistein, TNP470, endostatin, paclitaxel, accutin, angiostatin, cidofovir, vincristine, bleomycin, AGM-1470, platelet factor 4 or minocycline.

In certain embodiments administration of targeting peptides attached to cytotoxic agents. Such cytotoxic chemotherapeutic agents, include but at not limited to, 5-fluorouracil, bleomycin, busulfan, camptothecin, carboplatin, chlorambucil, cisplatin (CDDP), cyclophosphamide, dactinomycin, daunorubicin, doxorubicin, estrogen receptor binding agents, etoposide (VP16), farnesyl-protein transferase inhibitors, gemcitabine, ifosfamide, mechlorethamine, melphalan, mitomycin, navelbine, nitrosurea, plicomycin, procarbazine, raloxifene, tamoxifen, taxol, temazolomide (an aqueous form of DTIC), transplatinum, vinblastine and methotrexate, vincristine, or any analog or derivative variant of the foregoing. Most chemotherapeutic agents fall into the categories of alkylating agents, antimetabolites, antitumor antibiotics, corticosteroid hormones, mitotic inhibitors, and nitrosoureas, hormone agents, natural products, miscellaneous agents, and any analog or derivative variant thereof.

Natural products generally refer to compounds originally isolated from a natural source, and identified as having a pharmacological activity. Such compounds, analogs and derivatives thereof may be, isolated from a natural source, chemically synthesized or recombinantly produced by any technique known to those of skill in the art. Natural products include such categories as mitotic inhibitors, antitumor antibiotics, enzymes and biological response modifiers. Examples, of such natural products, include but are not limited to, plant alkaloids and other natural agents that can inhibit either protein synthesis required for cell division or mitosis, such as but not limited to docetaxel, etoposide (VP16), teniposide, paclitaxel, taxol, vinblastine, vincristine, and vinorelbine.

Chemotherapeutic agents and methods of administration, dosages, etc. are well known to those of skill in the art (see for example, the "Physicians Desk Reference", Goodman & Gilman's "The Pharmacological Basis of Therapeutics" and in "Remington's Pharmaceutical Sciences" 15$^{th}$ ed., pp 1035-1038 and 1570-1580, incorporated herein by reference in relevant parts), and may be combined with the disclosed compositions in light of the disclosures herein. Some variation in dosage will necessarily occur depending on the condition of the subject being treated. The person responsible for administration will, in any event, determine the appropriate dose for the individual subject. Examples of specific chemotherapeutic agents and dose regimes are also described herein. Of course, all of these dosages and agents described herein are exemplary rather than limiting, and other doses or agents may be used by a skilled artisan for a specific patient or application. Any dosage in-between these points, or range derivable therein is also expected to be included in certain embodiments.

In some embodiments, peptides that target WAT can be used to deliver compounds or agents that cause ASC cells to differentiate into BAT or to cause WAT to become BAT. ASCs can be differentiated into brown adipocytes with PPAR-gamma agonists (Elabd et al. Human multipotent adipose-derived stem cells differentiate into functional brown adipocytes. Stem Cells 27, 2753-2760, 2009). Therefore in some embodiments, compounds or agents which the PPAR-gamma pathway, such as, but not limited to, drugs of the thiazolidinedione class, for example rosiglitazone, can also be coupled to the described targeting peptides and used for modulatioin of adipogenesis in order to treat or prevent adipose associated body composition or body weight disorders, such as obesity, lypodystrophy, diabetes or metabolic syndrome, fibrosis and cancer.

White adipocytes have also been directly converted to a BAT-like phenotype both in culture and in vivo (Cinti. Transdifferentiation properties of adipocytes in the adipose organ. Am. *J. Physiol. Endocrinol. Metab.* 297, 977-986, 2009). This conversion is driven by sympathetic nervous system stimuli, such as cold temperature and signal transduction cascades triggered by activation of b3-adrenergic receptors in WAT. Therefore in some embodiments compounds or agents the activate adrenergic can be coupled to the described peptides to target WAT for conversion to BAT and thus used in order to treat or prevent adipose associated body composition or body weight disorders, such as obesity, lypodystrophy, diabetes or metabolic syndrome, fibrosis and cancer.

In some embodiments, disclosed peptides or proteins may be attached to imaging agents of use for imaging and diagnosis of various diseased organs, tissues or cell types. The peptide or protein is labeled or conjugated with a fluorophore or radiotracer for use as an imaging agent. Many appropriate imaging agents are known in the art, as are methods for their attachment to proteins or peptides using metal chelate complexes, radioisotopes, fluorescent markers, or enzymes whose presence can be detected using a colorimetric markers (such as, but not limited to, urease, alkaline phosphatase, (horseradish) hydrogen peroxidase and glucose oxidase).

In some embodiments, the imaging conjugate will also be dual labeled with a radioisotope in order to combine imaging through nuclear approaches and be made into a unique cyclic structure and optimized for binding affinity and pharmacokinetics. Such agents can be administered by any number of methods known to those of ordinary skill in the art including, but not limited to, oral administration, inhalation, subcutaneous (sub-q), intravenous (I.V.), intraperitoneal (I.P.), intramuscular (I.M.), or intrathecal injection, or as described in greater detail below. In some embodiments the methods and compositions described herein can be used alone or in combination with other techniques, to diagnose access and monitor and direct therapy of adipose associated disorders.

In some embodiments, targeting peptides can be used to direct the delivery of non-living assemblages of molecules, such as liposomes, microcapsules, microparticles, nanoparticles, magnetic beads and microdevices, alone or in combination, containing or coupled with antibiotics that have both antimicrobial and cytotoxic activity, including, but not limited to, bleomycin, dactinomycin, daunorubicin, doxorubicin (Adriamycin), plicamycin (mithramycin) and idarubicin. Additional types of cytotoxic agents that could be delivered using the disclosed targeting peptides include, but are not limited to, platinum coordination complexes, anthracenediones, substituted ureas, methyl hydrazine derivatives, amsacrine, L-asparaginase, and tretinoin. Platinum coordination complexes include such compounds as carboplatin and cisplatin (cis-DDP). An exemplary anthracenedione is mitoxantrone. An exemplary substituted urea is hydroxyurea. An exemplary methyl hydrazine derivative is procarbazine (N-methylhydrazine, MIH). These examples are not limiting and it is contemplated that any known cytotoxic, cytostatic or cytocidal agent may be attached to the presently disclosed targeting peptides and administered to a targeted organ, tissue or cell type. The desired targeting, cytotoxic or hybrid peptide amino acid sequences that can be used in various embodiments including the amino acid sequences described herein, as well as analogues and derivatives thereof. In fact, in some embodiments the any desired peptide amino acid sequences encoded by particular nucleotide sequences can be used, as is the use of any polynucleotide sequences encoding all, or any portion, of desired peptide amino acid sequences. The degenerate nature of the genetic code is well-known, and, accordingly, each targeting, cytotoxic or hybrid peptide amino acid-encoding nucleotide sequence is generically representative of the well-known nucleic acid "triplet" codon, or in many cases codons, that can encode the amino acid. As such, as contemplated herein, the targeting, cytotoxic or hybrid peptide amino acid sequences described herein, when taken together with the genetic code (see, e.g., "Molecular Cell Biology", Table 4-1 at page 109 (Darnell et al., eds., W. H. Freeman & Company, New York, N.Y., 1986)), are generically representative of all the various permutations and combinations of nucleic acid sequences that can encode such amino acid sequences.

Such functionally equivalent targeting, cytotoxic, imaging or hybrid peptide amino acid sequences include, but are not limited to, additions or substitutions of amino acid residues within the amino acid sequences encoded by a nucleotide sequence, but that result in a silent change, thus producing a functionally equivalent gene product. Amino acid substitutions may be made on the basis of similarity in polarity, charge, solubility, hydrophobicity, hydrophilicity, and/or the amphipathic nature of the residues involved. For example: nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

Amino acid substitutions may alternatively be made on the basis of the hydropathic index of amino acids. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). The use of the hydropathic amino acid index in conferring interactive biological function on a protein is understood in the art (Kyte and Doolittle, *J. Mol. Biol.* 157:105-132, 1982). It is known that in certain instances, certain amino acids may be substituted for other amino acids having a similar hydropathic index or score and still retain a similar biological activity. In making changes based upon the hydropathic index, in certain embodiments the substitution of amino acids whose hydropathic indices are within ±2 is included, while in other embodiments amino acid substitutions that are within ±1 are included, and in yet other embodiments amino acid substitutions within ±0.5 are included.

Amino acid substitutions may alternatively be made on the basis of hydrophilicity, particularly where the biologically functional protein or peptide thereby created is intended for use in immunological embodiments. In certain embodiments, the greatest local average hydrophilicity of a protein, as governed by the hydrophilicity of its adjacent amino acids, correlates with its immunogenicity and antigenicity, i.e., with a biological property of the protein. The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments the substitution of amino acids whose hydrophilicity values are within ±2 is included, in certain embodiments those that are within ±1 are included, and in certain embodiments those within ±0.5 are included. One may also identify epitopes from primary amino acid sequences on the basis of hydrophilicity.

The use of fusion proteins in which a full-length polypeptide or peptide, or a truncated or mutant version of peptide is fused to an unrelated protein, polypeptide, or peptide, and can be designed on the basis of the desired peptide encoding nucleic acid and/or amino acid sequences described herein. Such fusion proteins include, but are not limited to: IgFc fusions, which stabilize proteins or peptides and prolong half-life in vivo; fusions to any amino acid sequence that allows the fusion protein to be anchored to the cell membrane; or fusions to an enzyme, fluorescent protein, or luminescent protein that provides a marker function.

In some embodiments targeting peptide might be attached to a liposome or lipid complex based delivery system. Examples of such technologies are described in "Liposomes: A Practical Approach" (Torchilin and Weissig, eds., Oxford University Press, Oxford, United Kingdom, 2003), and in U.S. Pat. Nos. 4,594,595, 5,459,127, 5,948,767 and 6,110,490.

In certain embodiments, a fusion protein may be readily purified by utilizing an antibody that selectively binds to the fusion protein being expressed. In alternate embodiments, a fusion protein may be purified by subcloning peptide encoding nucleic acid sequence into a recombination plasmid, or a portion thereof, is translationally fused to an amino-terminal (N-terminal) or carboxy-terminal (C-terminal) tag consisting of six histidine residues (a "His-tag"; see, e.g., Janknecht et al., *Proc. Natl. Acad. Sci. USA* 88:8972-8976, 1991). Extracts from cells expressing such a construct are loaded onto $Ni^{2+}$ nitriloacetic acid-agarose columns, and histidine-tagged proteins are selectively eluted with imidazole-containing buffers.

While the desired peptide amino acid sequences described can be chemically synthesized (see, e.g., "Proteins: Structures and Molecular Principles" (Creighton, ed., W. H. Freeman & Company, New York, N.Y., 1984)), large polypeptides sequences may advantageously be produced by recombinant DNA technology using techniques well-known in the art for expressing nucleic acids containing a nucleic acid sequence that encodes the desired peptide. Such methods can be used to construct expression vectors containing peptide encoding nucleotide sequences and appropriate transcriptional and translational control signals. These methods include, for example, in vitro recombinant DNA techniques, synthetic techniques, and in vivo genetic recombination (see, e.g., "Molecular Cloning, A Laboratory Manual", supra, and "Current Protocols in Molecular Biology", supra). Alternatively, RNA and/or DNA encoding desired peptide encoding nucleotide sequences may be chemically synthesized using, for example, synthesizers (see, e.g., "Oligonucleotide Synthesis: A Practical Approach" (Gait, ed., IRL Press, Oxford, United Kingdom, 1984)).

A variety of host-expression vector systems may be utilized to express peptide encoding nucleotide sequences. When the desired peptide or polypeptide is soluble, or a soluble derivative, the peptide or polypeptide can be recovered from the host cell culture, i.e., from the host cell in cases where the peptide or polypeptide is not secreted, and from the culture media in cases where the peptide or polypeptide is secreted by the host cell. However, suitable expression systems also encompass engineered host cells that express the desired polypeptide, peptide or functional equivalents anchored in the cell membrane. Purification or enrichment of the desired peptide from such expression systems can be accomplished using appropriate detergents and lipid micelles, and methods well-known to those skilled in the art. Furthermore, such engineered host cells themselves may be used in situations where it is desired not only to retain the structural and functional characteristics of the peptide, but to assess biological activity, e.g., in certain drug screening assays.

In certain applications, transient expression systems are desired. However, for long-term, high-yield production of recombinant proteins or peptides, stable expression is generally preferred. For example, cell lines that stably express the desired protein, polypeptide, peptide, or fusion protein may be engineered. Rather than using expression vectors that contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells are allowed to grow for about 1-2 days in an enriched media, and then switched to a selective media. The selectable marker in the recombinant plasmid confers resistance to the selection, and allows cells to stably integrate the plasmid into their chromosomes and grow to form foci, which in turn can be cloned and expanded into cell lines. This method may advantageously be used to engineer cell lines that express the desired gene products or portions thereof. Such engineered cell lines may be particularly useful in screening and evaluation of compounds that affect the endogenous activity of the desired protein, polypeptide or peptide.

A number of selection systems may be used, including, but not limited to, the herpes simplex virus thymidine kinase (Wigler et al., *Cell* 11:223-232, 1977), hypoxanthine-guanine phosphoribosyltransferase (Szybalska and Szybalski, *Proc. Natl. Acad. Sci. USA* 48:2026-2034, 1962), and adenine phosphoribosyltransferase (Lowy et al., *Cell* 22:817-823, 1980) genes, which can be employed in $tk^-$, $hgprt^-$ or $aprt^-$ cells, respectively. Anti-metabolite resistance can also be used as the basis of selection for the following genes: dihydrofolate reductase (dhfr), which confers resistance to methotrexate (Wigler et al., *Proc. Natl. Acad. Sci. USA* 77:3567-3570, 1980, and O'Hare et al., *Proc. Natl. Acad. Sci. USA* 78:1527-1531, 1981); guanine phosphoribosyl transferase (gpt), which confers resistance to mycophenolic acid (Mulligan and Berg, *Proc. Natl. Acad. Sci. USA* 78:2072-2076, 1981); neomycin phosphotransferase (neo), which confers resistance to the aminoglycoside G-418 (Colbere-Garapin et al., *J. Mol. Biol.* 150:1-14, 1981); and hygromycin B phosphotransferase (hpt), which confers resistance to hygromycin (Santerre et al., *Gene* 30:147-156, 1984).

Host cells/expression systems that may be used for purpose of providing compostions to be used in the disclosed methods include, but are not limited to, microorganisms such as bacteria (e.g., *E. coli, B. subtilis*) transformed with a recombinant bacteriophage DNA, plasmid DNA, or cosmid DNA expression vector containing a desired peptide encoding nucleotide sequence; yeast (e.g., *Saccharomyces cerevisiae, Pichia pastoris*) transformed with a recombinant yeast expression vector containing a desired peptide encoding nucleotide sequence; insect cell systems infected with a recombinant virus expression vector (e.g., baculovirus) containing a desired peptide encoding nucleotide sequence; plant cell systems infected with a recombinant virus expression vector (e.g., cauliflower mosaic virus, CaMV; tobacco mosaic virus, TMV), or transformed with a recombinant plasmid expression vector (e.g., Ti plasmid), containing a desired peptide encoding nucleotide sequence; or mammalian cell systems (e.g., COS, CHO, BHK, 293, 3T3) harboring a recombinant expression construct containing a desired peptide encoding nucleotide sequence and a promoter derived from the genome of mammalian cells (e.g., metallothionein promoter) or from mammalian viruses (e.g., the adenovirus late promoter, the vaccinia virus 7.5K promoter).

In bacterial systems, a number of different expression vectors may be advantageously selected depending upon the use intended for the desired gene product being expressed. For example, when a large quantity of such a protein is to be produced, such as for the generation of pharmaceutical compositions comprising a desired peptide, or for raising antibodies to the protein, vectors that direct the expression of high levels of fusion protein products that are readily purified may be desirable. Such vectors include, but are not limited to: the *E. coli* expression vector pUR278 (Ruther and Müller-Hill, *EMBO J.* 2:1791-1794, 1983), in which a desired peptide encoding sequence may be ligated individually into the vector in frame with the lacZ coding region so that a fusion protein is produced; pIN vectors (Inouye and Inouye, *Nucleic Acids Res.* 13:3101-3110, 1985, and Van Heeke and Schuster, *J. Biol. Chem.* 264:5503-5509, 1989); and the like. pGEX vectors (GE Healthcare, Piscataway, N.J.) may also be used to express a desired peptide moiety as a fusion protein with glutathione S-transferase (GST). In general, such fusion proteins are soluble and can easily be purified from lysed cells by adsorption to glutathione-agarose beads, followed by elution in the presence of free glutathione. The pGEX vectors are designed to include thrombin or factor Xa protease cleavage sites so that the cloned desired peptide encoding gene product can be released from the GST moiety. Because, in some embodiments, D-amino acids are preferred, methods such as those described in, among others, Park, et al., (Production of D-amino acid using whole cells of recombinant *Escherichia coli* with separately and coexpressed D-hydantoinase and N-carbamoylase. *Biotechnol Prog.* July-August; 16(4):564-70, 2000).

In an exemplary insect system, *Autographa californica* nuclear polyhedrosis virus (AcNPV) is used as a vector to express a desired peptide encoding sequence. The virus grows in *Spodoptera frugiperda* cells. A desired peptide encoding sequence may be cloned individually into a non-essential region (for example the polyhedrin gene) of the virus, and placed under control of an AcNPV promoter (for example the polyhedrin promoter). Successful insertion of a desired peptide encoding sequence will result in inactivation of the polyhedrin gene and production of non-occluded recombinant virus (i.e., virus lacking the proteinaceous coat coded for by the polyhedrin gene). The recombinant viruses are then used to infect *Spodoptera frugiperda* cells in which the inserted polynucleotide is expressed (see, e.g., Smith et al., *J. Virol.* 46:584-593, 1983, and U.S. Pat. No. 4,215,051).

In mammalian host cells, a number of viral-based expression systems may be utilized. In cases where an adenovirus is used as an expression vector, a desired peptide encoding nucleotide sequence may be ligated to an adenovirus transcription/translation control complex, e.g., the late promoter and tripartite leader sequence. This chimeric sequence may then be inserted in the adenovirus genome by in vitro or in vivo recombination. Insertion in a non-essential region of the viral genome (e.g., region E1 or E3) will result in a recombinant virus that is viable and capable of expressing desired peptide products in infected hosts (see, e.g., Logan and Shenk, *Proc. Natl. Acad. Sci. USA* 81:3655-3659, 1984). Specific initiation signals may also be required for efficient translation of inserted desired peptide encoding nucleotide sequences. These signals include the ATG initiation codon and adjacent sequences. In some cases exogenous translational control signals, including, perhaps, the ATG initiation codon, may be provided. Furthermore, the initiation codon should be in phase with the reading frame of the desired peptide encoding coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Nevins, *CRC Crit. Rev. Biochem.* 19:307-322, 1986).

In yeast, a number of vectors containing constitutive or inducible promoters may be used. For a review, see, e.g., "Current Protocols in Molecular Biology", supra, Ch. 13, Bitter et al., *Meth. Enzymol.* 153:516-544, 1987, "DNA Cloning", Vol. II, Ch. 3 (Glover, ed., IRL Press, Washington, D.C., 1986); Bitter, *Meth. Enzymol.* 152:673-684, 1987, "The Molecular Biology of the Yeast *Saccharomyces*: Life Cycle and Inheritance" (Strathern et al., eds., Cold Spring Harbor Press, Cold Spring Harbor, N.Y., 1981), and "The Molecular Biology of the Yeast *Saccharomyces*: Metabolism and Gene Expression" (Strathern et al., eds., Cold Spring Harbor Press, Cold Spring Harbor, N.Y., 1982).

In plants, a variety of different plant expression vectors can be used, and expression of a desired peptide encoding sequence may be driven by any of a number of promoters. For example, viral promoters such as the 35S RNA or 19S RNA promoters of CaMV (Brisson et al., *Nature* 310:511-514, 1984), or the coat protein promoter of TMV (Takamatsu et al., *EMBO J.* 6:307-311, 1987) may be used. Alternatively, plant promoters such as the promoter of the small subunit of RUBISCO (Coruzzi et al., *EMBO J.* 3:1671-1679, 1984, and Broglie et al., *Science* 224:838-843, 1984), or heat shock promoters, e.g., soybean hsp17.5-E or hsp17.3-B (Gurley et al., *Mol. Cell. Biol.* 6:559-565, 1986) may be used. These constructs can be introduced into plant cells using, for example, Ti plasmids, Ri plasmids, plant virus vectors, direct DNA transformation, microinjection, or electroporation. For reviews of such techniques, see, e.g., Weissbach and Weissbach, in "Methods in Plant Molecular Biology", Section VIII (Schuler and Zielinski, eds., Academic Press, Inc., New York, N.Y., 1988), and "Plant Molecular Biology", $2^{nd}$ Ed., Ch. 7-9 (Grierson and Covey, eds., Blackie & Son, Ltd., Glasgow, Scotland, United Kingdom, 1988).

In addition, a host cell strain may be chosen that modulates the expression of the inserted desired peptide encoding sequence, or modifies and processes the desired peptide encoding nucleic acid sequence in a desired fashion. Such modifications (e.g., glycosylation) and processing (e.g., cleavage) of protein products may affect certain functions of the protein. Different host cells have characteristic and specific mechanisms for post-translational processing and modification of proteins and peptides. Appropriate cell lines or host systems can be chosen to ensure the correct or desired modification and processing of the desired protein, polypeptide, or peptide expressed. To this end, eukaryotic host cells that possess the cellular machinery for desired processing of the primary transcript, and glycosylation and/or phosphorylation of desired peptide encoding nucleic acid sequence be used. Such mammalian host cells include, but are not limited to, Chinese hamster ovary (CHO), VERO, baby hamster kidney (BHK), HeLa, monkey kidney (COS), MDCK, 293, 3T3, WI38, human hepatocellular carcinoma (e.g., Hep G2), and U937 cells.

In certain embodiments the presently disclosed compositions and are used in the treatment of adipose associated body composition or body weight disorders such as obesity, lypodystrophy, diabetes or metabolic syndrome, fibrosis and cancer.

In certain embodiments the presently disclosed compositions can be administered in combination with one or more additional compounds or agents ("additional active agents") for the treatment, management, and/or prevention of adipose associated body composition or body weight disorders such as obesity, lypodystrophy, diabetes or metabolic syndrome, fibrosis and cancer. Such therapies can be administered to a patient at therapeutically effective doses to treat or ameliorate adipose associated body composition or body weight disorders such as obesity, lypodystrophy, diabetes or metabolic syndrome, fibrosis and cancer. A therapeutically effective dose refers to that amount of the compound sufficient to result in any delay in onset, amelioration, or retardation of disease symptoms.

In some embodiments, are isolated peptides comprising an amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15 or SEQ ID NO: 16, and wherein said peptide binds to stromal cells in vivo. In some embodiments, the stromal cells are located in adipose tissue, fibrotic lesions or tumors.

In some embodiments are protein compositions comprising a peptide having the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15 or SEQ ID NO: 16. In some embodiments the peptides or protein compositions are composed entirely of D-amino acids. In some embodiments the peptides or protein compositions are coupled to an imaging agent. In some embodiments the peptides or protein compositions are coupled to cytotoxic or pro-apoptotic agent. In some embodiments the peptides or protein compositions are coupled to an agent that induces a white adipose tissue to convert to a brown adipose tissue. In some embodiments the peptides or protein compositions are coupled to an agent that activates b3-adrenergic receptors in white adipose tissue. In some embodiments the agents are peptides composed of D-amino acids. In some embodiments the peptides are coupled through a linker and in some embodiments the linker comprises aminohexanoic acid.

In other embodiments, are isolated peptides comprising an amino acid sequence of SEQ ID NO: 17, SEQ ID NO: 18, SEQ ID NO: 19, SEQ ID NO: 20, SEQ ID NO: 21, SEQ ID NO: 22, SEQ ID NO:23 or SEQ ID NO: 24, and wherein said peptide binds to stromal cells in vivo. In some embodiments, the stromal cells are located in lung tissue, fibrotic lesions or tumors.

In some embodiments are protein compositions comprising a peptide having the amino acid sequence of SEQ ID NO: 17, SEQ ID NO: 18, SEQ ID NO: 19, SEQ ID NO: 20, SEQ ID NO: 21, SEQ ID NO: 22, SEQ ID NO:23 or SEQ ID NO: 24. In some embodiments the peptides or protein compositions are composed entirely of D-amino acids. In some embodiments the peptides or protein compositions are coupled to an imaging agent. In some embodiments the peptides or protein compositions are coupled to cytotoxic or pro-apoptotic agent. In some embodiments the agents are peptides composed of D-amino acids. In some embodiments the peptides are coupled through a linker and in some embodiments the linker comprises aminohexanoic acid.

In some embodiments the protein compositions are composed entirely of D-amino acids and comprise a peptide having the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15 or SEQ ID NO: 16, and wherein the composition binds to stromal cells located in for example adipose tissue, fibrotic tissue or tumor tissue in vivo. In some embodiments, the peptide is coupled to an imaging agent, a cytotoxic, a pro-apoptotic agent. In some embodiments, the peptide is coupled to an agent that induces a white adipose tissue to convert to a brown adipose tissue, such as but not limited to, an agent activates b3-adrenergic receptors in white adipose tissue.

In some embodiments are isolated nucleic acid molecules comprising a nucleotide sequence that encodes an amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15 or SEQ ID NO: 16. In some embodiments, are expression vectors comprising these nucleic acid molecules and host cells comprising the expression vectors.

In some embodiments are methods of delivering a cytotoxic, pro-apoptosis, transdevelopmental or imaging peptide to adipose tissue, said methods comprising: (a) coupling a cytotoxic, pro-apoptosis, transdevelopmental or imaging peptide to a targeting peptide having an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15 or SEQ ID NO: 16; and (b) selectively binding the coupled targeting peptide to an adipose cell. In some embodiments the peptides are composed of D-amino acids. In some embodiments the peptides are coupled through a linker and in some embodiments the linker comprises aminohexanoic acid.

In other embodiments, are methods of delivering a compound or agent to an adipose tissue comprising: exposing a compound or agent-coupled peptide to a population of cells suspected of containing adipose tissue, wherein said compound- or agent-coupled peptide comprises the compound or agent coupled to a peptide that selectively binds to adipose tissue, wherein the peptide is less than 100 amino acids in length and includes an adipose tissue targeting motif having an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15 or SEQ ID NO: 16. In some embodiments the peptides are composed of D-amino acids. In some embodiments the peptides are coupled through a linker and in some embodiments the linker comprises aminohexanoic acid. In some embodiments, both the peptide and the agent are composed of D-amino acids. In some embodiments, the agent comprises a cytotoxic or pro-apoptotic peptide. In some embodiments, the peptide is composed of D-amino acids. In some embodiments, the agent comprises a imaging agent. In some embodiments exposing comprises, exposing a subject to the peptide that may be coupled to an agent, to treat an adiposity-associated disorder such as, but not limited to, obesity, fibrosis or cancer. In some embodiments the population of cells are from or in a human subject. In some embodiments the population of cells are from or in a veterinary subject.

In some embodiments the cells are in a population of cells ex vivo as is a thin section of a tissue. In some embodiments are methods of detecting adipose stromal cells in a heterogeneous cell population based on said selective binding of the compound- or agent-coupled peptide to said adipose tissue. In some embodiments are methods of detecting adipose stromal cells as identifying a patient who would benefit from treatment with a peptide targeted peptide is coupled to a compound- or agent such as, but not limited to a cytotoxic or pro-apoptotic agent. Examples of patients include human or veterinary patients suffering from a body composition disorder, a body weight disorder, obesity, lypodystrophy, diabetes, metabolic syndrome, fibrosis or cancer.

Specific details are provided with regards to the isolation and characterization of WAT7 peptide (SEQ ID NOS: 13 AND 14), but also provided are additional WAT targeting (SEQ ID NOS: 1-16) and lung targeting peptides (SEQ ID NOS: 17-24) which demonstrate the generic applicability of the disclosed methods.

Toxicity and therapeutic efficacy of such compositions can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, expressed as the ratio $LD_{50}/ED_{50}$. Compositions that exhibit large therapeutic indices are preferred. Compounds that exhibit toxic side effects may be used in certain embodiments, however, care should usually be taken to design delivery systems that target such compositions preferentially to the site of affected tissue, in order to minimize potential damage to uninfected cells and, thereby, reduce side effects.

Data obtained from cell culture assays and animal studies can be used in formulating a range of dosages for use in humans. The dosages of such compositions lie preferably within a range of circulating concentrations that include the $ED_{50}$ with little or no toxicity. The dosage may vary within this range depending on the dosage form employed and the route of administration utilized. For any composition, the therapeutically effective dose can be estimated initially from cell culture assays. A dose may be formulated in animal models to achieve a circulating plasma concentration range that includes the $IC_{50}$ (i.e., the concentration of the test composition that achieves a half-maximal inhibition of symptoms) as determined in cell culture. Such information can be used to more accurately determine useful doses in humans. Plasma levels may be measured, for example, by high performance liquid chromatography.

When the therapeutic treatment of adipose associated body composition or body weight disorders such as obesity, lypodystrophy, diabetes or metabolic syndrome, fibrosis and cancer is contemplated, the appropriate dosage may also be determined using animal studies to determine the maximal tolerable dose, or MTD, of a bioactive agent per kilogram weight of the test subject. In general, at least one animal species tested is mammalian. Those skilled in the art regularly extrapolate doses for efficacy and avoiding toxicity to other species, including human. Before human studies of efficacy are undertaken, Phase I clinical studies help establish safe doses.

Additionally, the bioactive agent may be coupled or complexed with a variety of well established compositions or structures that, for instance, enhance the stability of the bioactive agent, or otherwise enhance its pharmacological properties (e.g., increase in vivo half-life, reduce toxicity, etc.).

Such therapeutic agents can be administered by any number of methods known to those of ordinary skill in the art including, but not limited to, inhalation, subcutaneous (sub-q), intravenous (I.V.), intraperitoneal (I.P.), intramuscular (I.M.), or intrathecal injection, or topically applied (transderm, ointments, creams, salves, eye drops, and the like), as described in greater detail below.

Pharmaceutical compositions for use in accordance with the presently described compositions may be formulated in conventional manners using one or more physiologically acceptable carriers or excipients.

The pharmaceutical compositions can comprise formulation materials for modifying, maintaining, or preserving, for example, the pH, osmolarity, viscosity, clarity, color, isotonicity, odor, sterility, stability, rate of dissolution or release, adsorption or penetration of the composition. Suitable formulation materials include, but are not limited to amino acids (for example, glycine, glutamine, asparagine, arginine and lysine); antimicrobials; antioxidants (for example, ascorbic acid, sodium sulfite and sodium hydrogen-sulfite); buffers (for example, borate, bicarbonate, Tris-HCl, citrates, phosphates and other organic acids); bulking agents (for example, mannitol and glycine); chelating agents (for example, ethylenediamine tetraacetic acid (EDTA)); complexing agents (for example, caffeine, polyvinylpyrrolidone, beta-cyclodextrin, and hydroxypropyl-beta-cyclodextrin); fillers; monosaccharides, disaccharides, and other carbohydrates (for example, glucose, mannose and dextrins); proteins (for example, serum albumin, gelatin and immunoglobulins); coloring, flavoring, and diluting agents; emulsifying agents; hydrophilic polymers (for example, polyvinylpyrrolidone); low molecular weight peptides; salt-forming counterions (for example, sodium); preservatives (for example, benzalkonium chloride, benzoic acid, salicylic acid, thimerosal, phenethyl alcohol, methylparaben, propylparaben, chlorhexidine, sorbic acid and hydrogen peroxide); solvents (for example, glycerin, propylene glycol and polyethylene glycol); sugar alcohols (for example, mannitol and sorbitol); suspending agents; surfactants or wetting agents (for example, pluronics, PEG, sorbitan esters, polysorbates (for example, polysorbate 20 and polysorbate 80), triton, tromethamine, lecithin, cholesterol, and tyloxapal); stability enhancing agents (for example, sucrose and sorbitol); tonicity enhancing agents (for example, alkali metal halides (for example, sodium or potassium chloride), mannitol, and sorbitol); delivery vehicles; diluents; excipients; and pharmaceutical adjuvants ("Remington's Pharmaceutical Sciences", $18^{th}$ Ed. (Gennaro, ed., Mack Publishing Company, Easton, Pa., 1990)).

Additionally, the described therapeutic peptides can be linked to a half-life extending vehicle. Certain exemplary half-life extending vehicles are known in the art, and include, but are not limited to, the Fc domain, polyethylene glycol, and dextran (see, e.g., PCT Patent Application Publication No. WO 99/25044).

These agents may be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The agents may also be formulated as compositions for rectal administration such as suppositories or retention enemas, e.g., containing conventional suppository bases such as cocoa butter or other glycerides.

In addition to the formulations described previously, the agents may also be formulated as a depot preparation. Such long acting formulations may be administered by implantation (for example subcutaneously or intramuscularly) or by intramuscular injection. For example, agents may be formulated with suitable polymeric or hydrophobic materials (for example as an emulsion in an acceptable oil), ion exchange resins, or as sparingly soluble derivatives, for example, as a sparingly soluble salt. The compositions may, if desired, be presented in a pack or dispenser device, which may contain one or more unit dosage forms containing the active ingredient. The pack may for example comprise metal or plastic foil, such as a blister pack. The pack or dispenser device may be accompanied by instructions for administration.

Active compositions can be administered by controlled release means or by delivery devices that are well-known to those of ordinary skill in the art. Examples include, but are not limited to, those described in U.S. Pat. Nos. 3,845,770, 3,916,899, 3,536,809, 3,598,123, 4,008,719, 5,674,533, 5,059,595, 5,591,767, 5,120,548, 5,073,543, 5,639,476, 5,354,556, and 5,733,566. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof, to provide the desired release profile in varying proportions. Exemplary sustained release matrices include, but are not limited to, polyesters, hydrogels, polylactides (see, e.g., U.S. Pat. No. 3,773,919 and European Patent Application Publication No. EP 058,481), copolymers of L-glutamic acid and gamma ethyl-L-glutamate (see, e.g., Sidman et al., *Biopolymers* 22:547-556, 1983), poly (2-hydroxyethyl-methacrylate) (see, e.g., Langer et al., *J. Biomed. Mater. Res.* 15:167-277, 1981, and Langer, *Chemtech* 12:98-105, 1982), ethylene vinyl acetate (Langer et al., supra), and poly-D(−)-3-hydroxybutyric acid (European Patent Application Publication No. EP 133,988). Sustained release compositions may include liposomes, which can be prepared by any of several methods known in the art (see, e.g., Eppstein et al., *Proc. Natl. Acad. Sci. USA* 82:3688-3692, 1985, and European Patent Application Publication Nos. EP 036,676, EP 088, 046, and EP 143,949). Suitable controlled-release formulations known to those of ordinary skill in the art, including those described herein, can be readily selected for use with the presently disclosed compositions. Certain embodiments encompass single unit dosage forms suitable for oral administration such as, but not limited to, tablets, capsules, gelcaps, and caplets that are adapted for controlled-release.

All controlled-release pharmaceutical products have a common goal of improving therapy over that achieved by their non-controlled counterparts. Ideally, use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of active ingredient that promptly produces the desired therapeutic effect, and gradually and continually release other amounts of active ingredient to maintain this level of therapeutic or prophylactic effect over an extended period of time. In order to maintain this relatively constant level of active ingredient in the body, the drug must be released from the dosage form at a rate that will replace the amount of active ingredient being metabolized and excreted from the body. Controlled-release of an active ingredient can be stimulated by various conditions including, but not limited to, pH, temperature, enzymes, water, or other physiological conditions or compositions.

In some cases, active ingredients of the disclosed methods and compositions are preferably not administered to a patient at the same time or by the same route of administration. Therefore, in some embodiments are kits that, when used by the medical practitioner, can simplify the administration of appropriate amounts of active ingredients to a patient.

A typical kit comprises a single unit dosage form of one or more of the therapeutic agents disclosed, alone or in combination with a single unit dosage form of another agent that may be used in combination with the disclosed compositions. Disclosed kits can further comprise devices that are used to administer the active ingredients. Examples of such devices include, but are not limited to, syringes, drip bags, patches, and inhalers.

Disclosed kits can further comprise pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate. However, in specific embodiments, the disclosed formulations do not contain any alcohols or other co-solvents, oils or proteins.

The following section provides further details regarding examples of various embodiments. It should be appreciated by those of skill in the art that the techniques disclosed in the examples that follow represent techniques and/or compositions discovered by the inventor to function well. However, those of skill in the art should, in light of the disclosure, appreciate that many changes can be made in the specific embodiments which are disclosed and still obtain a like or similar result without departing from the spirit and scope of the invention. These examples are illustrations of the methods and systems described herein and are not intended to limit the scope of the invention. Specific details are provide with regards to the isolation and characterization of WAT7 peptide (SEQ ID NOS: 13 AND 14), but also provided are additional WAT targeting (SEQ ID NOS: 1-16) and lung targeting peptides (SEQ ID NOS: 17-24) which demonstrate the generic applicability of the disclosed methods.

EXAMPLES

Cell Isolation and Culture: Female C57BL/6 mice were used for screening the peptide library. To exclude strain/gender specific variables, female CD1 mice were used for peptide homing validation and subsequent cell isolations. Mice were anesthetized with Avertin for all studies.

WAT cell subpopulations from mixture of subcutaneous and intraperitoneal WAT and cells from control organs were separated as previously described in US Patent Application 20090104117 and, for example, in Traktuev, et. al., 2008, ibid and Zhang, et al., 2009, ibid. Minced issues were digested in dispase (BD Biosciences)/collagenase type I (Worthington Biochemical). Adipocytes were separated as a floating cell fraction after 200 g centrifugation. The SVF fraction and cells from control organs were filtered through 70 μm Nitex mesh. Isolated cells were separated into individual cell populations using a FACSAria (BD Biosciences) with the following IgG clones: PE-conjugated anti-CD34 MEC14.7, APC-conjugated anti-CD31 MEC 13.3, and APC-Cy7-conjugated CD45 30-F11 (BD Biosciences).

Where indicated, cells were grown in DMEM supplemented with 10% fetal calf serum (FCS) on uncoated plastic. After overnight attachment to plastic, stromal cell cultures were washed off contaminating cell populations as described (Traktuev et al., 2008, ibid; Zhang et al., 2009, ibid). Purity of cultured cell populations was confirmed by flow cytometry with CD31 and CD45 antibodies using LSR II and FacsDiva software (BD Biosciences).

Phage Library Screening: Random peptide libraries based on the M13-derived bacteriophage vector fUSE5 displaying inserts CX7C, CX8C, and CX9C on the pIII protein were admixed (1:1:1) to the combined $10^{10}$ TU of mixed library for the screen performed based on the synchronous biopanning in vivo upon tail vein injection (see for example, US20050074747 and Arap, et al., Nat. Med. 8:121-127, 2002; Kolonin, et al., FASEB J. 20: 979-981, 2006).

For competitive homing experiment, $5\times10^9$ TU for each of the 11 chosen phage clones were admixed and the combined $5.5\times10^{10}$ TU was injected. For validation of individual clones, $1\times10^{10}$ TU for each phage clones was injected. After 1 hr of circulation and heart perfusion with 10 ml of phosphate buffer saline (PBS), WAT, tibia/femurs, bone-associated skeletal muscle, and lungs were collected. Bone marrow was isolated by flushing tibia/femurs. Hematopoietic and endothelial cells were depleted from cell suspensions of each organ by Dynabeads (Invitrogen) coated with anti-TER119, anti-CD31, and anti-CD45 antibodies (BD Biosciences), after which the remaining cells were processed by FACS to purify CD34+CD31−CD45− cells. Bound phage were recovered by infecting K91 *E. coli*, quantified by phage transforming unit (TU) counting, and processed for sequencing of the peptide-coding DNA as described in Arap, et al. 2002, ibid and Kolonin, et al., 2006, ibid. For identification of conserved peptide motifs, ClustalW2 software was used.

Mouse Tissue and Cell Analysis by Immunofluorescence: Peptides chemically synthesized, cyclized via their N- and C-terminal cysteines, purified to at least 95% purity (Genemed), and biotinylated were injected (500 μg) via tail vein and allowed to circulate for 1 hr. For all tissue analyses, organs were recovered from anesthetized mice after heart perfusion with 10 ml PBS Immunolocalization of antigens was performed in paraffin sections of formalin-fixed tissues as described previously (Arap et al., 2002, ibid and Kolonin et al., 2006, ibid) upon EDTA-based antigen retrieval (DAKO), washing with 0.3% Triton X-100 and blocking in Serum-Free Protein Block (DAKO). Streptavidin-Cy3 (Zymed, 1:20) or primary antibodies (4° C., 12-16 hr) and secondary antibodies (RT, 1 hr) were applied in PBS/0.05% Tween-20. The following primary antibodies were used: rabbit anti-phage antibodies from Sigma (1:500), goat anti-mouse CD31 from Santa Cruz (1:150), rat anti-mouse CD45 from eBiosciences (1:150), rabbit anti-mouse PDGFRβ antibodies from Epitomics (1:150), and goat anti-mouse DCN antibodies from R&D Systems (1:200). Secondary donkey Alexa488-conjugated and Cy3-conjugated IgG were from Jackson ImmunoResearch. Nuclei were stained with Hoechst 33258 or TOPRO3 (Invitrogen). Cells cultured in chamber slides (Lab-Tek II; Nalge Nunc International) were subjected to immunofluorescence with anti-GFP antibodies (1:100) from Genetex Immunostained tissue sections or cell preparations were mounted in Vectashield (Vector Laboratories). Fluorescence images were acquired with an Olympus IX70 inverted fluorescence microscope/Magnafire software (Olympus). Confocal images were acquired with a Leica TCS SP5 microscope/LAS AF software.

Isolation of Proteins by Affinity Chromatography: Cells were disrupted in PBS containing 0.2 mM phenylmethanesulphonylfluoride/Roche PI cocktail by using Dounce homogenizer; centrifugation (15,000 g for 30 min at 4° C.) was used to separate soluble proteins from membrane pellet. Solubilization of cellular membrane proteins was performed as previously described in US Patent Application 20090104117 and Nie, et al., 2008 (*Stem Cells* 26: 2735-2745). Briefly, membrane pellet was incubated in PBS containing 1 mM $CaCl_2$, 1 mM $MgCl_2$, 50 mM n-Octyl-beta-D-glucopyranoside, 0.2 mM phenylmethanesulphonylfluoride/Roche PI cocktail (column buffer) overnight at 4° C. and centrifugation (15,000 g for 30 min at 4° C.) was performed to remove insoluble debris. For WAT7 receptor purification, 5 mg of a cysteine-cyclized peptide (Genemed Synthesis) was coupled (via C-terminus) onto 0.25 ml of EDC Sepharose (Pierce), and the column was equilibrated with column buffer containing 1% Triton X-100. Peptide-coupled resin was incubated with 40 mg of membrane extract, washed extensively with column buffer by gravity flow. Elution (0.5 ml fractions) was performed with 1.0 mM peptides, followed by 0.1 M glycine (pH 2.8). For panning on eluates, 20 μl of $10^5$ TU of indicated phage clones were incubated overnight at 4° C. with 2 ml of each fraction desalted using Microcon filter (Millipore) immobilized on plastic. Unbound phage were extensively washed off with PBS, and then the bound phage were quantified by infecting host K91 *E. coli* directly on the plate. The remaining WAT7-phage-binding fraction was subjected to sodium dodecyl sulfate (SDS)-PAGE; mass spectrometry protein identification in WAT7-specific band was performed by ProtTech. For purification of ΔDCN, 20 mg of anti-DCN antibodies were immobilized on Protein A/G beads (Pierce) and incubated with 40 mg of membrane extract. Upon washing with Protein A/G binding buffer (Pierce), the 40 kDa band identified by SDS-PAGE was subjected to N-terminus microsequencing at the Baylor College of Medicine proteomics facility. For purification of resistin, pre- and post-immune rabbit antisera raised against cyclized KLH-coupled cysteine-cyclized WAT7 (Genemed Synthesis) were used. To validate antibody specificity, glutathione-S-transferase (GST)-tagged peptides were produced by cloning fragments encoding the $CX_7C$ amino acids in-frame with GST Tag into pGEX4T-1 vector and using the GST Bind kit (Novagen). GST-conjugated peptide KGGRAKD (SEQ ID NOS: 25 and 26) and prohibitin, as well as peptide mPep WLGEWLG (SEQ ID NO: 35 and 36) were described previously Nie, et al., 2008, ibid.

Proteins binding to WAT7-specific antibodies were pulled down from total mouse WAT SVF extract as above, resolved by SDS-PAGE, and mass spectrometrically identified by ProtTech. For isolation of biotinylated ASC proteins, streptavidin-coupled Dynabeads M270 (Invitrogen) were used. For analysis of plasma membrane proteins, a plasma membrane-enriched fraction was prepared using Qproteome PM isolation kit (Qiagen). Cell surface protein biotinylation was performed as described in Kolonin, et al., Nat. Med. 10: 625-632, 2004) using EZ-Link Sulfo-NHS-LC-Biotin (Pierce).

Immunoblotting and Binding Assays: Protein preparations resolved on SDS-PAGE were blotted onto Immobilon-FL membrane (Millipore), blocked with Odyssey blocking buffer (Licor Biosciences), and probed (in PBS/0.05% Triton X-100) with goat anti-DCN (R&D Systems, 1:1,000), rabbit anti-ANX2A (Aviva, 1:1,000), rabbit anti-mouse b-actin (Abcam, 1:10,000) antibodies, or pre- and post-immune antisera against WAT7 (1:1,000) as indicated. Signal was detected by Odyssey imaging system using anti-goat IRDye 800CW or anti-rabbit IRDye 680 both from Licor Biosciences. Bovine DCN was from Sigma-Aldrich, NS0-derived murine DCN was from R&D Systems. Murine DCN cDNA was generated from WAT total RNA using Super-Script kit (Invitrogen). For bacterial expression, full-length mouse core DCN and ΔDCN isoforms were produced by cloning fragments encoding amino acids 1-354 and 45-354 of mouse DCN cDNA (OriGene) or of CLIC4 cDNA (OriGene) in-frame with the $His_6Tag$ into pET28a vector, respectively. $His_6$-tagged proteins were purified with His-Tag kit (Novagen). For ELISA binding assays, 100 µl of 10 µg/ml of indicated $His_6$-DCN preparations, $His_6$-CLIC4 (control $His_6$-protein), NS0 cell-expressed mouse DCN (R&D Systems), purified bovine DCN (Sigma-Aldrich), or BSA were coated and immobilized onto Maxisorb Immunoplates (96 well; NUNC) overnight at 4° C., followed by blocking with 3% BSA, and then incubating with 100 µl of indicated concentrations of WAT7 or control WAT2 peptides. For adipokines binding assay, FLAG-tagged mouse resistin produced in HEK293 cells (Enzo Life Sciences), or control FLAG-BAP protein (Sigma-Aldrich) were incubated at the concentrations indicated. Bound peptides or FLAG-resistin were probed with corresponding rabbit anti-peptide Genemed antibodies (1:2,000) or rabbit anti-FLAG antibodies (Sigma-Aldrich, 1:2,000) followed by secondary goat anti-rabbit HRP-conjugated antibodies (Millipore, 1:5,000) and signal detection with Ultra-TMB (Pierce) substrate and measurement of absorbance at 450 nm.

Functional assays: To generate stably transduced cell lines, cDNA (OriGene) fragments coding for full-length mouse core DCN and ΔDCN isoforms were cloned into pLVX-AcGFP-C1 vector (Clontech). Lentiviruses were produced in Lenti-X 293T cells using Lenti-X HTX packaging system according to the manufacturer's protocol. Lentivirus harboring vector alone, DCN, or ΔDCN were used to transduce NIH3T3-L1 cells (ATCC). After 72 hr, cells were treated with 2 µg/ml of puromycin for 4-5 days to select for stable cells lines, which have been afterwards maintained in medium containing 0.5 µg/ml puromycin. For measuring cell proliferation by the MTT assay, equal number (5,000 cells) of early passage lentivirus transductants (P2) were plated on a 96-well plate. At the indicated time points, cells were treated with CellTiter-Blue reagent (Promega) for 4 hr at 37° C., after which the fluorescence was measured at 560 emission and 590 excitation wavelength. For measuring cell migration by the Transwell assay as described (Nie, et al., 2008, ibid), cells were starved for 2 hr in DMEM/0.1% FBS and then 25,000 cells were seeded in the same media on a transwell insert (5 µM pore size). The insert was placed on top of the lower chamber containing DMEM/10% FBS, cells were allowed to migrate to the bottom of the transwell for 12 hr, fixed, stained with Hematoxylin/Eosin and counted. 3T3-L1 stable cell lines (60,000 cells/well) were plated on a 12-well plate. Adipogenesis was induced as described in Nie, et al., 2008, ibid: at 2 days post-confluence, DMEM/10% FBS containing 0.5 mM IBMX, 1.7 mM insulin, 1 uM dexamethasone and 0.2 mM indomethacin was added and after 72 hr was replaced with DMEM/10% FBS containing 1.7 mM insulin refreshed every 2 days.

Statistical analysis: Performed by using the Student's t test with significance being assigned to $P<0.05$.

Example 1

Identification of ASC-Homing Peptides

Figure 1B:
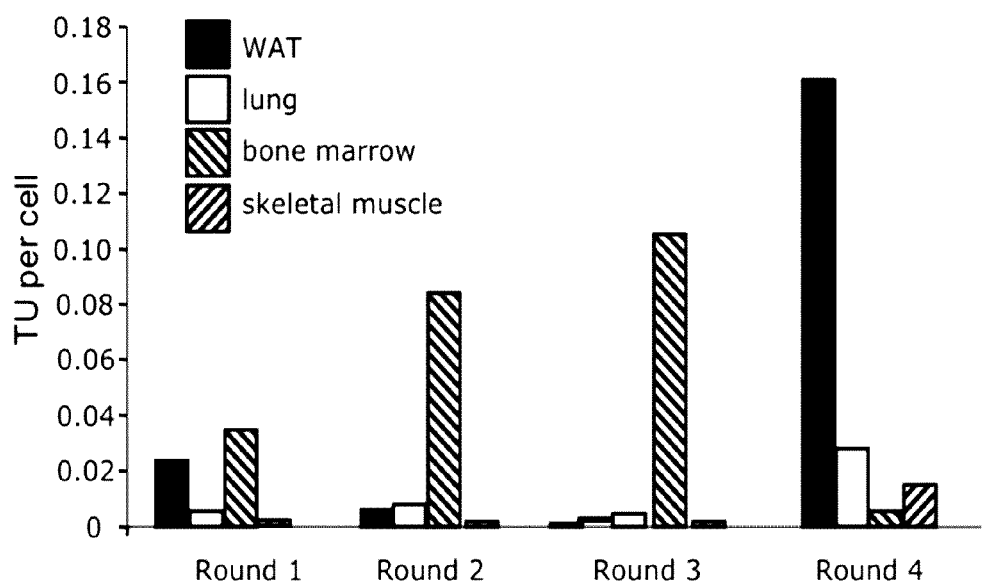

Methods for isolation of MSC by fluorescence-activated cell sorting (FACS) from organ cell suspensions based on the C34+CD31−CD45− immunophenotype (FIG. 8B) were combined with phage display and optimized for ASC. By adapting the previously described "synchronous in vivo biopanning" method of (Kolonin et al., 2006, ibid), a mixture of cyclic $CX_7C$, $CX_8C$, and $CX_9C$ (C: disulfide-bonded cysteines; X: any amino acid) random peptide libraries was screened (FIG. 1A). This approach made it possible to select MSC probes from the pool of over $10^{11}$ combinatorial peptides. Throughout the screen, progressive enrichment in the number of phage particles recovered on MSC from WAT, as well as from the chosen control organs: lung, bone marrow, and skeletal muscle (FIG. 1B) was observed.

Sequencing of DNA coding for peptide inserts revealed selection of clones from CX7C and CX8C libraries, whereas clones from the CX9C library have been predominantly lost possibly due to propagation disadvantage of phage containing longer peptide inserts in the pIII protein.

Figure 1C:
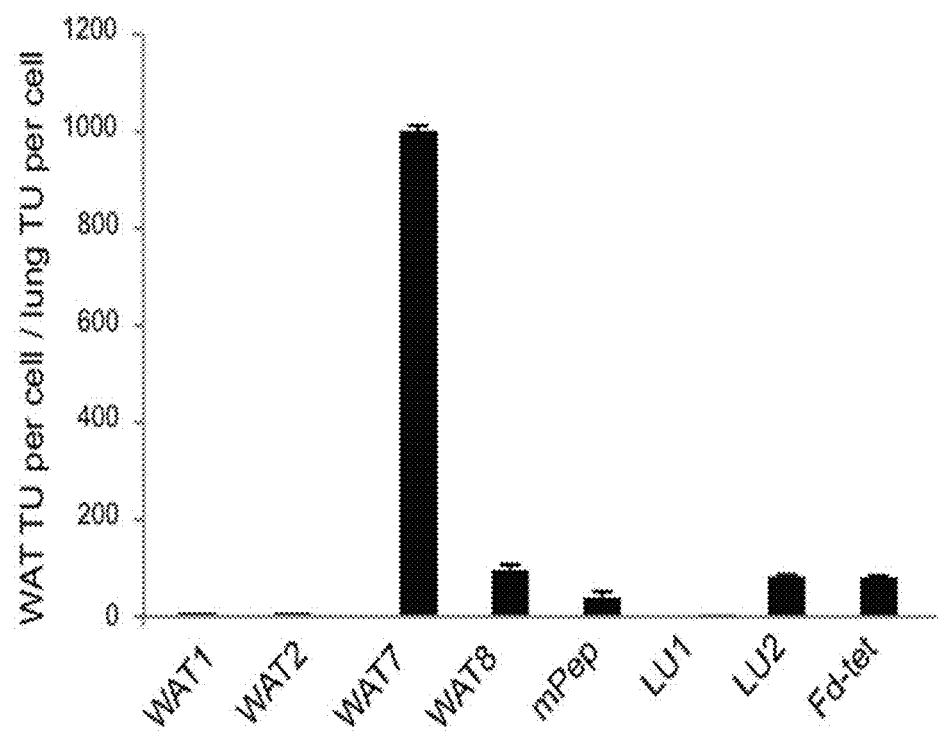

After 4 rounds of synchronous in vivo biopanning, eight $CX_7C$ and $CX_8C$ sequences repeatedly recovered from ASC with frequency above 1% were identified, which were termed WAT1 through WAT8 (see Table 1 below). In parallel, a matched number of peptide inserts homing to lung stromal cells (LSC) were sequenced as a control. None of the WAT-homing peptides were enriched in the lung. Four sequences repeatedly recovered in the lung with frequency above 1%, were termed LU1 through LU4 (see Table 1 below). Comparative analysis of individual phage clones in vivo revealed WAT7, homing to ASC a 1,000 times more than to LSC, as a peptide with the highest specificity for ASC (FIG. 1C). Clone WAT8 displayed modest preference for ASC, as compared to LSC at a level similar to mPep, a previously characterized peptide mimicking SPARC (Nie, et al., 2008, ibid). Consistent with this observation, the sequence of WAT8 peptide (CGQWLGNWLC: SEQ ID NO: 15) was found to be similar to mPep (CWLGEWLGC: SEQ ID NO: 35), indicating integrin 131, a previously established marker of MSC as a likely receptor for WAT8 peptide. Because the focus of this study is WAT-specific MSC, this clone was excluded from further analysis. Other selected peptides were subjected to an in vivo competition assay in order to identify those with the highest specificity of binding. Equal amounts of phage for the 11 clones displaying peptides WAT1 through WAT7 (SEQ ID NOS: 1-14) and LU1 through LU4 (SEQ ID NOS: 17-24) were admixed and injected into a mouse. Homing specificity of each clone was assessed by quantifying frequency of phage coding for each peptide selected on C34+CD31−CD45− cells isolated from either WAT or lung. Consistent with data above (FIG. 1C), peptide WAT7 stood out based on its marked capacity to re-home to WAT cells: it represented 87.4% of clones recovered from WAT and only 5.8% of clones recovered from lung. Reciprocally, clones LU-1 and LU-2 displayed re-homing to lung (52.2% and 40.2%, respectively) but not to WAT (see Table 1 below).

Example 2

Figure 2A:
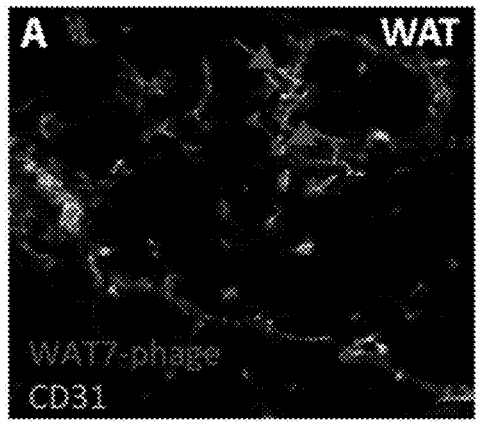
FIGS. 2A-J depict the validation of cyclic WAT7 Peptide (SEQ ID NOS: 13) Homing to ASC. Panels A-D are confocal anti-phage (red) and anti-CD31 (bright green) immunofluorescence in paraffin sections of formalin-fixed WAT and lung from mice intravenously injected with phage displaying WAT-homing peptide WAT7 (SEQ ID NOS: 13 AND 14) or a lung-homing peptide LU2 (SEQ ID NOS: 19). Red signal upon digital channel merging indicates localization (arrow) of phage on non-endothelial perivascular cells observed for WAT7 (SEQ ID NOS: 13) in WAT (A) but not in lung (B), and for LU2 (SEQ ID NO: 19) in lung (D) but not in WAT (C). Panels E-J illustrate biodistribution of biotinylated peptide WAT7 1 hr post-intravenous injection, revealed by confocal microscopy detecting streptavidin-Cy3 (red) and contrasted with tissue expression of PDGFRβ (red), CD31 (bright green) or CD45 (green) detected by immunofluorescence. Note the association (arrow) of cyclic WAT7 (SEQ ID NOS: 13) specifically with perivascular WAT cells (E) in a pattern overlapping with PDGFRβ expressed on ASC (F-G). Like PDGFRβ, WAT7 is not associated with CD31+ endothelial cells (E) or CD45+ hematopoietic cells (H). WAT7 was not detected in lung (I) despite the abundance of PDGFRβ+LSC (J). Nuclear TOPRO3 staining is blue. Scale bar: 100 μM.
Figure 2D:
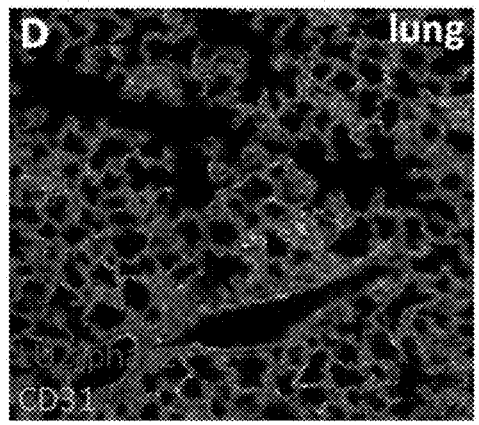
Figure 2B:
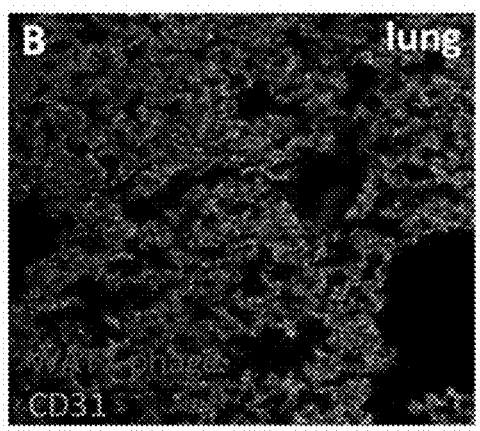
Figure 2E:
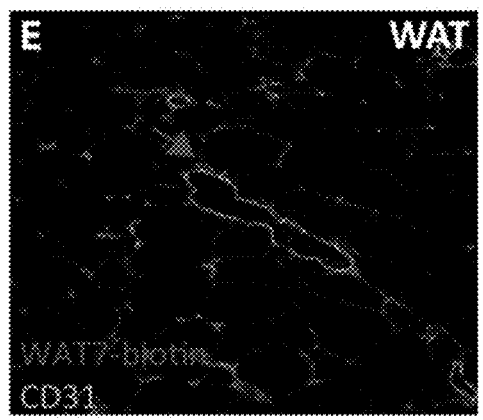
Figure 2C:
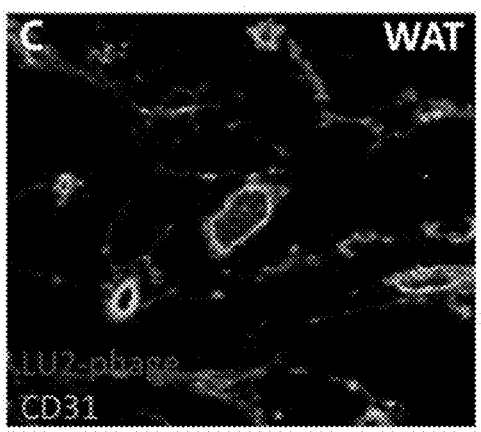
Figure 2F:
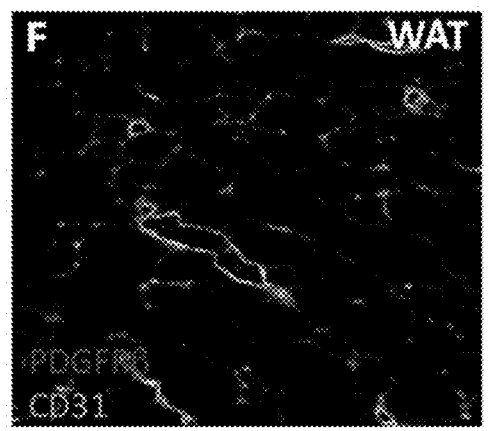
Figure 2G:
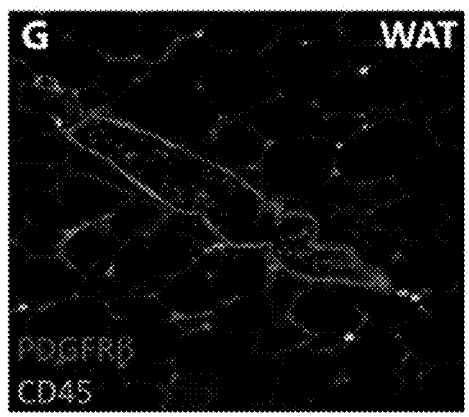
Figure 2H:
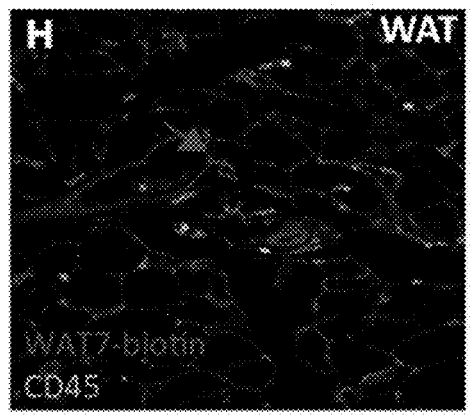
Figure 2I:
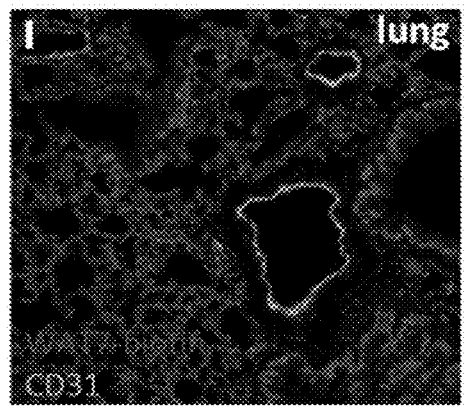
Figure 2J:
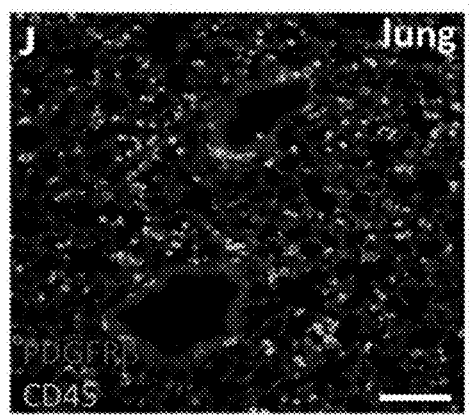

Validation of WAT7 (sequence CSWKYWFGEC and SWKYWFGE (SEQ ID NOS: 13 AND 14)) as a Peptide Targeting ASC Based on the combined homing data, peptide WAT7 (sequence CSWKYWFGEC: SEQ ID NO: 13) showing the most definitive ASC-targeting was chosen for further analysis. Peptide LU2 (sequence CESGFPTVGC SEQ ID NO: 19) was chosen as a control peptide targeting MSC in the lung but not in WAT. Homing of WAT7 was validated by analyzing biodistribution of WAT7-displaying phage in moue tissues upon intravenous injection. Immunofluorescence in mouse tissue sections demonstrated that phage accumulation was associated with the stroma/vasculature of WAT (FIG. 2A) but not of lung (FIG. 2B) or other control organs. Reciprocally, LU2 accumulation was associated with the stroma/vasculature of lung (FIG. 2D) but not of WAT (FIG. 2C). To validate the capacity of peptides to home outside the phage context, chemically synthesized cyclic WAT7 and LU2 flanked by disulfide-bonded cysteines were biotinylated. Intravenous administration of each peptide into mice followed by immunofluorescence analysis of tissues with streptavidin-conjugated fluorophore reproduced selectivity of WAT7 for WAT (FIG. 2). Co-staining with CD31-specific and with PDGFRβ-specific antibodies identifying endothelial cells and pericytes, respectively, was performed to identify the target cell population. Confocal imaging revealed perivascular localization of WAT7 in association with PDGFRβ+ cells (FIG. 2E-G) that have been previously established as ASC (see Traktuev, et al., 2008, ibid). Importantly, WAT7 did not co-localize with either endothelial cells (FIG. 3E) or with CD45+ hematopoietic cells (FIG. 2H) infiltrating WAT. Consistent with the data on phage biodistribution, WAT7 peptide was not detected in lungs of injected animals (FIG. 2I), despite the abundance of MSC revealed by PDGFRβ immunofluorescence (FIG. 2J). In agreement with in vivo homing data, phage displaying WAT7 showed high level of specific binding to primary non-passaged ASC, but not to LSC isolated from the same animal, or to 3T3-L1 mouse preadipocytes and 4T1.2 mouse adenocarcinoma cells (FIG. 9).

Example 3

Isolation of WAT7 Receptor

Figure 3A:
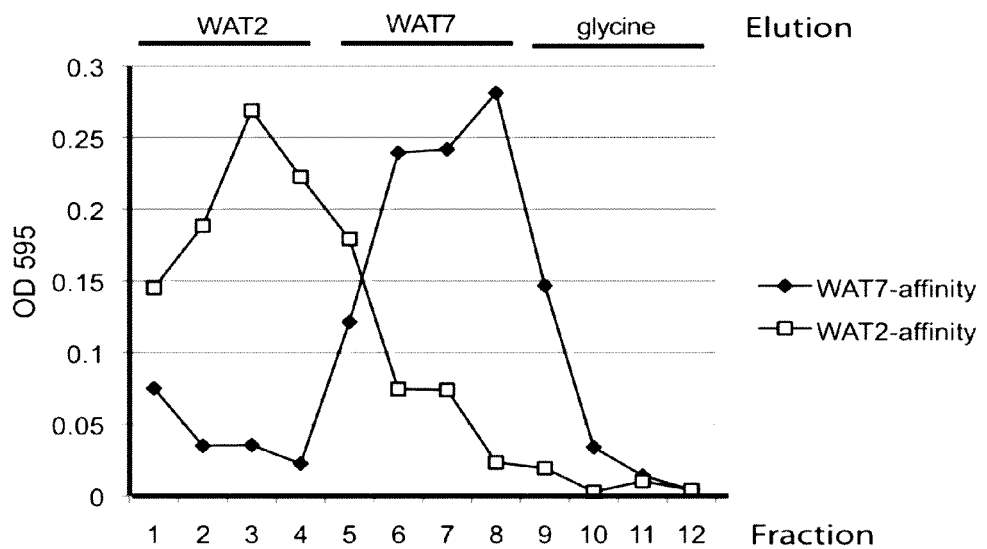
FIGS. 3A-C depict the purification of decorin as a WAT7-binding Protein. (A) Cysteine-cyclized synthetic peptides WAT7 (SEQ ID NOS: 13) and WAT2 (SEQ ID NO: 3: control) covalently linked to EDC Sepharose were incubated with membrane protein extract from mouse ASC. After washing, proteins bound to WAT7 affinity column were consecutively eluted with WAT2 (fractions 1-4), WAT7 (fractions 5-8) and 0.1 M glycine pH 2.5 (fractions 9-12); for WAT2 affinity column the order of peptide elutions was reversed. Protein concentration in each fraction was measured by the Bradford assay and plotted as OD595 absorbance. (B) Desalted proteins from each fraction were coated on plastic and exposed to phage displaying WAT7 or WAT2. 7/7: WAT7 affinity/WAT7-phage; 2/7: WAT2 affinity/WAT7-phage; 7/2: WAT7 affinity/WAT2-phage; 2/2: WAT2 affinity/WAT2-phage. Phage binding was quantified based on TU recovery upon host bacteria infection: increased WAT7-phage binding for WAT7 affinity fraction 5 indicates elution of a WAT7-binding protein. (C) Proteins from WAT7 affinity fractions 1 (control) and 5 were resolved by gradient 4-15% SDS-PAGE. Coomassie staining of the gel demonstrates a 40 kDa band (arrow) specifically eluted with WAT7. Mass spectrometry identified the corresponding protein as DCN.
Figure 3B:
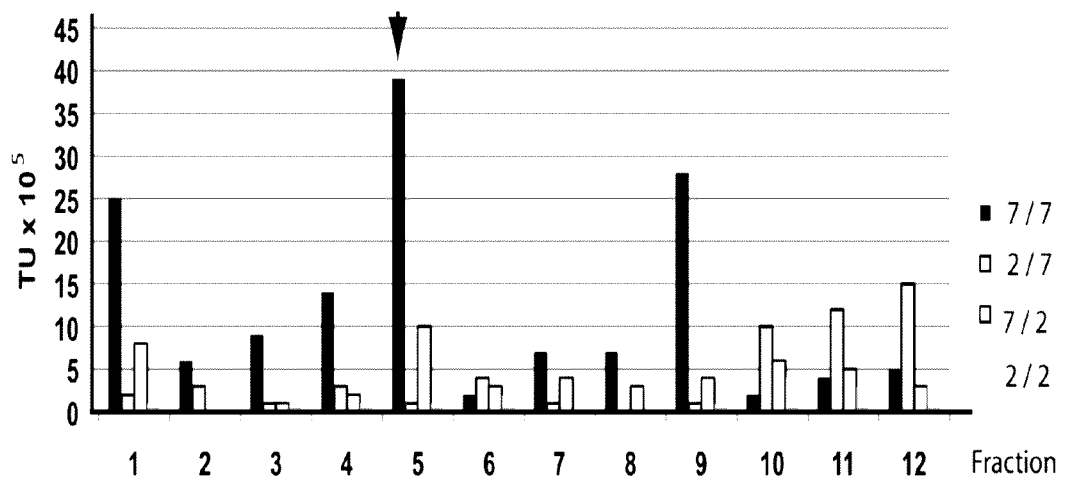
Figure 3C:
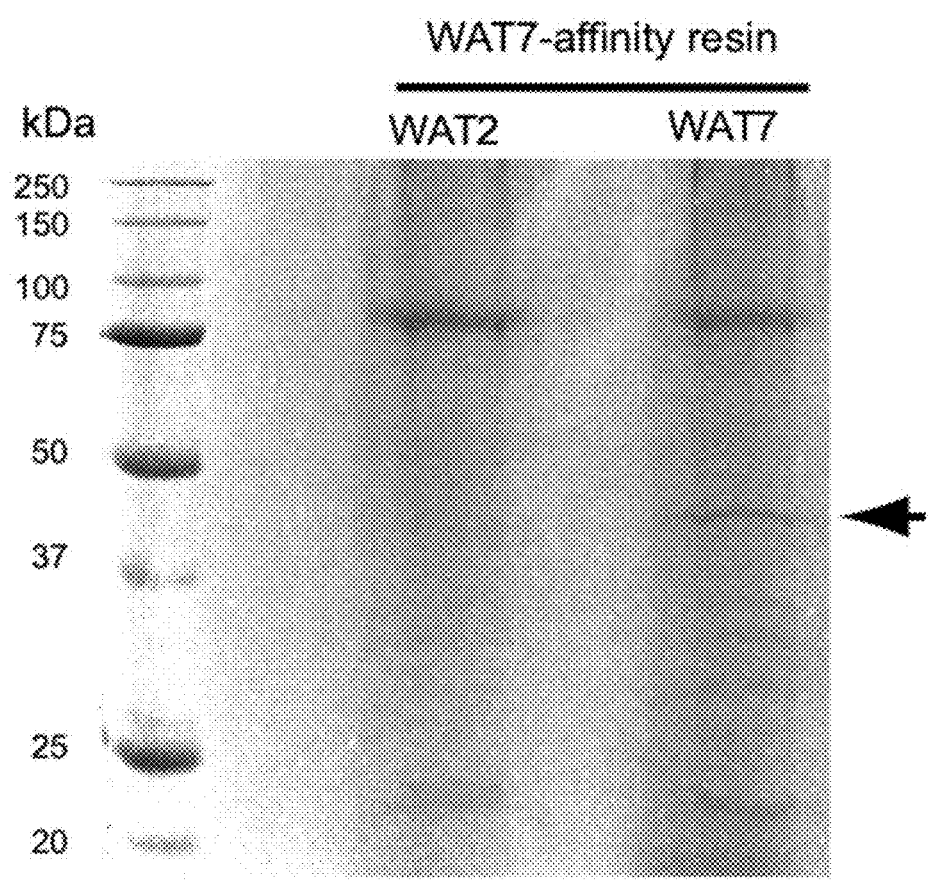

To identify the receptor for the ASC-homing Peptide WAT7 affinity chromatographic methods were used. Membrane proteins were extracted from the SVF of mouse WAT and applied to cysteine-cyclized synthetic WAT7 covalently coupled to resin through its carboxyl terminus. Elution with WAT2 peptide (sequence CYKNVDSGGC: SEQ ID NO: 3) was first used to remove nonspecifically bound proteins (FIG. 3A). Specifically bound proteins were then eluted with WAT7 and appeared in discrete subset of fractions. A WAT2 peptide affinity column was used in parallel to confirm specificity of affinity-purified proteins. Testing of desalted eluates coated onto plastic for phage-peptide binding confirmed that these fractions contained proteins binding to WAT7-displaying phage, but not to control WAT2-displaying phage (FIG. 3B). Fractions eluted with WAT7 from a control affinity column loaded with WAT2 and exposed to the same membrane protein extract were not bound by WAT7-displaying phage (FIG. 3B). Fraction 5, containing proteins pulled-down and specifically eluted with WAT7, showed the highest level of binding by WAT7-displaying phage and was chosen for receptor purification. Proteins eluted in this fraction were concentrated and resolved by denaturing gradient polyacrylamide gel electrophoresis (PAGE). A band specifically eluted with WAT7, but not with the control peptide WAT2, migrated at approximately 40 kDa (FIG. 3C). Mass spectrometric analysis of this band revealed that it contained decorin (DCN), alternatively known as proteoglycan II.

Figure 4A:
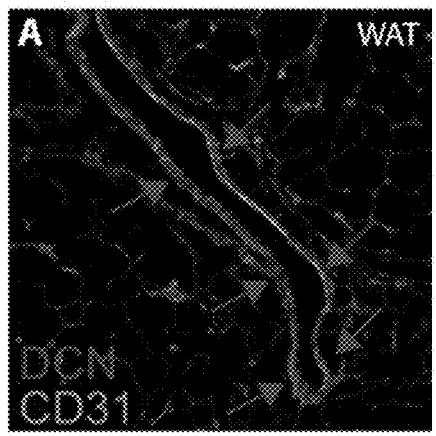
FIGS. 4A-F depict decorin overexpression in WAT. Confocal immunofluorescence of formalin-fixed paraffin-embedded mouse tissues with anti-mouse DCN or anti-mouse PDGFRβ antibodies (red) counter-stained with endothelial-specific anti-CD31 antibodies (bright green) demonstrating that both DCN (arrows) and PDGFRβ (arrowheads) are expressed on perivascular cells (ASC) in WAT (A, D). DCN expression is only rarely found in association with blood vessels in lungs (B) and is undetectable in the bone marrow (C), whereas PDGFRβ is ubiquitously expressed by the lung stroma (E) and in the bone marrow (F). Blue: nuclear TOPRO3 staining. Scale bar: 100 µM.
Figure 4B:
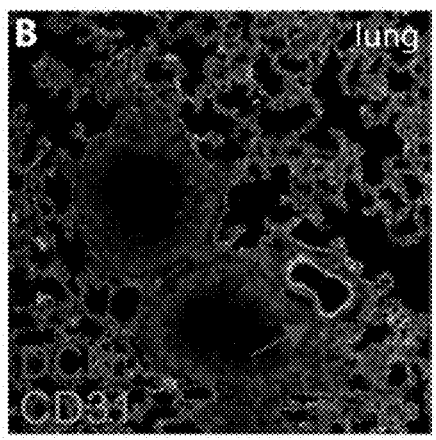
Figure 4C:
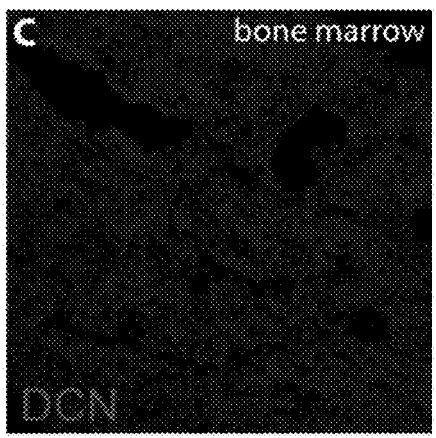
Figure 4D:
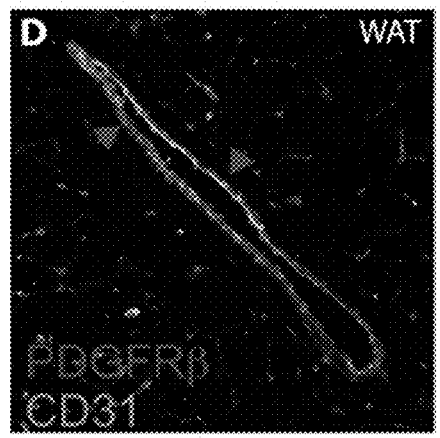
Figure 4E:
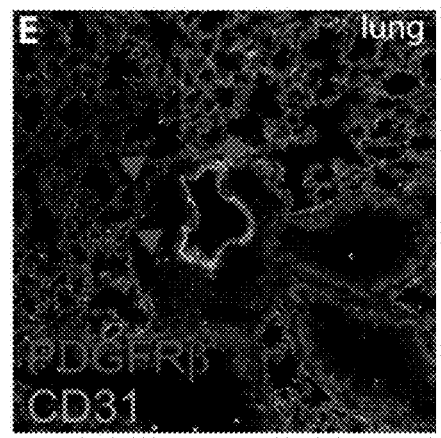
Figure 4F:
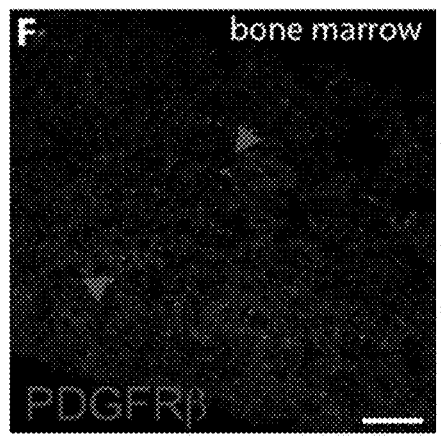

Because DCN is an extensively studied molecule secreted into the extracellular matrix (ECM) and controls several physiological processes. Its ubiquitous mRNA expression appeared inconsistent with WAT7 homing to ASC in WAT. Therefore, to analyze DCN protein levels in mouse organs, a panel of mouse tissue sections were subjected to confocal immunofluorescence with commercially available antibodies raised against full-length glycosylated mouse DCN. Consistent with previous studies by Bolton et al., 2008 (*Int. J. Obes.* 32: 1113-1121, 2008), DCN protein was detectable in many organs, however it was particularly highly abundant in WAT as compared to lung and bone marrow (FIG. 4A-C). This was in striking contrast with expression of PDGFRβ that was comparable in all organs (FIG. 4D-F), as assessed in the same sections in parallel. The pattern of DCN and PDGFRβ in WAT was undistinguishable, and the localization of each protein to perivascular cells surrounding CD31-positive endothelium indicated that most of DCN in WAT is produced by ASC (FIGS. 4A and 4D). However, the detection of DCN expression by perivascular cells of a subset of vessels in lungs (FIG. 5B) and in some other organs (data not shown) suggested that difference in DCN expression level by different subpopulations of MSC might not be sufficient to account for WAT7 homing to ASC.

Figure 5A:
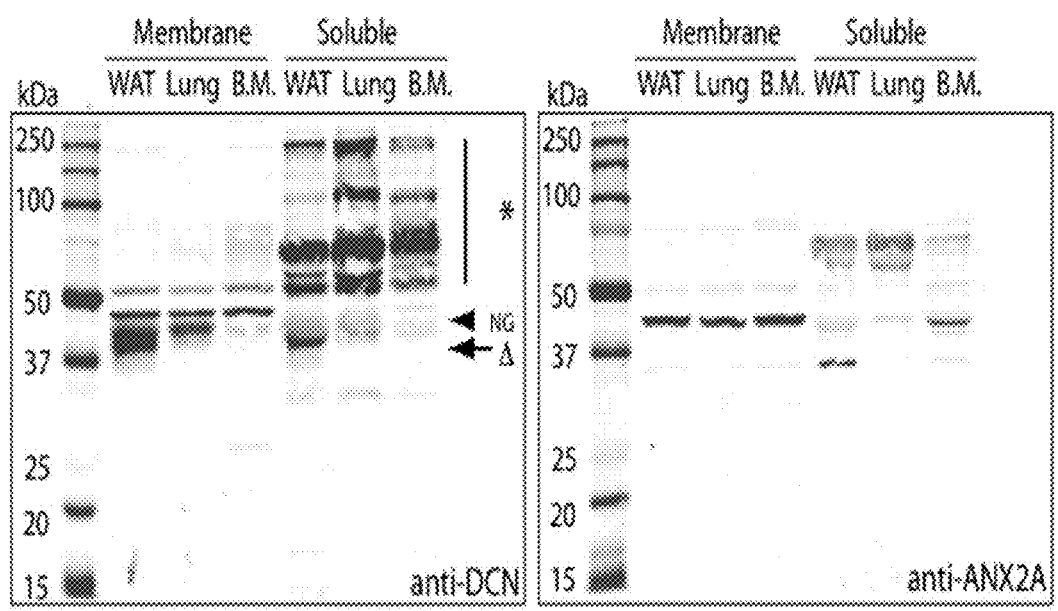
FIGS. 5A-G illustrate that a cleavage fragment of DCN (ΔDCN) is the WAT7 Receptor on ASC. (A) Immunoblotting of membrane-associated and soluble proteins extracted from subpopulations of mouse WAT with the DCN antibodies showing that ΔDCN (arrow) is expressed specifically by ASC but not by adipocytes. Control immunoblotting of the gel with actin antibodies demonstrates equal protein loading. (B) Affinity purification of ΔDCN from mouse membrane WAT SVF extract. Coomassie blue staining of Gel identified the expected 40 kDa band (arrow) between light and heavy chains of the anti-DCN IgG. (C) Edman degradation microsequence of ΔDCN isolated in (B) (SEQ ID NO: 40) aligned with full-length mouse (SEQ ID NO: 41) and human (SEQ ID NO: 42) DCN. Previously reported sites of protease cleavage, resulting in the processing of propeptide and core DCN, are indicated. Sequence corresponding to amino acids 56-295 of mDCN is not shown. (D) Measurement of WAT7 binding to recombinant bacterially-purified mouse ΔDCN, as compared to recombinant bacterially-purified full-length core mouse DCN (mDCN), full-length glycosylated mouse DCN (mDCN*), glycosylated bovine DCN (bDCN*), and BSA by ELISA. OD450 absorbance, plotted as a function of peptide concentration, shows dose-dependent ΔDCN-WAT7 and mDCN-WAT7 binding. Shown are mean±SD for triplicate wells; *P<0.05. (E) Anti-DCN immunoblotting of total cell and cell membrane-associated proteins extracted from mouse WAT SVF showing that ΔDCN (arrow) is associated with cell membrane. (F) Exposure of ΔDCN on the surface of mouse ASC assessed through treatment of cells with a biotinylation reagent. Biotinylated proteins (isolated with streptavidin beads) were subjected to anti-DCN immunoblotting, revealing ΔDCN (arrow) undergoing biotinylation on freshly isolated but not on cultured ASC. (G) 3T3-L1 cells stably transduced with lentivirus expressing GFP (vector), full-length core mouse DCN-GFP fusion (DCN), or mouse ΔDCN-GFP fusion (ΔDCN). GFP immunofluorescence shows cell surface localization of the GFP-ΔDCN fusion. Scale bar: 10 µM.
Figure 16A:
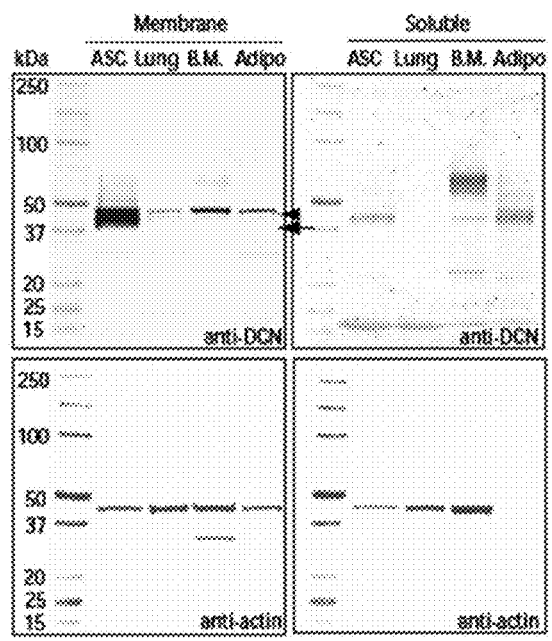
FIGS. 16A-B. (A) Illustrates immunoblotting of membrane-associated and soluble proteins extracted from mouse WAT, lung and bone marrow (B.M.) with antibodies against mouse DCN. The migration of non-glycosylated core DCN (arrowhead), and a WAT-specific isoform (arrow) is indicated. Control immunoblotting of the gel with ANX2A antibodies demonstrates equal membrane protein loading. (B) Measurement of WAT7 (top) and of WAT2 control (bottom) peptide binding to recombinant core mouse DCN (mDCN), glycosylated bovine DCN (bDCN*) and BSA by ELISA. OD450 absorbance, plotted as a function of peptide concentration, shows dose-dependent mDCN-WAT7 binding.

To characterize the expression of the non-glycosylated DCN in WAT, protein extracts from mouse tissues were subjected to immunoblotting with polyclonal antibodies raised against full-length mouse DCN (FIG. 5A). Analysis of cytosolic proteins from the SVF fraction of WAT, as well as from lung and bone marrow, showed comparable expression of higher molecular weight glycosylated DCN isoforms in these organs. In contrast, WAT displayed increased expression of a ~40 kDa non-glycosylated core DCN lacking the dermatan/chondroitin sulfate glycosaminoglycan (GAG) chain (FIG. 5A). Interestingly, immunoblot analysis of membrane proteins from the three organs revealed WAT-specific expression of a DCN isoform with a molecular weight lower than that of the non-glycosylated core DCN previously characterized (Imai et al., *Biochem. J.* 322 (Pt 3), 809-814, 1997; Roughley et al., *Biochem. J.* 318 (Pt 3): 779-784, 1996) in other organs. Absence of this DCN isoform expression in lung and bone marrow is evident from the same blot probed with antibodies against a control membrane protein, annexin II (ANX2A), which were used to control for protein loading (FIG. 5A) immunoblotting was also used to characterize which cells in WAT express the low molecular weight DCN isoform. These findings indicate that it associates exclusively with the membrane (but not with cytosolic) fraction of ASC, but not of differentiated adipocytes FIG. 16A.

Example 4

A New DCN Isoform is the CSWKYWFGEC (SEQ ID NOS: 13) Receptor

Figure 5B:
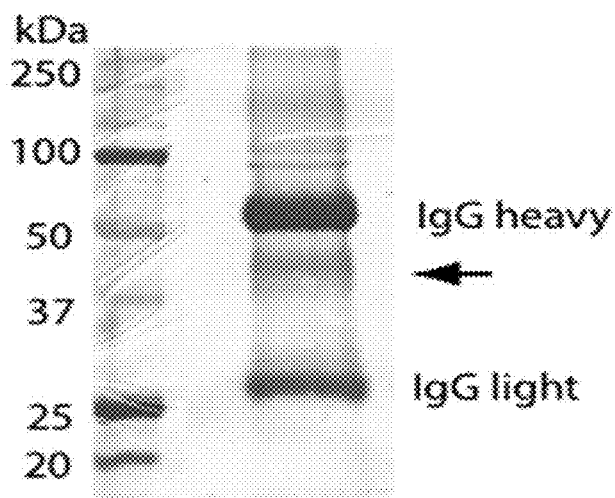
Figure 5C:
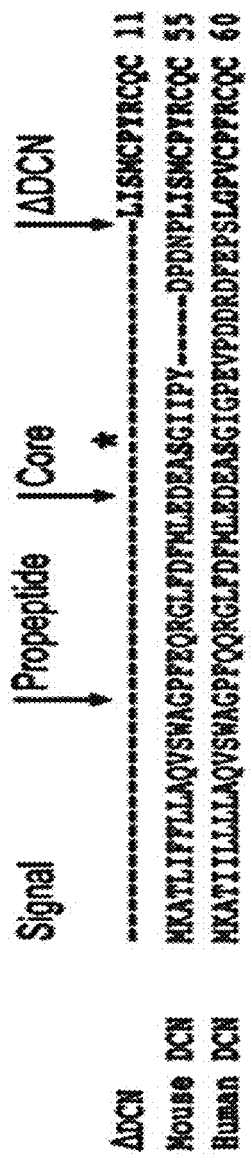

To establish the identity of the WAT-specific DCN isoform, which was termed ΔDCN, DCN antibodies were used to purify DCN from the mouse membrane extract of the SVF isolated from WAT. Analysis of immunoprecipitated proteins by denaturing PAGE revealed the expected 40 kDa band corresponding to ΔDCN (FIG. 5B). Edman degradation microsequencing of the protein cut out from the band revealed that this DCN fragment starts at Leu-45 (FIG. 5C), and is therefore 14 amino acids shorter than the previously described mature core DCN generated after propeptide cleavage (Imai et al., 1997, ibid; Roughley et al., 1996, ibid). Therefore, ΔDCN cannot be glycosylated because it is missing the GAG attachment site SerGly (FIG. 5C) present in core DCN (Scholzen et al., *J. Biol. Chem.* 269: 28270-

28281, 1994). Lack of methionines in the core DCN sequence missing from ΔDCN indicates that ΔDCN is generated by proteolytic cleavage rather than by alternative splicing.

Figure 5D:
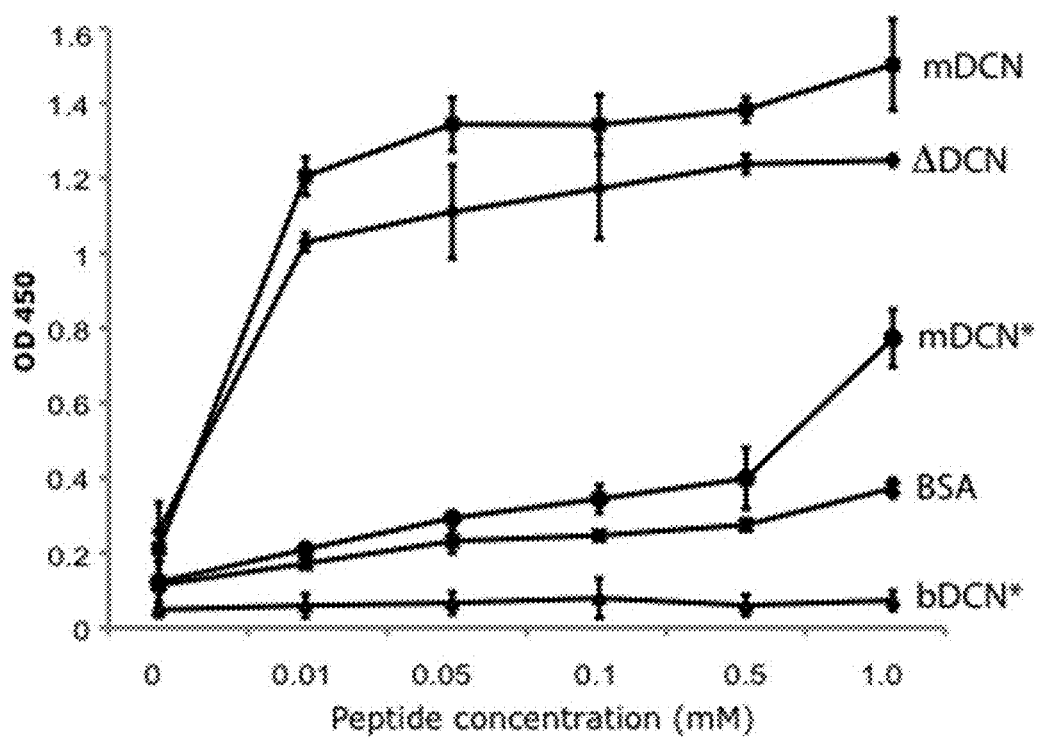
Figure 16B:
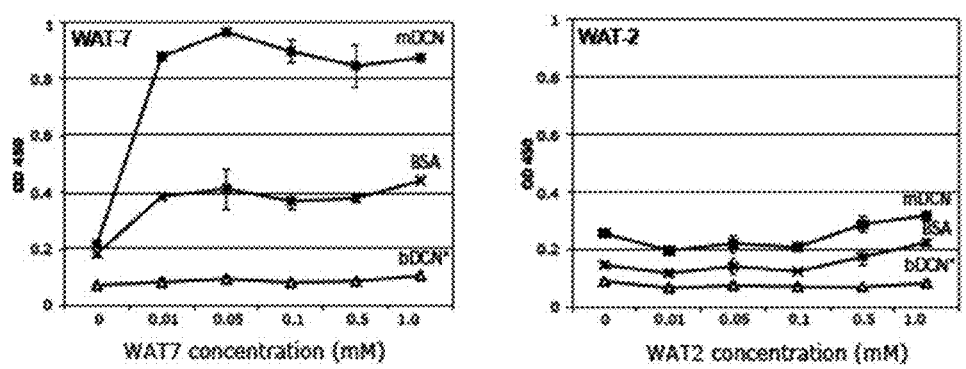

To validate DCN as the target of WAT7, enzyme-linked immunosorbent assays (ELISA) using His6-tagged proteins was used. These in vitro binding studies demonstrated clear dose-dependent binding of WAT7 to recombinant bacterially-purified mouse DCN, while the control peptide WAT2 did not display DCN binding FIG. 16B. Interestingly, WAT7 did not bind to commercially available glycosylated bovine DCN at the level above the background observed for bovine serum albumin (BSA). Further analysis including ΔDCN demonstrated that WAT7 bound to ΔDCN, as well as to bacterially expressed (and therefore non-glycosylated) DCN core protein (FIG. 5D). Lack of WAT7 binding to either bovine or mouse glycosylated DCN above the background BSA binding (FIG. 5D) demonstrates that the GAG chain on mature DCN prevents WAT7 binding. This finding may explain why ubiquitous secretion of glycosylated DCN into the ECM in organs other than WAT (Reed and Iozzo, Glycoconj. J. 19: 249-255, 2002) does not interfere with WAT homing of the WAT7 peptide.

Figure 5E:
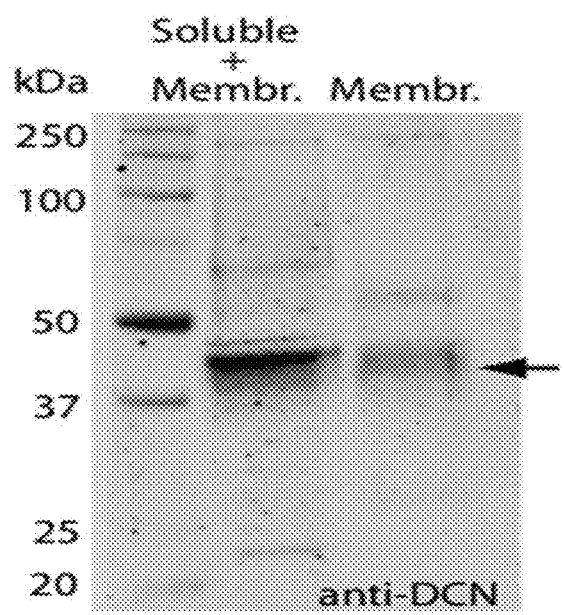
Figure 5F:
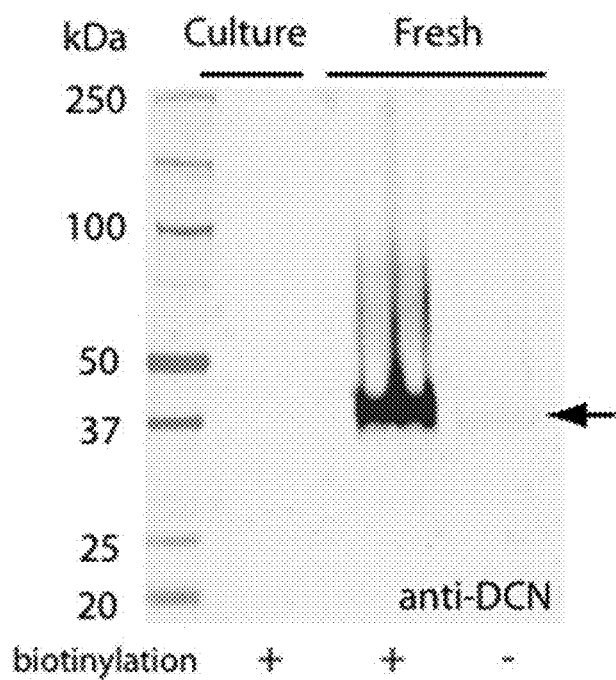
Figure 5G:
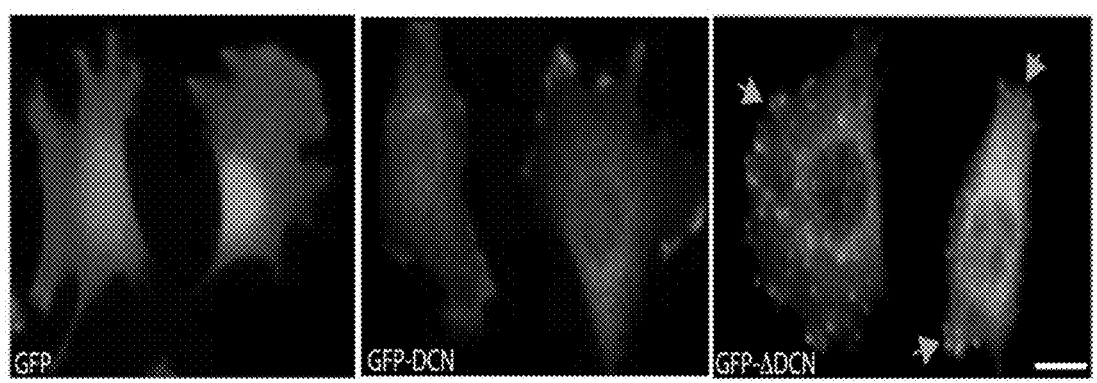

In order to serve as a receptor for WAT7, ΔDCN must be exposed on the surface of ASC. By isolating plasmalemma protein fraction from the total membrane preparation of the SVF, it was demonstrated that ΔDCN is associated with the cell membrane of ASC (FIG. 5E). In addition using an alternative approach to confirm that ΔDCN is displayed on ASC, the surface proteins of freshly isolated WAT SVF cells were biotinylated as described (Kolonin et al., 2004, ibid), after which the biotinylated proteins were isolated by using streptavidin beads and subjected to anti-DCN immunoblotting. As expected, ΔDCN was isolated, indicating its association with the cell surface (FIG. 5F). Interestingly, overnight culturing of WAT SVF cells on plastic in conditions typically used for MSC/ASC propagation resulted in the disappearance of ΔDCN from the pool of cell surface proteins (FIG. 5F). This indicates that exposure of ΔDCN on the cell surface taking place in vivo is not retained in cell culture. Finally, cellular localization of ΔDCN recombinantly fused with the green fluorescent protein (GFP) expressed in 3T3-L1 preadipocytes was demonstrated by using lentivirus (FIG. 5G). Control vector-transduced cells showed predominantly nuclear GFP signal, which was redistributed to the cytoplasm in cells expressing full length DCN-GFP fusion. In contrast, cells expressing ΔDCN-GFP displayed a markedly distinct localization pattern resembling that of cell surface-bound SPARC (Nie et al., 2008, ibid), which confirmed cell membrane ΔDCN localization.

Example 5

Resistin as an ASC Interactor of ΔDCN

Figure 6A:
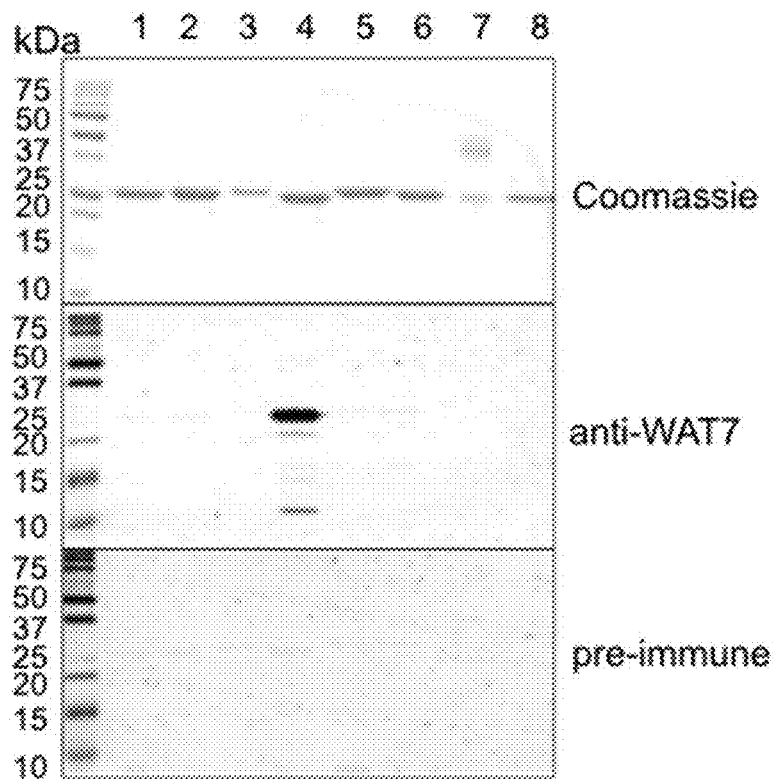
FIGS. 6A-D depict WAT7 binding to ΔDCN by mimicking resistin. (A) Top: Coomassie staining of a gel demonstrating purification of GST (1) and recombinant GST-fused peptides WAT1 (2), WAT2 (3), WAT7 (4), LU2 (5), analyzed in parallel with the following controls: KGGRAKD peptide (6; SEQ ID NO: 26), prohibitin protein (7), and WLGEWLG peptide (SEQ ID NO: 36). Middle: immunoblotting of the same gel with anti-WAT7 antibodies. Bottom: immunoblotting of the same gel with pre-immune serum from a rabbit used for generation of anti-WAT7 antibodies. (B) Immunoblotting of total proteins extracted from mouse cultured 3T3-L1 fibroblasts, cultured ASC, cultured LSC, as well as cells freshly isolated from WAT, bone marrow, or lungs with anti-WAT7 antibodies detects a specific 13 kDa protein (arrowhead). (C) Affinity purification of mouse proteins with anti-WAT7 antibodies from WAT extract. Gel Coomassie staining reveals the same 13 kDa protein, identified as resistin, relative to light (L) and heavy (H) chains of the anti-WAT7 IgG. (D) Measurement of FLAG-tagged resistin and control protein (BAP) binding to recombinant bacterially-purified mouse ΔDCN, as compared to recombinant bacterially-purified full-length core mouse DCN (mDCN), a control his6-tagged protein CLIC4 (Ctrl-prot), full-length glycosylated mouse DCN (mDCN*), glycosylated bovine DCN (bDCN*), and BSA by ELISA. OD450 absorbance, plotted as a function of FLAG-tagged protein concentration, shows dose-dependent ΔDCN/resistin binding.
Figure 6B:
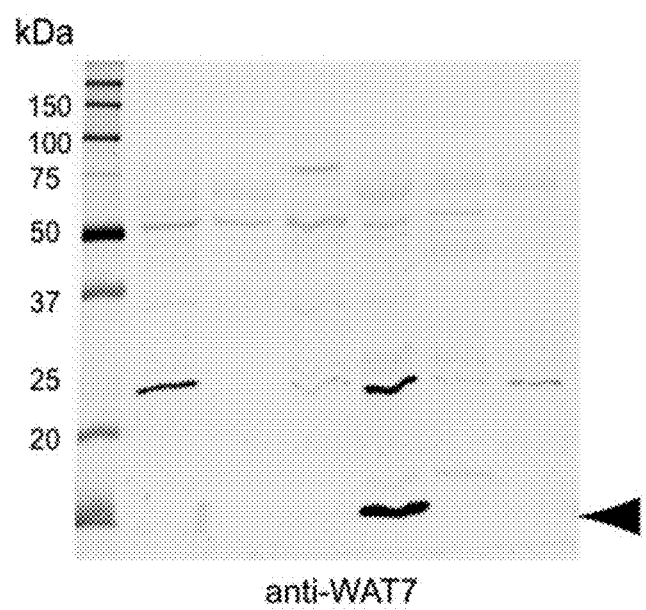

Previous work by the inventors has shown that peptides tend to recognize cell surface receptors by mimicking the receptor-binding domains of the biological ligands for the receptors. Therefore, to characterize the biological interaction behind the WAT7-ΔDCN binding and to identify the biological ligand of ΔDCN, antibodies were elicited against WAT7 by immunizing rabbits with KLH-peptide conjugates, which were expected to recognize the binding epitope of a mouse protein mimicked by WAT7. FIG. 6A demonstrates that the generated WAT7 antibodies have high specificity for WAT7 and do not recognize any of the other ASC-homing peptides isolated in the screen Immunoblotting of mouse protein extracts identified a ~13 kDa protein recognized by WAT7 antibodies (FIG. 6B). This protein was highly abundant in freshly isolated SVF from WAT tissue, but not in lung or bone marrow. Interestingly, its expression was lost upon overnight ASC culturing on plastic in conditions typically used for MSC/ASC propagation (FIG. 6B). This loss is coincident with the loss of ΔDCN cell surface expression in culture (FIG. 5F), suggesting that ΔDCN exposure on ASC is coupled with expression of its ligand.

Figure 6C:
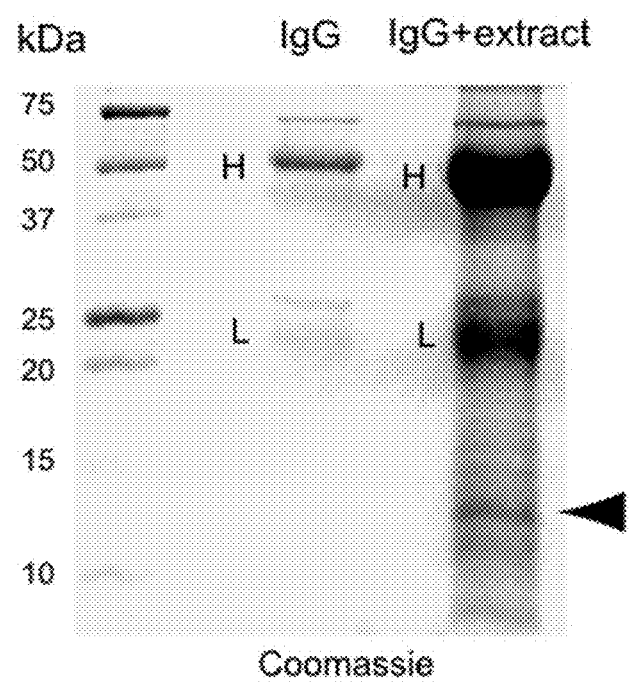
Figure 6D:
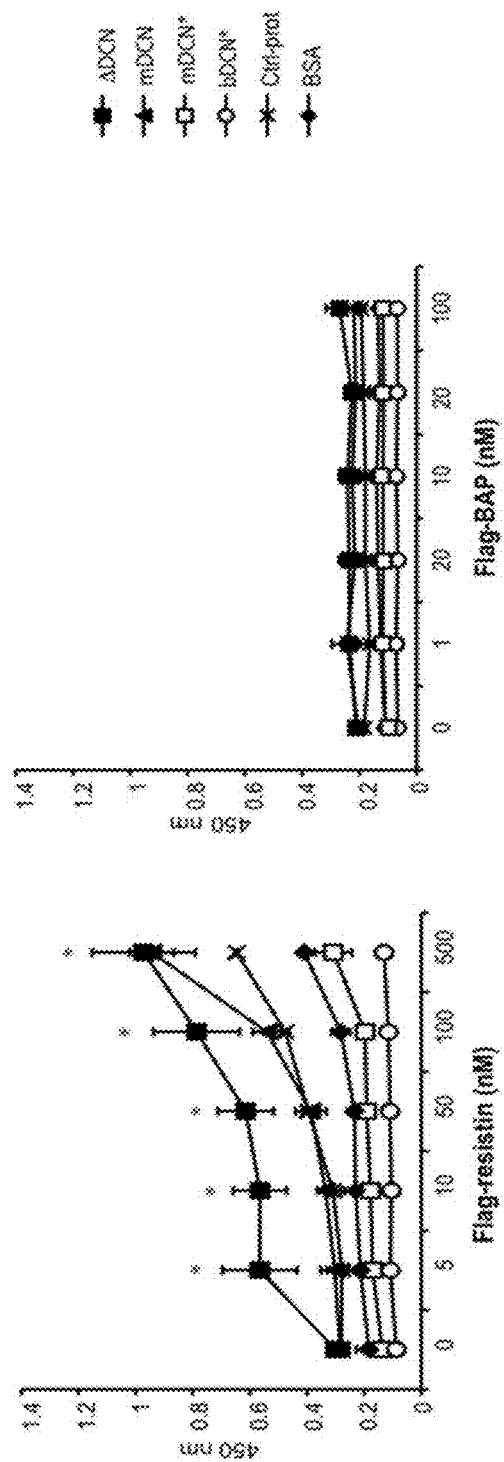

Immobilized anti-WAT7 immunoglobulin (IgG) on Protein A/G beads was used to isolate the ΔDCN ligand and for affinity chromatography on the SFV protein extract. The products of the affinity-capture were resolved by PAGE (FIG. 6C), after which the ~13 kDa band was cut out. Mass spectroscopy identified the protein as resistin (ADSF) known to function as a WAT-secreted adipokine (Steppan et al., Nature 409: 307-312, 2001; Kim et al., J. Biol. Chem. 276: 11252-11256, 2001). Because resistin interaction with DCN has not been previously reported, to confirm the interaction with ΔDCN directly, in vitro binding assays were done with FLAG-tagged mouse resistin. FLAG-tagged bovine alkaline phosphatase (BAP) served as a negative control (FIG. 6D). Resistin was found to bind to ΔDCN at a 100-fold lower molar concentration than to full-length DCN. Interestingly, it was completely inefficient in binding to glycosyated mouse or bovine DCN, as evident from its comparable background BSA and BAP binding. These results indicate that resistin serves as a ligand of ΔDCN.

Figure 7A:
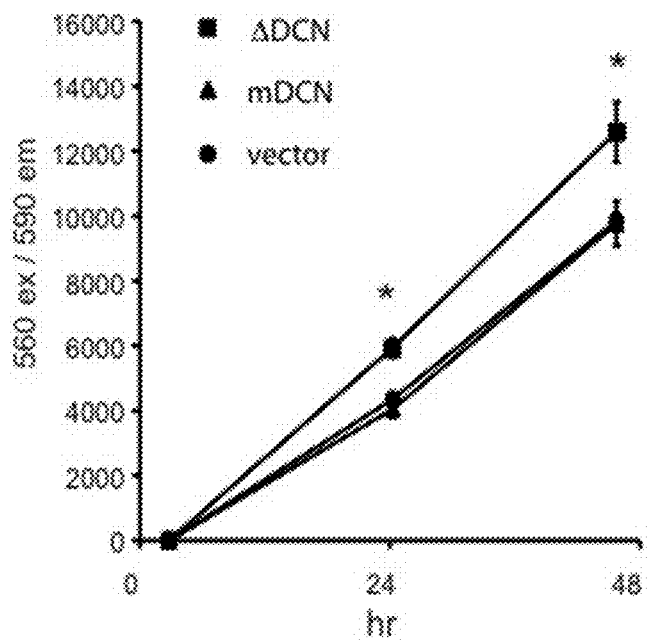
FIGS. 7A-C illustrate the effects of ΔDCN expression on preadipocytes. Functional assays were performed on 3T3-L1 cells stably transduced with lentivirus expressing GFP (vector), full-length core mouse DCN-GFP fusion (DCN), or mouse ΔDCN-GFP fusion (ΔDCN). (A) Proliferation of 5,000 adherent cells at the indicated time points was measured by the MTT assay. Shown are mean±SD of triplicate wells; *P<0.05. (B) Migration of 25,000 pre-starved cells through 5 µM pores toward 10% FBS measured by the Transwell assay. After 12 hr, cells at the bottom of the transwell were fixed, stained, and counted. Values shown are mean±SD for triplicate wells; *P<0.05. (C) Bottom: Adipocyte differentiation measured by lipid droplet accumulation detected with phase contrast microscopy 10 days after induction of adipogenesis. Scale bar: 10 µM.
Figure 7B:
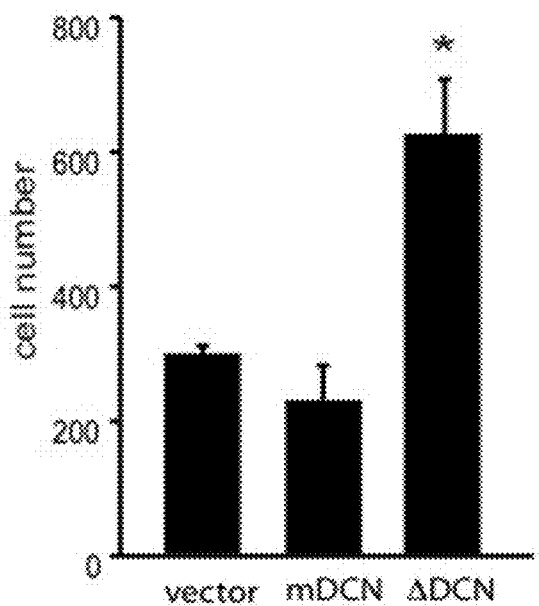
Figure 7C:
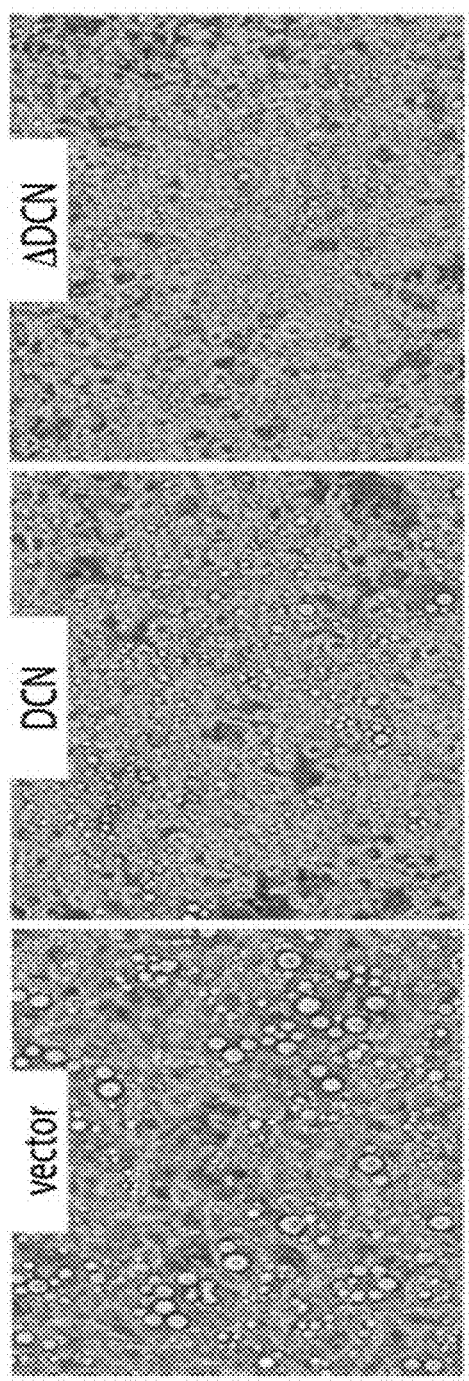

Cell from the 3T3-L1 cell line are a model widely accepted for studying the biology of adipocyte progenitors and were used to characterize the function of ΔDCN. Established 3T3-L1 cultures lentivirally were transduced with ΔDCN-GFP or full-length DCN-GFP fusions; GFP vector alone was used as a control (FIG. 5G). Analysis of cell number increase after 24 hr and 48 hr in culture using the MTT assay demonstrated increased proliferation of cells expressing ΔDCN, compared to cells expressing GFP or full-length DCN-GFP (FIG. 7A). Analysis of cell migration by using the Boyden chamber transwell assay demonstrated a significant increase in the invasiveness of ΔDCN-expressing cells, while cells expressing full length DCN showed the opposite trend, compared to cells expressing GFP (FIG. 7B). These results were confirmed by the in vitro scratch wound assay (data not shown). Finally, cells were subjected to adipogenesis induction to test the effect on cell differentiation (FIG. 7C).

Example 6

Additional Peptides and Evidence of Binding to Human Tissue

Figure 8A:
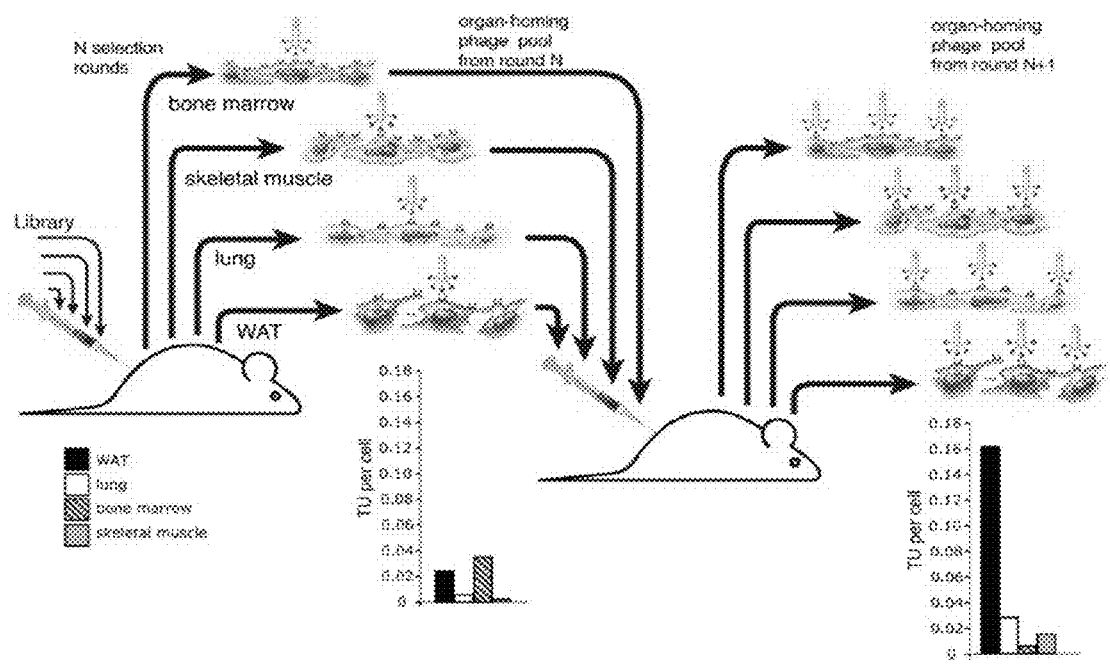
FIG. 8A is a schematic description of synchronous in vivo phage display screening. In every selection round, phage were administered i.v. and simultaneously recovered from n target tissues, amplified, pooled, and used for the next selection round. Increased recovery of phage transforming units (TU) in the later rounds reflects the selection of peptides preferentially homing to the target organ.

Selection of peptides homing to MSC of mouse organs by phage display is illustrated in FIG. 8A which contains a schematic description of synchronous in vivo phage display screening process. In every selection round, phage were administered i.v. and simultaneously recovered from target tissues, amplified then pooled and used for the next round of selection. Increased recovery of phage transforming units (TU) in the later rounds reflects the selection of peptides preferentially homing to the target organ.

Figure 8B:
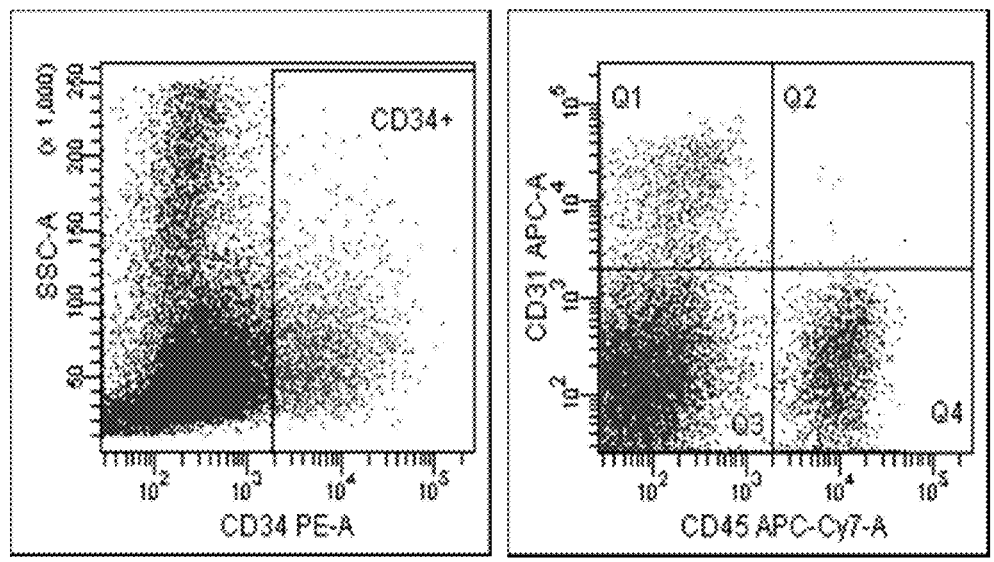
FIG. 8B illustrates identification of MSC by flow cytometry. A representative subcutaneous WAT analysis is shown. Gating on viable cells expressing CD34+ (left scattergram), were then gated based on CD31 and CD45 expression (right scattergram), CD34+CD45−CD31− ASC were identified as purple events in Q3. The purple events in Q1 correspond to CD34+CD45−CD31+ endothelial cells. Events in Q2 and Q4 correspond to CD45+ hematopoietic cells.

FIG. 8B illustrates the identification of MSC using flow cytometry. A representative subcutaneous WAT analysis is shown. Gating of viable cells that were positive for CD34+ (left scattergram) was done first, and then based on expression of CD31 and CD45 (right scattergram), in combination ASC cells were identified as CD34+CD45−CD31− cells which appeared as rare purple events in Q3 of the original scattergram. The purple events that appear in Q1 correspond to CD34+CD45−CD31+ epithelial cells (EC). The events that appear in Q2 and Q4 correspond to CD45+ hematopoietic cells.

A series of peptide clones were identified and enriched using phage display screens on adipose stem cells (ASC) and lung stem cells (LSC) as listed in Table 1, below.

TABLE 1

| MSC | Sequence | SEQ ID NO: | % in WAT | % in LUNG | Re-home to WAT (%) | Re-home to Lung (%) |
|---|---|---|---|---|---|---|
| White Adipose Tissue | | | | | | |
| WAT-1 | KHYGGGVA | 2 | 9.1 | 0 | 1.1 | 9.1 |
| WAT-2 | YKNVDSGG | 4 | 2.9 | 0 | 2.1 | 2.9 |
| WAT-3 | RFLLPQG | 6 | 3.9 | 0 | 0 | 3.9 |
| WAT-4 | YEGSEVS | 8 | 2.9 | 0 | 0 | 2.9 |
| WAT-5 | LRQGNPT | 10 | 1.9 | 0 | 0 | 1.9 |
| WAT-6 | GSGGMSPS | 12 | 1.9 | 0 | 0 | 1.9 |
| WAT-7 | SWKYWFGE | 14 | 5.8 | 0 | 87.4 | 5.8 |
| WAT-8 | GQWLGNWL | 16 | 13.6 | 0 | 0 | 13.6 |
| Lung | | | | | | |
| LU-1 | AVYRSTG | 18 | 0 | 71.6 | 9.5 | 52.2 |
| LU-2 | ESGFPTVG | 20 | 0 | 14.7 | 0 | 40.2 |
| LU-3 | LGVGPGF | 22 | 0 | 5.2 | 0 | 1.1 |
| LU-4 | IRGKAGR | 24 | 0 | 5.2 | 0 | 1.1 |

Shown in Table 1 above are the percent (%) of the sequenced phage clones that carried the indicated WAT or LU insert present within WAT (% in WAT) or lung (% in LUNG) following 4 rounds of synchronous in vivo biopanning on CD34+CD31−CD45− cells.

To demonstrate the selectivity of each clone, equal amounts of phage for clones WAT1, WAT2, WAT3, WAT4, WAT5, WAT6, WAT7, LU1, LU2, LU3 and LU4 were mixed and injected into mice to determine what percent returned (re-home), show are the percent (%) of sequenced phage clones carrying the indicated WAT or LU insert on C34+CD31−CD45− cells isolated from either (Re-home to WAT (%)) or lung (Re-home to LUNG (%)).

Figure 9A:
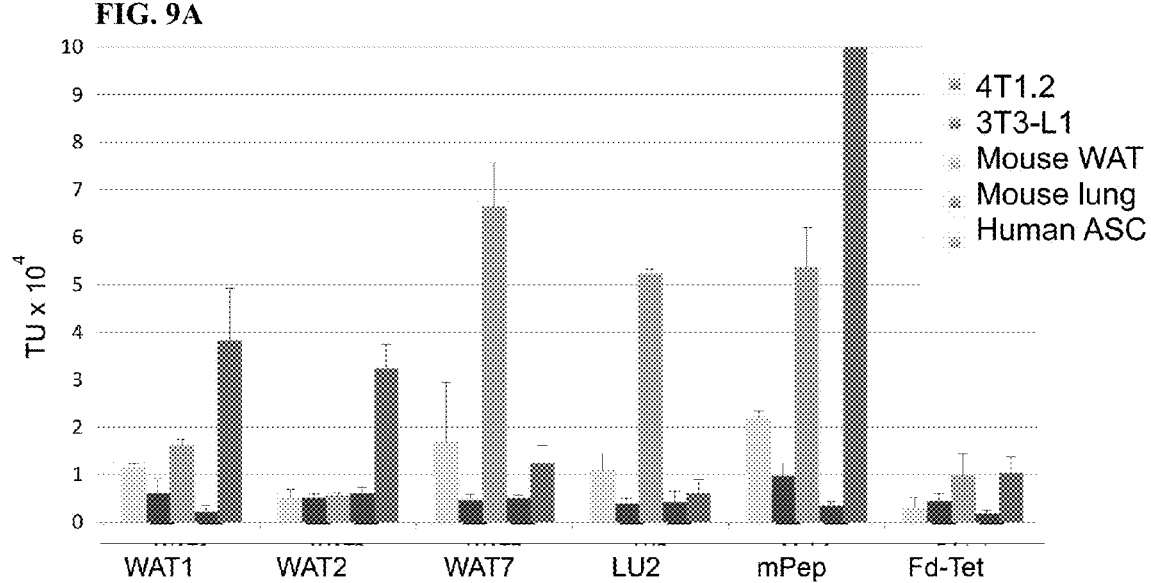
FIG. 9A illustrates selectivity of several of the peptides isolated in the phage display screen were assessed using a phage-cell binding assay. Phage that express the peptide WAT1 (SEQ ID NOS: 1 AND 2), WAT2 (SEQ ID NOS: 3 AND 4), WAT7 (SEQ ID NOS: 13 AND 14), LU2 (SEQ ID NO: 19 and 20), mPep (SEQ ID NOS: 35 AND 36) or phage without insert (Fd-Tet) were assayed for binding on: (1) 4T1.2 cells, endothelial cells derived from a human mammary carcinoma (2) mouse 3T3-L1 cells (a pre-adipose cell line that can be differentiated into an adipocyte-like phenotype); (3) primary mouse SVF cells from WAT; (4) primary mouse SVF cells from lung, and; (5) passage 4 of human ASC cells from WAT (bars left to right). The indicated peptide-phage along with insertless Fd-tet control phage were added (10$^8$ TU) for 1 hr at 37 C. After washing 3× with RPMI/1% BSA, cells were dowsed with a homogenizer. Recovered phage was used to infect K91 E coli, and upon tetracyline selection colonies were counted to quantify average transforming units (TU). Shown are mean values for three individual platings±SEM (error bars).

Selectivity of several of the peptides isolated in the phage display screen were assessed using a phage-cell binding assay. Phage that express the peptide WAT1, WAT2, WAT7, LU2, mPep or Fd-Tet were assayed for binding on: (1) 4T1.2 cells, endothelial cells derived from a human mammary carcinoma (2) mouse 3T3-L1 cells (a pre-adipose cell line that can be differentiated into an adipocyte-like phenotype); (3) primary mouse SVF cells from WAT; (4) primary mouse SVF cells from lung, and; (5) passage 4 of human ASC cells from WAT (obtained originally during liposuction. Target cells were detached with 2.5 mM EDTA and 100,000 cells were resuspended in 0.2 ml of RPMI containing 1% BSA. The indicated peptide expressing phage along with a phage control (without inserts) Fd-tet were added ($10^8$ TU) for 1 hr at 37° C. After washing 3 times with RPMI containing 1% BSA, cells were dounced with a homogenizer. The recovered phage were used to infect K91 E coli, and following tetracyline selection, colonies were enumerated to quantify average transforming units (TU). Shown in FIG. 9A are mean values for three individual platings+SEM (error bars). The human ASC used to generate the finding presented in FIG. 9A had undergone 4 passages when used to demonstrate WAT7 binding to these cells. It was hypothesized that because ΔDCN binds selectively to freshly isolated mouse ASC and not well to repeatedly passaged mouse ASC, that this preference in the ΔDCN/WAT7 targeting system might be preserved.

Figure 9B:
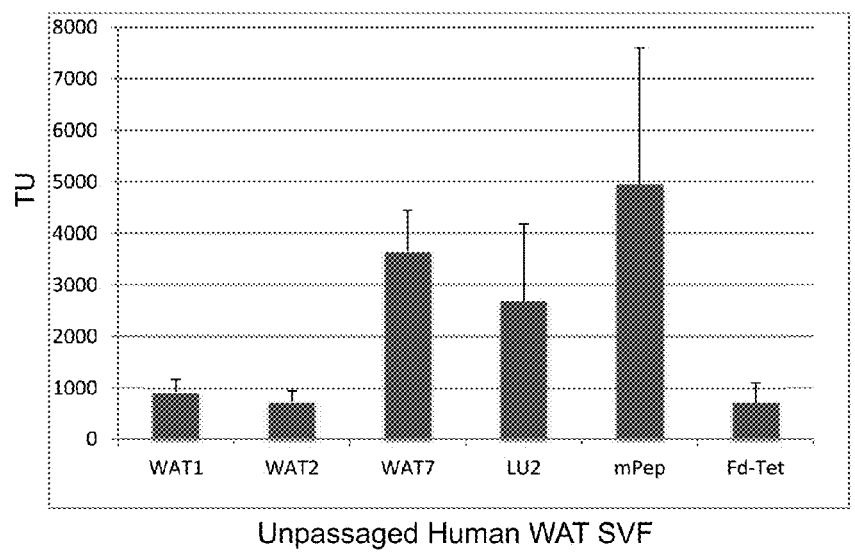
FIG. 9B illustrates selectivity of several of the peptides isolated in the phage display screen were assessed using a phage-cell binding assay. Phage that express the peptide WAT1 (SEQ ID NOS: 1), WAT2 (SEQ ID NOS: 3), WAT7 (SEQ ID NOS: 13), LU2 (SEQ ID NO: 19), mPep (SEQ ID NOS: 35) or phage without insert (Fd-Tet) were assayed for binding on unpassaged human WAT SVF. The indicated peptide-phage along with insertless Fd-tet control phage were added (10$^8$ TU) for 1 hr at 37 C. After washing 3× with RPMI/1% BSA, cells were dounced with a homogenizer. Recovered phage was used to infect K91 E coli, and upon tetracyline selection colonies were counted to quantify average transforming units (TU). Shown are mean values for three individual platings±SEM (error bars).

To demonstrate that indeed WAT7 does bind to unpassaged human ASC, fresh human ASC was used as a target tissue (the binding of each of the phage expressed peptide is illustrated in FIG. 9B. It was therefore demonstrated that WAT7 bound unpassaged human ASC better than WAT1 and WAT2 peptides. This activity mirrors the pattern of WAT-homing peptides to freshly-isolated mouse ASC which suggests that DCN biology is conserved and that delta-DCN/WAT7 targeting system can be used in other mammalian subjects including humans.

Example 7

Cytotoxic Peptides and Evidence of In Vivo Activity of Peptide Composition

Figure 10:
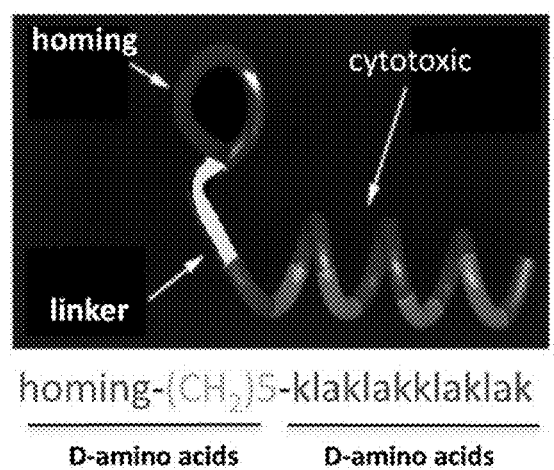
FIG. 10 illustrates the structure of a chimeric targeted cytotoxic peptide in which the homing or targeting cyclic peptide is coupled through a linker to a cytotoxic/pro-apoptotic peptide.
Figure 11:
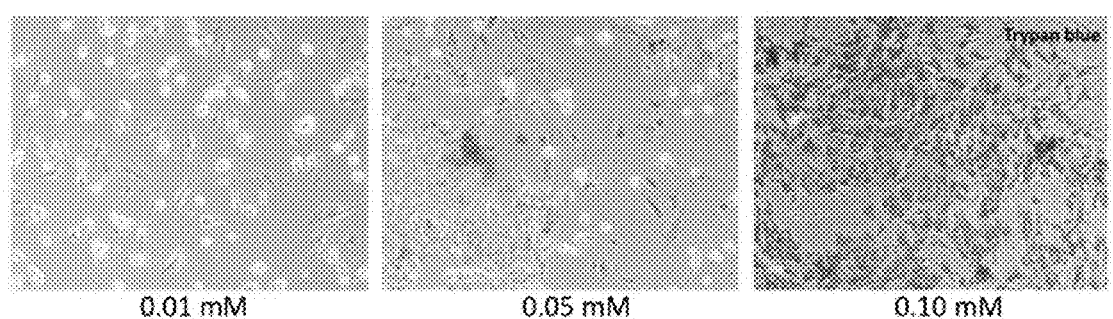
FIG. 11 illustrates the dose dependent in vitro killing activity of WAT7-KLAKLAK$_2$ (SEQ ID NO:13-SEQ ID NO:31) (all-D-peptide (0.01 mM, 0.05 mM and 0.10 mM) and thus the ability of the ASC-homing peptide termed WAT7 (SEQ ID NO:13) to target efficient killing of primary mouse ASC in culture, as visualized using trypan blue exclusion.
Figure 12:
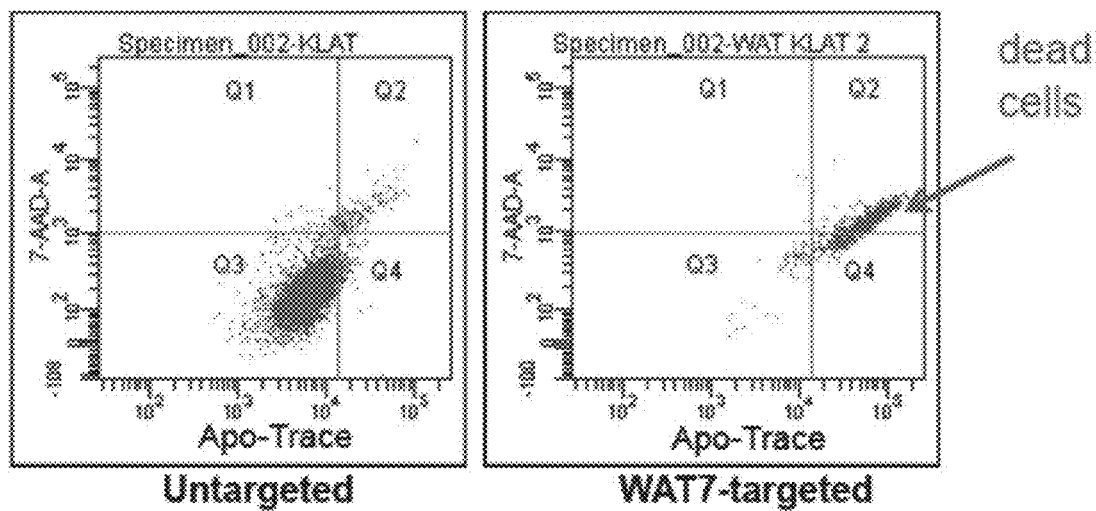
FIG. 12 illustrates validation that apoptosis was the cause of death in cells treated with WAT7-KLAKLAK$_2$ (SEQ ID NO:13-SEQ ID NO:31) all-D-peptide. APO-TRACE reagent (Sigma) and flow cytometry were used to detect apoptosis induction in treated cells to validate apoptosis as the mechanism of cell death. Cells treated with untargeted apoptotic peptide and those treated with WAT7 targeted apoptotic peptide are shown.

Targeted aminohexanoic acid-linked cytotoxic proteolysis-resistant all-D-enantiomer peptides were designed for selective in vivo depletion of cell populations of interest. These peptides were synthetic and were composed of two functional domains: a homing (cell targeting) domain binding to a receptor differentially expressed on cells of interest (in this particular example cyclic WAT7 (SEQ ID NO:13)) and a cytotoxic domain to induce apoptotic death of cells that internalize the peptide. The homing peptide was typically 7 to 8 amino acids long and is cyclic (constrained by two disulfide-bonded cysteines). The cytotoxic domain was an amphipatic peptide sequence KLAKLAKKLAKLAK (SEQ ID NO: 31) designated $(KLAKLAK)_2$, which disrupts mitochondrial membranes upon receptor-mediated cell internalization and causes programmed cell death (apoptosis). All amino acids in both domains were D-enantiomers, which are resistant to proteolysis in vivo, thus allowing long-term effects of the peptide upon systemic administration. The linker connecting the two domains is aminohexanoic acid (Ahx): NH—(CH2)5-CO, which is also resistant to cleavage by proteases in vivo. The resulting chimeric peptide (illustrated in FIG. 10) is a WAT7-KLAKLAK$_2$ (SEQ ID NO: 44) protein composition that was produced by Celtek. Peptides designed and manufactured based on the composition design introduced herein were injected systemically into mice in order demonstrate the activity of the cytotoxic peptide composition to selectively deplete cell populations. This technology was validated by using peptides targeting adipose stromal/stem cells (ASC) in white adipose (fat) tissue (WAT). As demonstrated in FIG. 11, primary mouse ASC were efficiently killed by treatment with WAT7-KLAKLAK$_2$ (SEQ ID NO: 44) in a concentration dependent manner as evidenced using trypan blue dye exclusion staining (FIG. 11). Using flow cytometry and the APO-TRACE reagent (Sigma) evidence of the induction of apoptosis was established, validating apoptosis as the cell death mechanism induced by cytotoxic peptide exposure (FIG. 12).

Figure 13:
FIG. 13 shows obese mice 48 hours after treatment with 2 mg of control or with the targeted cytotoxic peptide, WAT7-KLAKLAK$_2$ (SEQ ID NO:13-SEQ ID NO:31) all-D-peptide. It can be seen that the mouse treated with the targeted cytotoxic peptide, WAT7-KLAKLAK$_2$ (SEQ ID NO:13-SEQ ID NO:31) all-D-peptide has a reduction in the amount of adipose tissue.
Figure 15:
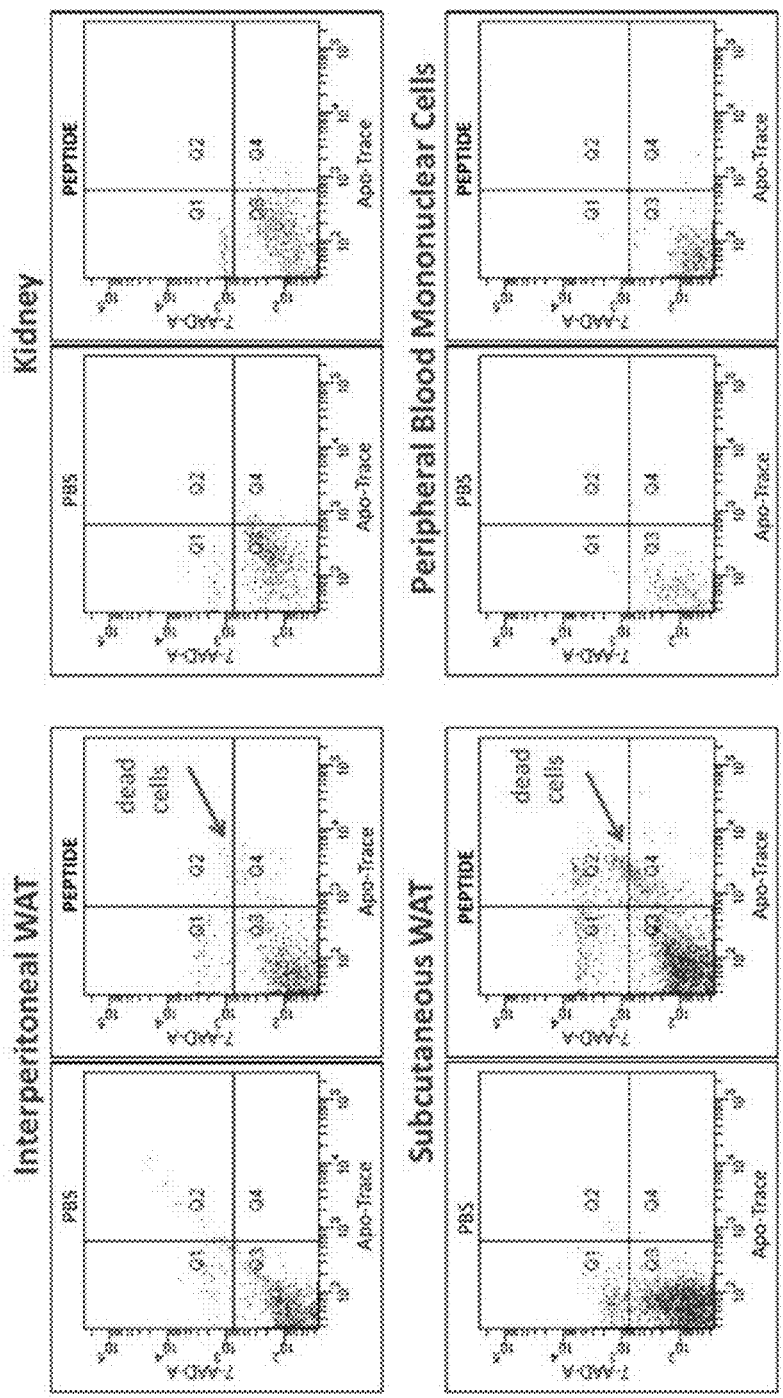
FIG. 15 illustrates that apoptosis induced by treatment with cytotoxic WAT7-KLAKLAK$_2$ (SEQ ID NO:13-SEQ ID NO:31) all-D-peptide was limited to target tissue. APO-TRACE reagent (Sigma) and flow cytometry were used to detect apoptosis induction in both subcutaneous and intraperitoneal WAT cells, but not in cells from the kidney or peripheral blood. The lack of non targeted apoptosis indicates that the cytotoxic chimeric peptides are resistant to proteolysis.

As demonstrated by the mice shown in FIG. 13, the injection of 2 mg of WAT7-KLAKLAK$_2$ (SEQ ID NO: 44) all-D-peptide into obese mice resulted in the demonstrated reduction in intraperitoneal adipose tissue. This reduction was due to the targeted depletion of ASC through apoptotic cell death as evidenced at 48 hrs after injection (see FIG. 14). The amount of ASC present in subcutaneous WAT (panel E versus F) was reduced by treatment with the targeted cytotoxic peptide, WAT7-KLAKLAK$_2$ (SEQ ID NO: 44) all-D-peptide, the amount of ASC present in intraperitoneal WAT was even more greatly reduced (panel G versus H) and this also resulted in tumor necrosis as shown in the top panels (panel A versus B) or as evidenced by the reduction of tumor as shown with fluorescence (panel C versus D). FIG. 15 shows that treatment with targeted cytotoxic peptide, WAT7-KLAKLAK$_2$ (SEQ ID NO: 44) all-D-peptide, resulted in apoptotic cell deal in ASC present in both subcutaneous and intraperitoneal adipose tissue (left side panels). In contrast, no apoptotic cell death was identified in cells obtained from the kidney or peripheral blood of treated mice (right side panels of FIG. 15), indicating that that the apoptosis inducing peptide was not released by proteolysis from the targeting portion of the chimeric targeted peptide protein composition. No MTD was reached with increasing peptide doses. This indicates that cytotoxic targeted peptides constructed by the methods described are resistant to proteolytic cleavage and can be used in vivo to successfully target and kill ASC and reduce adipose tissue.

Without further elaboration, it is believed that one skilled in the art can, using the description herein, utilize the present methods to their fullest extent. The embodiments described herein are to be construed as illustrative and not as constraining the remainder of the disclosure in any way whatsoever. While preferred embodiments have been shown and described, many variations and modifications thereof can be made by one skilled in the art without departing from the spirit and teachings of the presently disclosed methods. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they provide procedural or other details consistent with and supplementary to those set forth herein.

What is claimed is:

1. A polypeptide comprising the amino acid sequence selected from the group consisting of CSWKYWFGEC (SEQ ID NO:13) and SWKYWFGE (SEQ ID NO:14), wherein the polypeptide binds to cells that express a proteolytic cleavage product of decorin (ADCN).

2. The polypeptide of claim 1, wherein the peptide comprises the amino acid sequence of CSWKYWFGEC (SEQ ID NO:13).

3. The polypeptide of claim 1, wherein said polypeptide is composed entirely of D-amino acids.

4. The polypeptide of claim 1, wherein said polypeptide is coupled to an effector agent selected from the group consisting of: an imaging agent; a cytotoxic agent; a proapoptotic agent; a fusion protein; a cytostatic agent; a cytocidal agent; radioisotope; an adipose stromal cell (ASC) cell differentiating agent; mitotic inhibitors; antitumor agent; antibiotic agent; enzymes; chemotherapeutic agent; anti-angiogenic agent or a combination thereof.

5. The polypeptide of claim 4, wherein said polypeptide and effector agent are comprised of D-amino acids.

6. The polypeptide of claim 4 wherein said effector agent is selected from the group consisting of: gramicidin; magainin; mellitin; defensin; cecropin; (KFAKFAK)$_2$ (SEQ ID NO: 37); (KFXAKFXAK)$_2$ (SEQ ID NO: 38); (KHexAKHexAK)$_2$(KLAKLAK)$_2$ (SEQ ID NO: 43); (KLAKKLA)$_2$ (SEQ ID NO: 32); (KAAKKAA)$_2$ (SEQ ID NO: 33); (KLGKKLG)$_3$ (SEQ ID NO: 34); angiotensin; laminin peptides; fibronectin peptides; plasminogen activator inhibitors; tissue metalloproteinase inhibitors; interferons; interleukin 12; platelet factor 4; IP-10; Gro-13; thrombospondin; 2-methoxyoestradiol; proliferin-related protein; carboxiamidotriazole; CM101; Marimastat; pentosan polysulphate; angiopoietin 2; interferon-alpha; herbimycin A; PNU145156E; 16K prolactin fragment; thalidomide; pentoxifylline; genistein; TNP470; endostatin; paclitaxel; accutin; angiostatin; cidofovir; vincristine; AGM-1470; platelet factor 4 or minocycline; 5-fluorouracil; bleomycin; busulfan; camptothecin; carboplatin; chlorambucil; cisplatin (CDDP); cyclophosphamide; dactinomycin; daunorubicin; doxorubicin; estrogen receptor binding agents; etoposide (VP16); farnesyl-protein transferase inhibitors; gemcitabine; ifosfamide; mechlorethamine; melphalan; mitomycin; navelbine; raloxifene; tamoxifen; taxol; temazolomide; transplatinum; vinblastine and methotrexate; alkylating agents; antimetabolites; antitumor antibiotics; corticosteroid hormones; mitotic inhibitors; nitrosoureas; hormone agents; mitotic inhibitors; enzymes; plant alkaloids; docetaxel; teniposide; vinorelbine; PPAR-gamma agonists; thiazolidindiones; rosiglitazone; fluorophores; metal chelate complexes; radioisotopes; fluorescent markers; urease; alkaline phosphatase; liposomes; microcapsules; microparticles;

nanoparticles; magnetic beads; microdevices; plicamycin; platinum coordination complexes; anthracenediones; substituted ureas; methyl hydrazine derivatives; amsacrine; L-asparaginase; tretinoin; mitoxantrone; hydroxyurea; procarbazine; IgFc fusion proteins; enzyme fusion proteins; fluorescent proteins; luminescent proteins and combinations thereof.

7. A method of treating cancer in a subject comprising administering an effective amount of a polypeptide according to claim 1 to the subject, wherein said polypeptide is coupled to an effector agent and wherein the subject comprises adipose stromal cells in the tumor tissue.

8. The method of claim 7, wherein the effector agent is a cytotoxic agent.

9. The method of claim 8, wherein the effector agent is a chemotherapeutic agent.

10. The method of claim 7 wherein said effector agent is selected from the group consisting of: gramicidin; magainin; mellitin; defensin; cecropin; (KFAKFAK)$_2$ (SEQ ID NO: 37); (KFXAKFXAK)$_2$ (SEQ ID NO: 38); (KHexAKHexAK)$_2$(KLAKLAK)$_2$ (SEQ ID NO: 43); (KLAKKLA)$_2$ (SEQ ID NO: 32); (KAAKKAA)$_2$ (SEQ ID NO: 33); (KLGKKLG)$_3$ (SEQ ID NO: 34); angiotensin; laminin peptides; fibronectin peptides; plasminogen activator inhibitors; tissue metalloproteinase inhibitors; interferons; interleukin 12; platelet factor 4; IP-10; Gro-13; thrombospondin; 2-methoxyoestradiol; proliferin-related protein; carboxiamidotriazole; CM101; Marimastat; pentosan polysulphate; angiopoietin 2; interferon-alpha; herbimycin A; PNU145156E; 16K prolactin fragment; thalidomide; pentoxifylline; genistein; TNP470; endostatin; paclitaxel; accutin; angiostatin; cidofovir; vincristine; AGM-1470; platelet factor 4 or minocycline; 5-fluorouracil; bleomycin; busulfan; camptothecin; carboplatin; chlorambucil; cisplatin (CDDP); cyclophosphamide; dactinomycin; daunorubicin; doxorubicin; estrogen receptor binding agents; etoposide (VP16); farnesyl-protein transferase inhibitors; gemcitabine; ifosfamide; mechlorethamine; melphalan; mitomycin; navelbine; raloxifene; tamoxifen; taxol; temazolomide; transplatinum; vinblastine and methotrexate; alkylating agents; antimetabolites; antitumor antibiotics; corticosteroid hormones; mitotic inhibitors; nitrosoureas; hormone agents; mitotic inhibitors; enzymes; plant alkaloids; docetaxel; teniposide; vinorelbine; PPAR-gamma agonists; thiazolidinediones; rosiglitazone; fluorophores; metal chelate complexes; radioisotopes; fluorescent markers; urease; alkaline phosphatase; liposomes; microcapsules; microparticles; nanoparticles; magnetic beads; microdevices; plicamycin; platinum coordination complexes; anthracenediones; substituted ureas; methyl hydrazine derivatives; amsacrine; L-asparaginase; tretinoin; mitoxantrone; hydroxyurea; procarbazine; IgFc fusion proteins; enzyme fusion proteins; fluorescent proteins; luminescent proteins and combinations thereof.

11. The method of claim 7, wherein the polypeptide comprises the sequence of SEQ ID NO: 13.

12. The method of claim 7, wherein the polypeptide is comprised of D-amino acids.

13. The method of claim 7, wherein the polypeptide is less than 100 amino acids in length.

14. The method of claim 7, wherein the polypeptide is coupled to the effector agent by a linking moiety.

15. The method of claim 14, wherein the linking moiety comprises aminohexanoic acid; $(CH_2)_4$; $(CH_2)_5$; $(CH_2)_6$; $(CH_2)_7$; or $(CH_2)_8$.

* * * * *